（12）United States Patent
Fujiwara et al.

(10) Patent No.: US 10,067,056 B2
(45) Date of Patent: Sep. 4, 2018

(54) OPTICAL SENSOR, OPTICAL INSPECTION DEVICE, AND OPTICAL PROPERTY DETECTION METHOD FOR DETECTING LIGHT PROPAGATED INSIDE A TEST OBJECT

(71) Applicants: Masayuki Fujiwara, Miyagi (JP); Toshihiro Ishii, Miyagi (JP); Yoichiro Takahashi, Miyagi (JP); Toshihide Sasaki, Miyagi (JP)

(72) Inventors: Masayuki Fujiwara, Miyagi (JP); Toshihiro Ishii, Miyagi (JP); Yoichiro Takahashi, Miyagi (JP); Toshihide Sasaki, Miyagi (JP)

(73) Assignee: Ricoh Company, Ltd., Tokyo (JP)

( * ) Notice: Subject to any disclaimer, the term of this patent is extended or adjusted under 35 U.S.C. 154(b) by 101 days.

(21) Appl. No.: 14/982,659

(22) Filed: Dec. 29, 2015

(65) Prior Publication Data

US 2016/0195473 A1    Jul. 7, 2016

(30) Foreign Application Priority Data

Jan. 6, 2015 (JP) ................................. 2015-000626
Dec. 7, 2015 (JP) ................................. 2015-238379

(51) Int. Cl.
*G01N 21/49* (2006.01)
*G01J 1/04* (2006.01)
(Continued)

(52) U.S. Cl.
CPC ........... *G01N 21/49* (2013.01); *A61B 5/0042* (2013.01); *A61B 5/0261* (2013.01);
(Continued)

(58) Field of Classification Search
CPC . A61B 5/0261; A61B 5/1455; A61B 5/15136; G01N 21/49; G01N 21/4795
(Continued)

(56) References Cited

U.S. PATENT DOCUMENTS 5,575,285 A * 11/1996 Takanashi .......... A61B 5/14551
356/41
2007/0164201 A1   7/2007 Liess et al.
(Continued)

FOREIGN PATENT DOCUMENTS

JP        11-169361 A       6/1999
JP        2002-000586       1/2002
(Continued)

OTHER PUBLICATIONS

Extended European Search Report dated Jun. 16, 2016 in Patent Application No. 16150070.7.
(Continued)

*Primary Examiner* — Que T Le
(74) *Attorney, Agent, or Firm* — Oblon, McClelland, Maier & Neustadt, L.L.P.

(57) ABSTRACT

An optical sensor including an irradiation system including at least one light irradiator, the at least one irradiator including a surface emitting laser array having a plurality of light-emitting units, and a lens disposed in an optical path of the plurality of rays of light emitted from the plurality of light-emitting units to cause light exit directions of at least two of the plurality of light-emitting units to be not parallel to each other, such that the at least one irradiator irradiates a same point of a test object with a plurality of rays of light that are not parallel to each other. The optical sensor also including a detection system configured to detect the plurality of rays of light that are emitted from the irradiation system and propagated inside the test object.

14 Claims, 36 Drawing Sheets

(51) Int. Cl.
    *A61B 5/026*     (2006.01)
    *A61B 5/00*     (2006.01)
    *A61B 5/1455*     (2006.01)
    *G01N 21/359*     (2014.01)
    *G01N 21/47*     (2006.01)

(52) U.S. Cl.
    CPC ........... *A61B 5/1455* (2013.01); *G01J 1/0411* (2013.01); *G01N 21/359* (2013.01); *G01N 21/4795* (2013.01); *A61B 2562/0233* (2013.01); *A61B 2562/146* (2013.01); *A61B 2562/16* (2013.01); *G01N 2201/068* (2013.01); *G01N 2201/0612* (2013.01)

(58) Field of Classification Search
    USPC ...................................... 250/221, 216, 559.4
    See application file for complete search history.

(56) References Cited

U.S. PATENT DOCUMENTS

2007/0232911 A1    10/2007  Urano
2016/0242647 A1*   8/2016  Ishii ..................... A61B 5/1455

FOREIGN PATENT DOCUMENTS

JP        2004-290544 A    10/2004
JP        2015-092151      5/2015
WO    WO2015/046624 A1   4/2015

OTHER PUBLICATIONS

Venkaiah C. Kavuri, et al. "Sparsity enhanced spatial resolution and depth localization in diffuse optical tomography", Biomedical Optics Express, vol. 3, No. 5, XP055277738, 2012, pp. 943-957.
Office Action for European Patent Application No. 16150070.7 dated Jun. 1, 2018.

* cited by examiner

| DEPTH (mm) | CONTROL SAMPLE | SECOND EXAMPLE 2 |
|---|---|---|
| 2 | × | ○ |
| 4 | × | ○ |
| 6 | × | ○ |
| 8 | × | ○ |
| 10 | × | ○ |
| 12 | × | ○ |
| 14 | × | ○ |
| 16 | × | ○ |
| 17 | × | × |

OPTICAL SENSOR, OPTICAL INSPECTION DEVICE, AND OPTICAL PROPERTY DETECTION METHOD FOR DETECTING LIGHT PROPAGATED INSIDE A TEST OBJECT

CROSS-REFERENCE TO RELATED APPLICATIONS

This patent application is based on and claims priority pursuant to 35 U.S.C. § 119(a) to Japanese Patent Application Nos. 2015-000626 and 2015-238379, filed on Jan. 6, 2015, and Dec. 7, 2015, respectively, in the Japan Patent Office, the entire disclosure of which is hereby incorporated by reference herein.

BACKGROUND

Technical Field

Embodiments of the present invention relate to an optical sensor, an optical inspection device provided with the optical sensor, and an optical property detection method using the optical sensor.

Background Art

Conventionally, an optical living-body measuring device that irradiates a test object (living body) with light to detect the light that has propagated inside the test object is known. In such an optical living-body measuring device, the pitches of a plurality of probes provided for a test object are made smaller to achieve higher resolution.

SUMMARY

Embodiments of the present invention described herein provide an optical sensor including an irradiation system including at least one light irradiator, the at least one irradiator including a surface emitting laser array having a plurality of light-emitting units, and a lens disposed in an optical path of the plurality of rays of light emitted from the plurality of light-emitting units to cause light exit directions of at least two of the plurality of light-emitting units to be not parallel to each other, such that the at least one irradiator irradiates a same point of a test object with a plurality of rays of light that are not parallel to each other. The optical sensor also includes a detection system configured to detect the plurality of rays of light that are emitted from the irradiation system and propagated inside the test object.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

Figure 1:
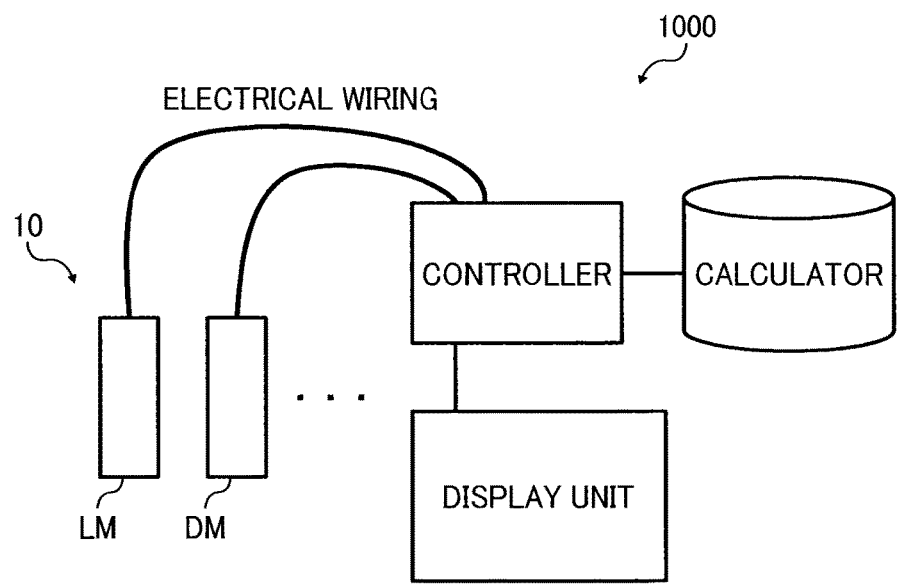
FIG. 1 is a diagram illustrating an outline of the configuration of an optical inspection device according to a first embodiment of the present invention.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

First Embodiment

In the following description, a first embodiment of the present invention is described with reference to FIG. 1 to FIG. 40. FIG. 1 is a schematic diagram illustrating the configuration of an optical inspection device 1000 according to the first embodiment of the present invention.

For example, the optical inspection device 1000 is used for the diffuse optical tomography (DOT). The DOT is a technique in which a test object (scatterer) such as a living body is irradiated with light and the light that has propagated inside the test object is detected to estimate the internal optical property of the test object. In particular, the application to aids for differential diagnosis of depression, and the application to ancillary equipment of rehabilitation, by detecting the bloodstream inside a brain, are expected. In the DOT, an improvement in resolution leads to a better understanding of the functions of the brain. For this reason, active studies are set out in many research institutions to improve the resolution.

Figure 46:
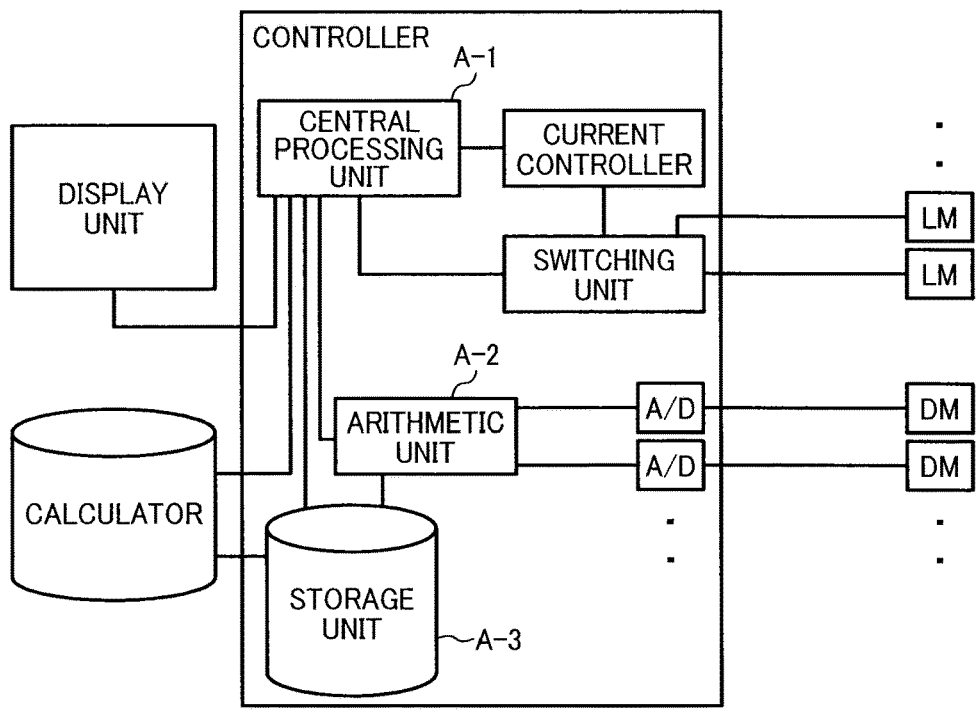
FIG. 46 is a block diagram illustrating the configuration of a controller according to the embodiments of the present invention.

As illustrated in FIG. 1, the optical inspection device 1000 includes, for example, a controller, a display unit, a calculator, and an optical sensor 10 provided with a detection module DM and a light source module LM including a plurality of light-emitting units. The controller is configured as illustrated in the block diagram of FIG. 46. In the controller, the switching unit is controlled according to the data sent from a central processing unit A-1 to select the light source module LM to emit light. In so doing, the current that is supplied to the light source module LM through the switching unit is controlled by the current controller to have a value as desired. The detection result (data) of the detection module DM is analog-to-digital (A/D) converted, and operation such as averaging is performed at an arithmetic unit A-2. The results of the operation performed at the arithmetic unit A-2 is sequentially stored in a storage unit A-3.

In the following description, the light source module LM and the detection module DM may be referred to as a probe when it is not necessary to distinguish between these two elements. In the following description, terms such as a pseudo living body, a living body, and a test object are used. It is to be noted that a pseudo living body and a living body are examples of the test object.

The optical sensor 10 can generally be used as a sensor that detects a light absorber in the test object, but the test object with the highest utility value is a living body. However, as known in the art, it is not always easy to detect the position of the bloodstream (light absorber) of a living body by using an optical sensor. In other words, it is difficult to check the effectiveness (accuracy of detection) of the optical sensor 10 when the test object is a living body.

In order to deal with such situation and achieve versatility, in the present embodiment, a pseudo living body, i.e., whitish liquid in a watertank, is adopted as a test object in which the accuracy of detection can easily be checked. In the following description, such a pseudo living body may be referred to as phantom.

A first example of the present embodiment is described below.

First Example

Figure 2:
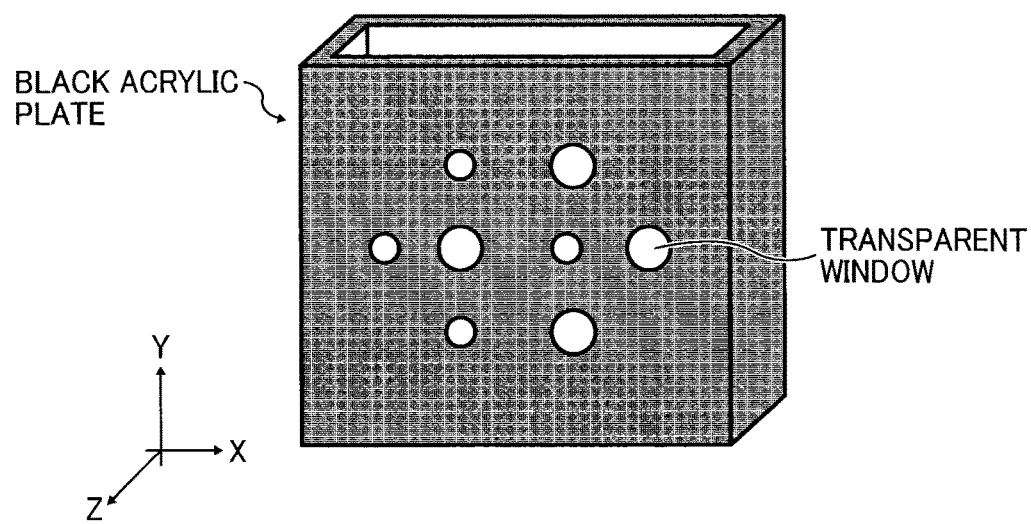
FIG. 2 is a diagram illustrating a watertank for a phantom according to the first embodiment of the present invention.

FIG. 2 is a diagram illustrating a watertank for a phantom according to the first embodiment of the present invention. In the first example, a method is adopted in which the light beams emitted from a plurality of light-emitting units are deflected by a prism to vary the incident angle to the test object for each of the light beams. In the present example, as illustrated in FIG. 2, transparent windows are formed at eight positions on a side wall of a watertank whose walls are made of black acrylic plate. These transparent windows are made of clear acrylic plate. The watertank is filled with intralipid aqueous solution (ten-times diluted intralipid aqueous solution at a 10 percent concentration). In other words, the pseudo living body used in the first example is intralipid aqueous solution. More specifically, black ink is dripped into the intralipid aqueous solution filled in the watertank to the degree of about parts per million (ppm). Accordingly, the absorption coefficient and scattering coefficient that are almost equivalent to those of a living body can be achieved. Then, a black light absorber simulating bloodstream is sunk into the whitish intralipid aqueous solution. In the present example, the light absorber is black polyacetal, and has an approximately 5 millimeters (mm) spherical body in diameter. In order to control the position of such a spherical body, the spherical body is attached to a thin 1 mm metallic rod in diameter, and the rod is connected to an automatic positioning stage. A probe is precisely aligned to each of the transparent windows of the watertank, and is attached thereto.

In the present example, the volume of the watertank is 140 mm×140 mm×60 mm. The thickness of the black acrylic plate is 4 mm. The eight transparent windows are composed of circular transparent windows A and B with varying two sizes. There are four transparent windows A and four transparent windows B. The diameter of the transparent window A is 9 mm, and the diameter of the transparent window A is 12 mm. The thickness of both the transparent windows A and B is 1.5 mm.

Figure 3:
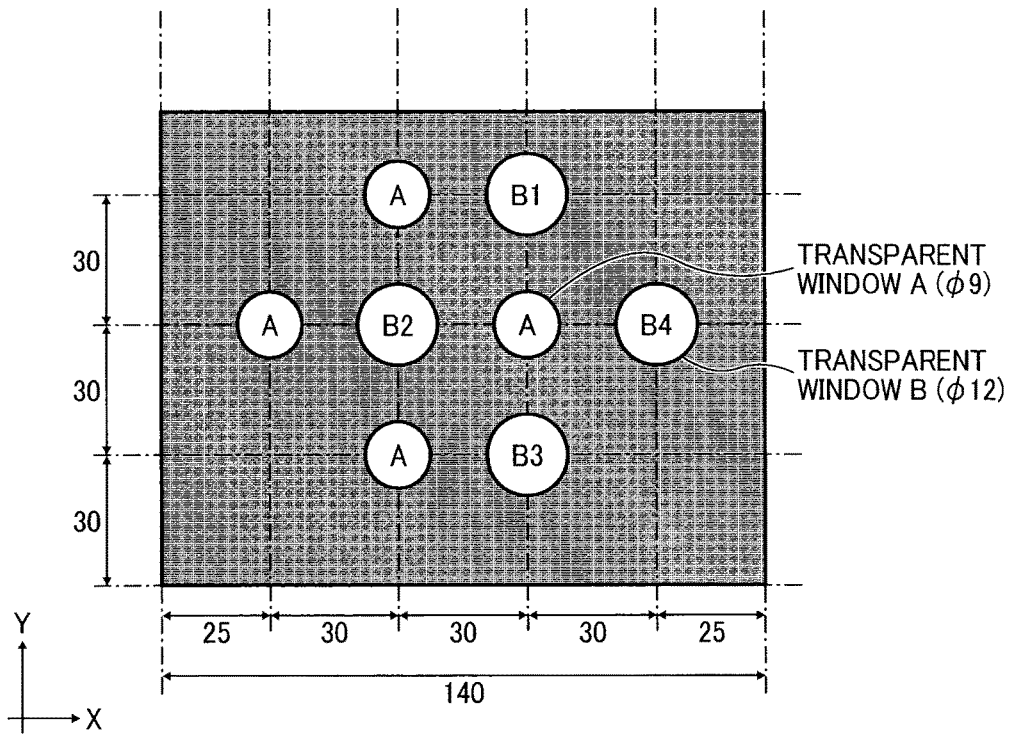
FIG. 3 is a diagram illustrating the layout of a transparent window according to the first embodiment of the present invention.

FIG. 3 illustrates the layout of the eight transparent windows according to the present embodiment. The eight transparent windows are arranged at even intervals in the X-axis direction and the Y-axis direction like a grid such that the transparent windows A and the transparent windows B are next to each other in an alternating manner. In the present example, the detection module DM is attached to each of the transparent windows A, and the light source module LM is attached to each of the transparent windows B (B1 to B4). The distance between the centers of the two neighboring transparent windows is 30 mm.

Figure 4:
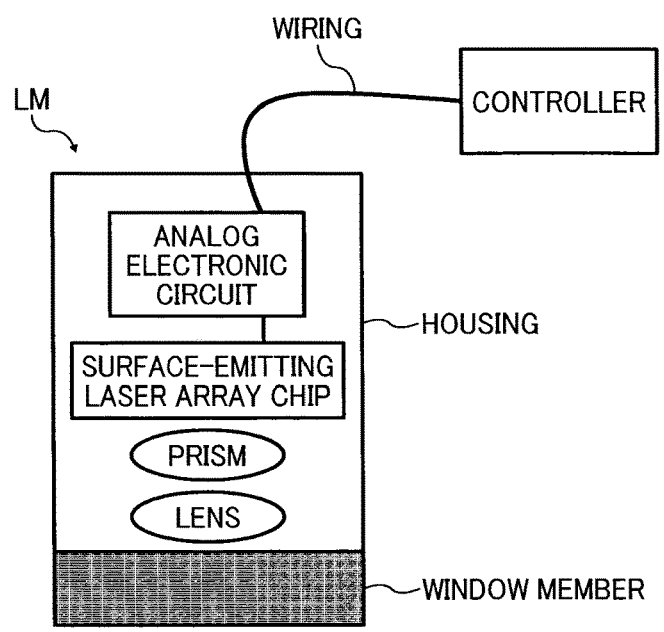
FIG. 4 is a first diagram illustrating an outline of the configuration of a light source module according to the first example of the first embodiment of the present invention.

As illustrated in FIG. 4, the light source module LM includes, for example, a lens, a prism, a ceramic package on which a surface-emitting laser array chip is mounted, a flexible circuit board on which the ceramic package and an analog electronic circuit are mounted, a wiring connected to the flexible circuit board, a connector, a housing accommodating these elements, and a housing accommodating these elements, and a window member consisting of transparent resin that contacts the test object. The light source module LM can maintain the amount of the light emitted from the light-emitting units at a constant light quantity as the current value is controlled to an appropriate value by a power source unit. The light source module LM is attached to each of the transparent windows B such that a window member contacts the test object (transparent window B) from the +Z side.

Figure 5:
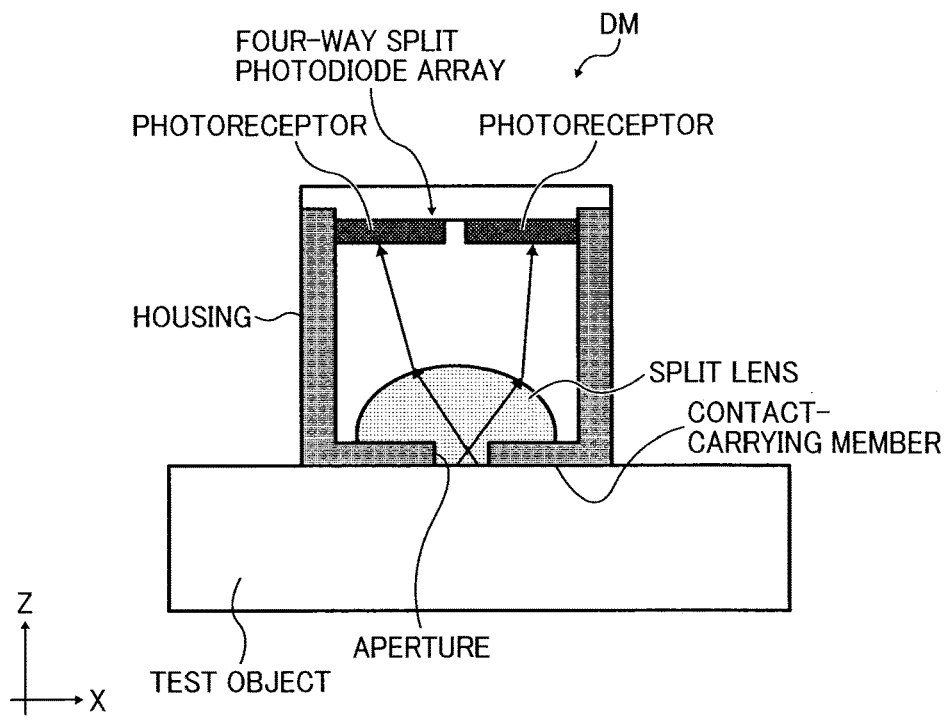
FIG. 5 is a first diagram illustrating an outline of the configuration of a detection module according to the first example of the first embodiment.

As illustrated in FIG. 5, the detection module DM includes a black-resin housing, a contact-carrying member consisting of an elastic body attached to a front end of the housing (i.e., the end on the −Z side), a 3.0 mm hemispheric lens (split lens) in diameter accommodated in the housing, and a four-way split photodiode array (an array of four photodiodes). The housing has apertures at the front end of the housing and at the other end of the housing in contact with the contact-carrying member. The detection module DM is attached to each of the transparent windows A such that the contact-carrying member contacts the test object (transparent window A) from the +Z side. Note that in FIG. 5, only two of the four photodiodes (photoreceptors) are illustrated.

The split lens is arranged in the proximity of the aperture on the +Z side. Due to this configuration, the light that is emitted from the light source module LM to the test object and then propagates inside the test object enters the split lens through the aperture, and is refracted and exited according to the position at which the light enters the split lens and the direction in which the light enters (see FIG. 5).

The four-way split photodiode array is arranged on the +Z-side of the split lens. Then, the light that has passed through the split lens enters one of the four photoreceptors (photodiodes) of the four-way split photodiode array according to the direction of travel (i.e., the light exit direction from the split lens). As described above, the detection module DM can classify the incident angles at which the light exiting from the test object enters the detection module DM into four ranges of angle.

The controller detects the amount of the light received by the four photodiodes (photoreceptor) of the detection module DM attached to each of the transparent windows A (the amount of the light received by sixteen photodiodes in total), and converts the detected amount of light into voltage using an operational amplifier. Then, the controller stores the obtained value of voltage in the storage unit. The data is obtained at the sampling rate of 1 millisecond (msec), and the values obtained in the measurement in 20 seconds (sec) are averaged. In one-time measurement, the data of the sixteen photodiodes is obtained.

Next, the light source module LM is described in detail. As the light source of the light source module LM, a 40-channel surface-emitting laser array chip is adopted. More specifically, a surface-emitting laser array chip provided with forty vertical-cavity surface-emitting lasers (VCSEL) as light-emitting units is adopted as the light source of the light source module LM.

Figure 6:
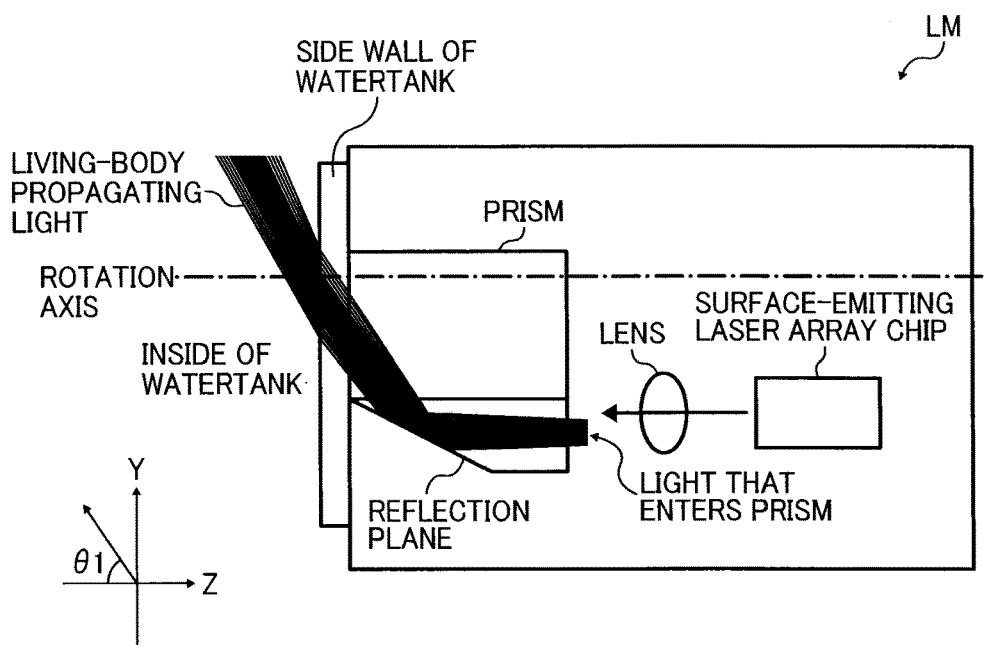
FIG. 6 is a second diagram illustrating an outline of the configuration of a light source module according to the first example of the first embodiment of the present invention.
Figure 7A:
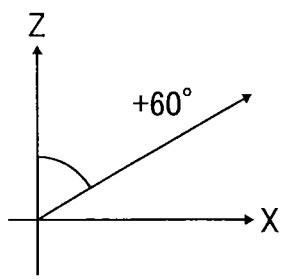
FIG. 7A to FIG. 7D illustrate the propagation angle inside the living body according to the first embodiment of the present invention.
Figure 7B:
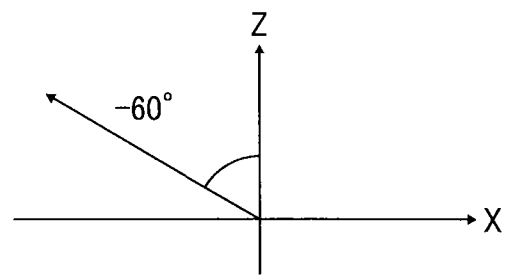
Figure 7C:
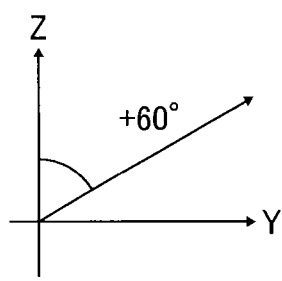
Figure 7D:
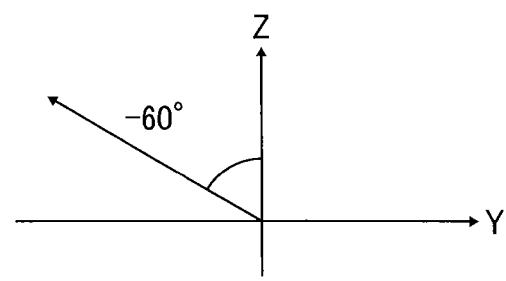

In the optical path of the light emitted from the surface-emitting laser array chip, a 3 mm lens in diameter that approximately collimates the light is arranged (see FIG. 6). The distance between the exit plane (light-emitting surface) of the surface-emitting laser array chip and the principal point (optical center of the lens) is designed to be equal to the focal length f (for example, 9 mm) of the lens. In other words, the surface-emitting laser array chip is arranged such that the exit plane is disposed at the focal point of the lens. Note that "the focal length of the lens" indicates the distance between the principal point and the focal point of the lens.

In the present example, 40 channels are switched on at the same time, and the total output is about 50 milliwatt (mW). As illustrated in FIG. 6, the parallel light emitted from the VCSEL is deflected by the prism.

As the prism, an acrylic prism whose refractive index is equivalent to that of the acrylic watertank as described above is adopted. The reflection plane of the prism is designed in accordance with the diameter of the prism, and the angle of the reflection plane is arranged such that the light that has passed through the lens enters the acrylic watertank at the incident angle of about 50 degrees.

The difference in refractive index between the phantom (intralipid aqueous solution) and the acryl of the watertank and the prism is designed such that the propagation angle in the phantom becomes about 60 degree (Olin FIG. 6) according to the Snell laws of reflection. The prism is attached to a rotatable stage disposed on the inner wall of the watertank. The rotatable stage rotates around the rotation axis that extends in the Z-axis direction.

As the rotatable stage and prism rotate together, the incident angle and direction of the light that enters the prism can be changed. FIG. 7A to FIG. 7D illustrate the propagation angle inside the living body according to the present embodiment. In the present example, as illustrated in FIG. 7A to FIG. 7D, the measurement is sequentially performed in the four directions including the +X, −Y, +Y, and −Y directions. Accordingly, the measurement is performed for the four positions of the four light source modules LM (B1 to B4) and for the four directions. As a result, the measurement is performed sixteen times in total. In between the prism and the watertank, gel-like resin with the refractive index equivalent to that of the prism and the watertank is filled. Accordingly, the refraction or reflection between the prism and the watertank can be prevented.

Figure 8:
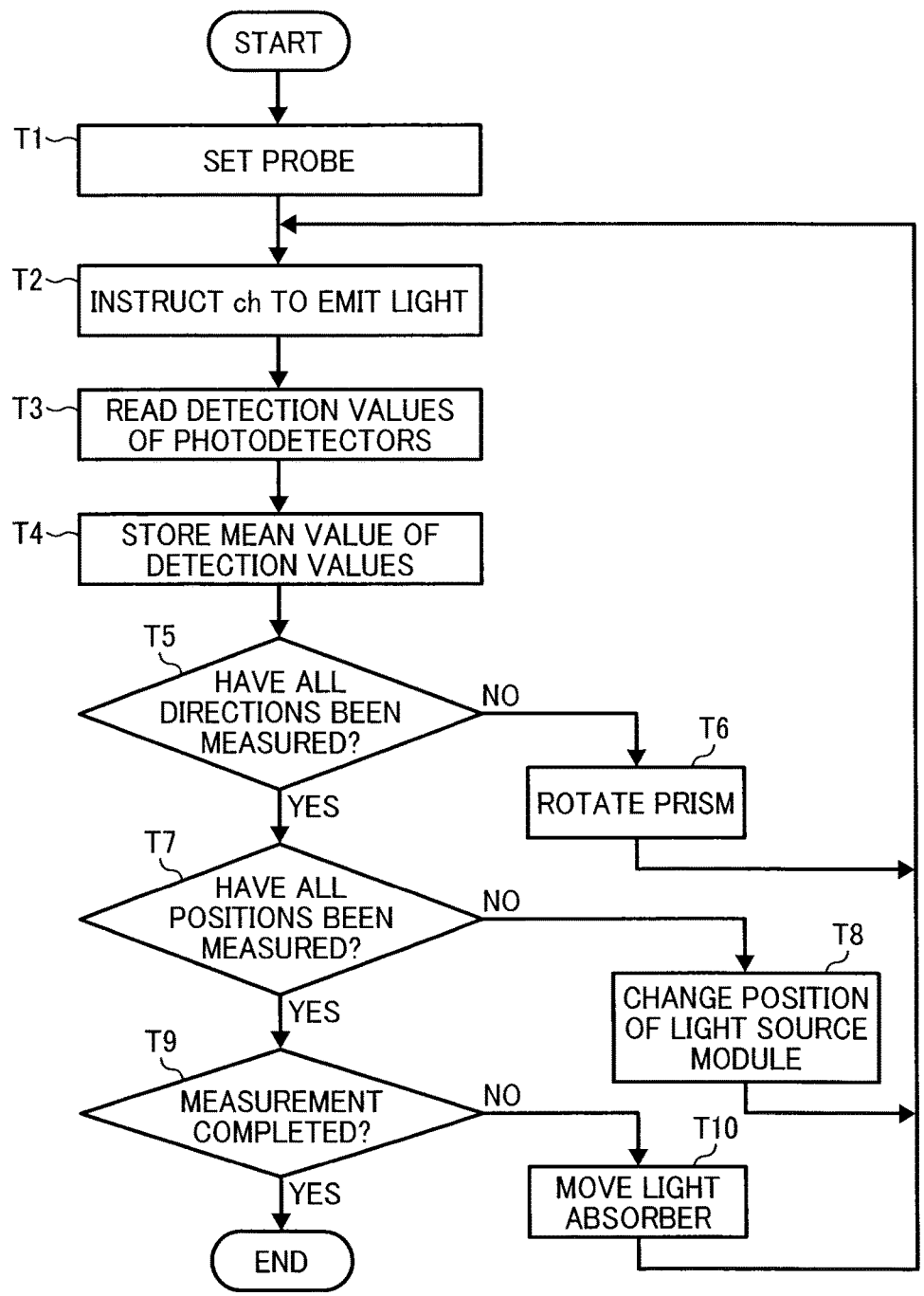
FIG. 8 is a flowchart of a method of measuring the data inside the test object according to the first embodiment of the present invention.
Figure 9:
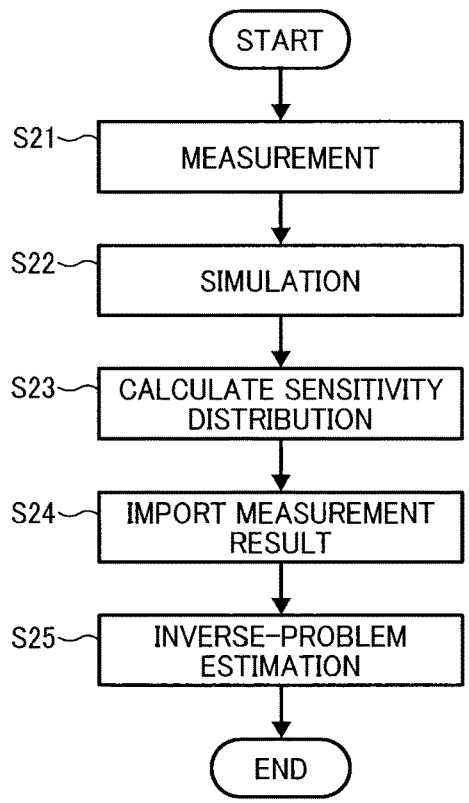
FIG. 9 is a flowchart of an inverse-problem estimation algorithm according to the first embodiment of the present invention.

FIG. 8 is a flowchart of a method of measuring the data inside the test object according to the first embodiment of the present invention. Next, a method of measuring the data inside the test object is described below with reference to the flowchart of FIG. 8.

Firstly, a probe is set (step T1). As described above, the probe indicates the detection module DM and the light source module LM. Here, the probe to be set includes four detection modules DM and one light source module LM. The four detection modules DM are attached to each of the four 9 mm transparent windows A in diameter as illustrated in FIG. 3. The one light source module LM is attached to the transparent window B1 as illustrated in FIG. 3.

Next, the forty channels (light-emitting units) of the light source module LM are instructed to emit light at the same time (step T2). The light-emission intensity is determined such that the current value becomes about 50 milliwatt (mW) in total. The light emitting period is about 20 seconds (sec), and the detection values of the four photodiodes of the detection module DM are read during the light emitting period (step T3). The pieces of data (detection values) obtained at 1 millisecond (msec) intervals are averaged. Then, the averaged detection values, i.e., the mean value of detection values, is stored in the storage unit (step T4).

In the present example, the measurement is performed for the four directions including the +X direction, +Y direction, −X direction, and −Y direction (steps T5 and T6). More specifically, the steps T2 to T4 immediately after the step T1 are performed upon arranging the prism in the +X direction. Next, the prism is rotated to the +Y direction (step T6). In this state, the steps T2 to T4 are repeated. Next, the prism is rotated to the −X direction (step T6). In this state, the steps T2 to T4 are repeated. Next, the prism is rotated to the −Y direction (step T6). In this state, the steps T2 to T4 are repeated.

Next, the position where the light source module LM is attached is sequentially changed from the transparent window B1 to the transparent windows B2, B3, and B4, and the measurement is performed again for the four directions (steps T7 and T8). Then, the position of the light absorber is shifted, and the measurement is performed again for the four directions and the four positions where the light source module LM is attached (steps T9 and T10).

The stored data is labeled as $r(s, i, n)$ ($i=1, 2, 3, \ldots M$; $n=1, 2, 3, \ldots K$) with the light absorber and $r(0, i, n)$ ($i=1, 2, 3, \ldots, M$; $n=1, 2, 3, \ldots, K$) without the light absorber. "i" denotes the numbers assigned to the respective detection modules DM. "n" denotes the numbers assigned to the respective groups. Next, the difference $\Delta r(i, n)$ is calculated.

Figure 47:
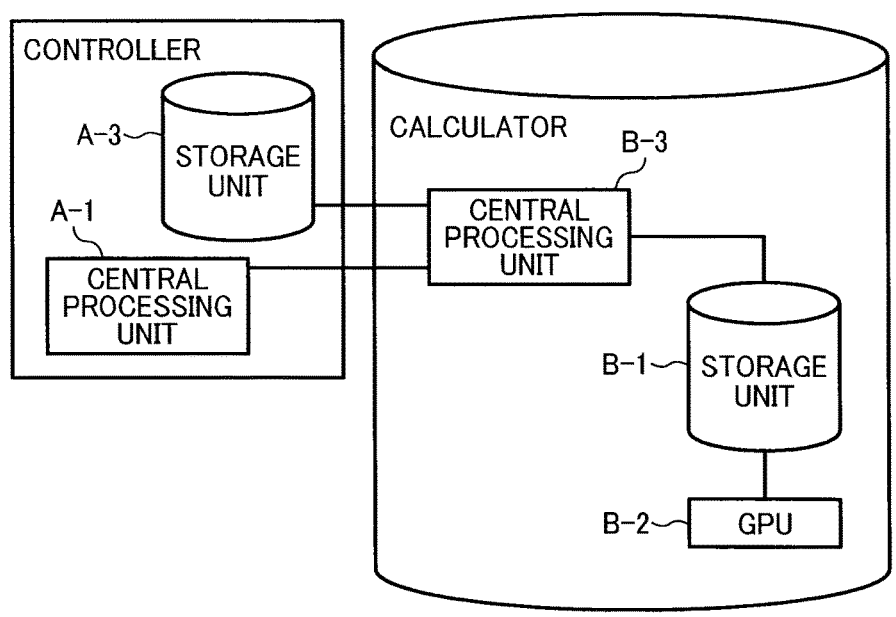
FIG. 47 is a block diagram illustrating the configuration of a calculator according to the embodiments of the present invention.

Next, a method of calculating the position of the light absorber (the optical property of the pseudo living body) according to the result of the measurement obtained by the measurement method as depicted in the flowchart of FIG. 8 is described. In this method, an inverse-problem estimation algorithm is adopted. In order to solve an inverse problem, firstly, measurement and simulation are performed and a sensitivity distribution is calculated using a forward problem. Then, the data obtained by the subsequent measurement is imported, and an inverse problem estimation is performed based on the value in the imported data (see steps S21 to S25 in FIG. 9). FIG. 47 is a block diagram of the calculator. Data such as that of the position of the modules (probes) and the refractive index or shape of the living body, which is used for the Monte Carlo simulation as will be described later, is stored in the storage unit B-1. The above-mentioned forward problem is performed based on this data. In the calculation of this forward problem, a graphics processing unit (GPU)

(multigraphics processor) capable of parallel computation is used. The use of such a GPU dramatically speeds up the calculation compared with the conventional computation speed. The sensitivity distribution obtained by this calculation is stored again in the storage unit B-1. This calculation result and the measurement result stored in the storage unit A-3 are input to the central processing unit B-3, and the central processing unit B-3 performs the inverse problem estimation. The estimation result is displayed on the display unit through the central processing unit A-1 (see FIG. 46).

Conventionally, in the forward problem calculation, it was believed that the light in a scatterer such as a living body disperses in an almost isotropic manner. For this reason, a simulation using a diffusion equation with less computational complexity has been adopted. In recent years, however, it has been reported, for example, in academic conferences, that the light propagation in a minute area of a few millimeters is in fact anisotropic in a living body. In order to perform a simulation in view of such anisotropy, a transport equation or the Monte Carlo simulation is performed.

In the present embodiment, the light emitted from the light source is deflected so as to enter the test object. For this reason, a diffusion equation known in the art is not sufficient to perform a simulation in view of the data of the incident angle. A method in which a transport equation is used has been suggested. However, it is known in the art that a method in which a transport equation is used takes an enormous length of time.

In order to deal with such situation, the Monte Carlo simulation is adopted in the present in the present embodiment. The Monte Carlo simulation is a method in which the condition for the photons to disperse in a scattering medium are stochastically expressed by a random variable and the macroscopic behavior of the photons is observed. More specifically, the behavior of the photons is modeled with the assumption that the photons move in a medium and collision occurs every time the photons travel a certain distance and that the directivity of the photons changes accordingly. The average distance traveled by the photon in the above model is the mean free path, and the mean free path is defined by a scattering coefficient. The changes in direction are defined by the anisotropy g. The repeated collisions and how the photon propagates in a specified area are recorded. By calculating a myriad of photons in the model as described above, the behavior of the light in the scattering medium can be simulated. By the Monte Carlo simulation, the path of the dispersion of one photon is recorded.

In the Monte Carlo simulation according to the present embodiment, a 120 mm×120 mm×60 mm three-dimensional area is calculated where the number of the photons is $10^9$ and the voxel is a 1 mm cube. In the present embodiment, the scattering coefficient, absorption coefficient, anisotropy, and the refractive index of the scattering medium are 7.8 $mm^{-1}$, 0.019 $mm^{-1}$, 0.89, and 1.37, respectively, and these values are almost equivalent to the scattering coefficient, absorption coefficient, anisotropy, and the refractive index of a scalp. The above-described phantom (intralipid aqueous solution) is prepared to meet these values, and a simulation is performed under the same situations as those of the phantom with all aspects such as the propagation angle and the positions of the light source module LM and the detection module DM to calculate a sensitivity distribution.

In this simulation and calculation, it is assumed that the number of the photons that have passed through the position r of the voxel is $\varphi_0(r)$. In particular, it is assumed that the number of the photons that have passed through the position r of the voxel where the position of the light source module LM is "rs" is $\varphi_0(rs, r)$. Next, the light source module LM is disposed at the position where the detection module DM was disposed. Then, the same number of photons are calculated again. When the detection module DM is disposed at "rd", it is assumed that the number of the photons that have passed through the position of the voxel is $\varphi_0(r, rd)$.

As the optical path is reversible, this product is proportional to the number of the photons that pave passed through the position r of the voxel, emitted from the light source module LM, and have entered the detection module DM. The product is normalized by the number $\varphi_0(rs, rd)$ of all the photons that enter the detection module DM. As a result, the following sensitivity distribution A(r) is obtained.

$$A(r) = \frac{\phi_0(rs, r)\phi_0(r, rd)}{\phi_0(rs, rd)} \quad \text{[Formula 1]}$$

The sensitivity distribution A(r) indicates the degree of influence on the amount of detection at the position r. The sensitivity distribution A(r) indicates how much the detection value changes due to the presence of a light absorber at the position r of the voxel.

Figure 10:
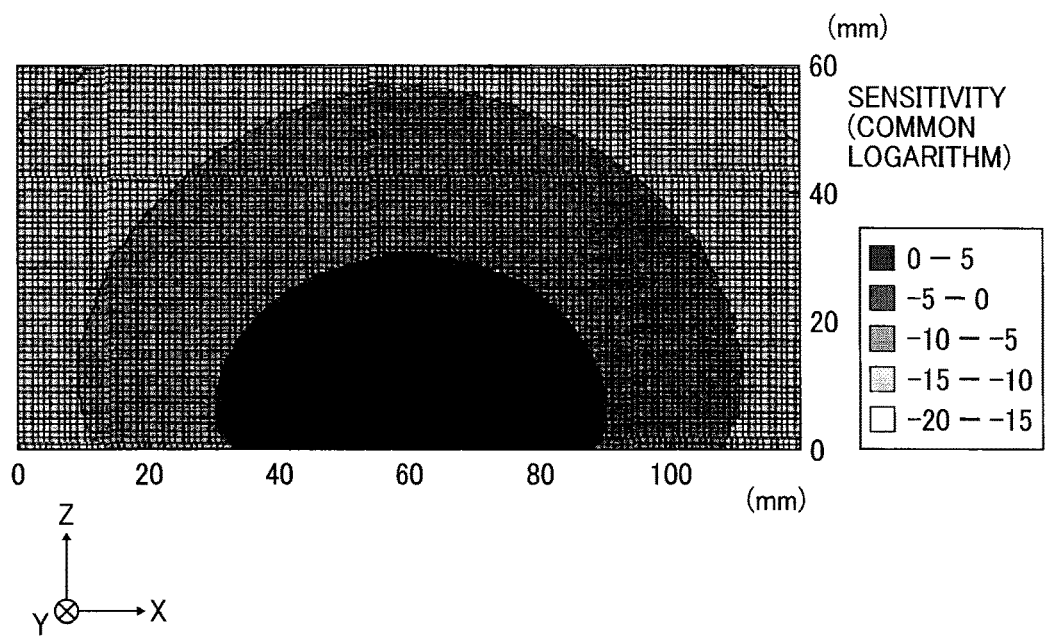
FIG. 10 is a first diagram illustrating the sensitivity distribution at a photodiode, according to the first embodiment of the present invention.

FIG. 10 is a first diagram illustrating the sensitivity distribution at a photodiode, according to the first embodiment of the present invention. An example of the sensitivity distribution calculated as above is illustrated in FIG. 10. In FIG. 10, the light source module LM and the detection module DM are disposed at (X, Y, Z)=(45, 60, 0) and (X, Y, Z)=(75, 60, 0), respectively. As the voxel is a 1 mm cube, the measurement unit is equivalent to that of these values. The sensitivity of the voxel at each position is indicated by the base 10 logarithm (common logarithm) base.

Figure 11:
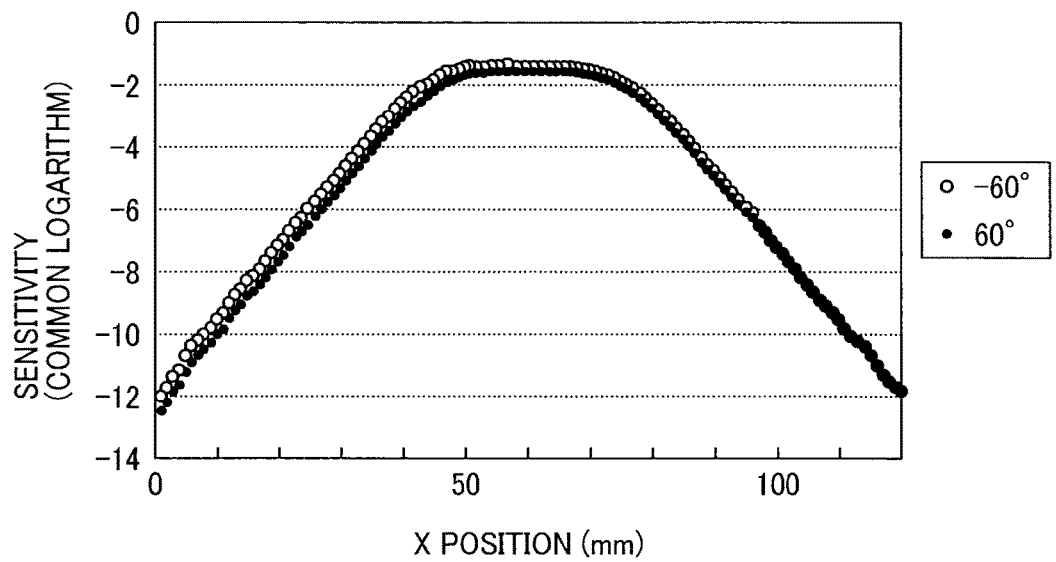
FIG. 11 is a second diagram illustrating the sensitivity distribution at a photodiode, according to the first embodiment of the present invention.
Figures 12A, 12B:
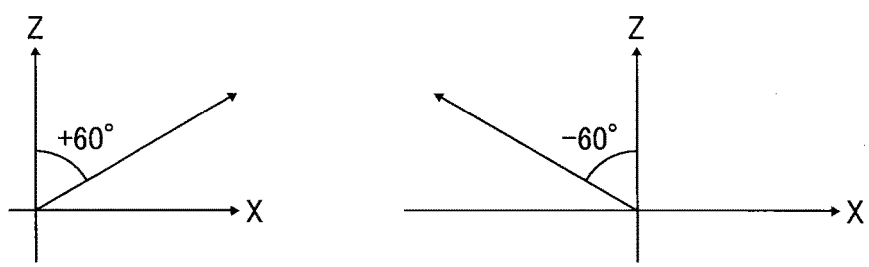
FIG. 12A and FIG. 12B illustrate the propagation angle inside the living body according to the first embodiment.

FIG. 11 is a second diagram illustrating the sensitivity distribution at a photodiode, according to the first embodiment of the present invention. Next, the line with Y=60 and Z=10 of the voxel (x, y, z) is extracted from the sensitivity distribution illustrated in FIG. 10. Then, the extracted line is plotted where the vertical axis and the horizontal axis indicate the sensitivity and the x position, respectively. The result of such extraction and plotting is illustrated in FIG. 11. FIG. 12A and FIG. 12B each illustrate the propagation angle inside the living body according to the first embodiment. More specifically, FIG. 12A and FIG. 12B illustrate the propagation angles inside the living body when the angle which the light forms with the X-axis on the plane where the Y-axis is the normal line is +60 degrees and −60 degrees, respectively.

As illustrated in FIG. 11, there are differences in the sensitivity distribution between the case of +60 degrees and the case of −60 degrees. Such differences serve as a guiding principle to determine whether the improvement in resolution becomes possible. In other words, the presence of a difference between these two sensitivity distributions indicate that the propagation paths of the rays of light emitted from two light sources are different from each other. If the propagation paths are same, the sensitivity distributions should be same as well even if the propagation angle varies. As the propagation paths from the two light sources are different from each other, the rays of light from the two light sources collect different data.

This fact is significant for the inverse problem estimation as will be described later. As described above, the propagation of light is not simple isotropic scattering, but is slightly anisotropic of the order of several millimeters. It is considered that such a difference of the order of several millimeters becomes a factor in achieving inverse problem estimation with the resolution of the order of several millimeters. Such a sensitivity distribution is to be calculated for all the propagation angles and detection angles of all the light source modules LM and detection modules DM in the phantom.

Next, the sensitivity distribution is used to perform inverse problem estimation.

Assuming that the change $\delta\mu_a(r)$ in absorption coefficient caused by a light absorber is sufficiently small, the following equation holds true due to the approximation of Retov.

$$\log \frac{\phi_0(rs, rd)}{\phi(rs, rd)} = \frac{v}{s} \frac{\int \vec{dr} \, \phi_0(rs, r)\delta\mu_a(r)\phi_0(r, rd)}{\phi_0(rs, rd)} \quad \text{[Formula 2]}$$

v denotes the velocity of light in a medium, and S denotes the amount of the light emitted from the light source module LM per unit time. rs denotes the position of the light source module LM, and rd denotes the position of the detection module DM. $\varphi(rs, rd)$ indicates the amounts of the light that is received by the detection module DM after being emitted from the light source module LM, and $\varphi_0$ indicates the light intensity on condition that a light absorber is absent. This formula indicates that when the light intensity $\varphi_0$ is given in the absence of the light absorber, a linear correlation is established between the observed value log $\varphi(rs, rd)$ and the change $\delta\mu_a(r)$ in the absorption coefficient caused by the light absorber.

This may be simplified in the equation as follows.

$$Y = A(r)X$$

In this equation, Y denotes the change in the observed value due to the presence or absence of the light absorber, and X denotes the change in the absorption coefficient at the position r of the voxel. Moreover, A(r) indicates the sensitivity distribution. The above equation indicates how the observed value Y changes due to the change in the position or amount of the light absorber indicated by X. In an inverse problem estimation, calculation the other way around is performed. In other words, the position X of the light absorber is estimated using the observed value Y. As described above with respect to the position measuring method, measurement is performed upon assuming that the change due to the presence or absence of the light absorber is the difference $\Delta r$ (i, n). This difference $\Delta r$ (i, n) is used as the observed value Y to calculate X.

As known in the art, an estimation method for a reverse problem called L2 norm regularization is used for the above calculation. In this method, X that minimizes the cost function C as given below is calculated.

$$C = |Y - AX|^2 + \lambda |X^2| \quad \text{[Formula 3]}$$

In the Formula 3, Y, A, and $\lambda$ indicate the observed value, the sensitivity distribution, and the regularized coefficient, respectively. In the inverse problem estimation, the above method is commonly adopted. However, in the present embodiment, the Bayes estimation that can also detect the depth direction is used to perform an inverse problem estimation. For the detail of the inverse problem estimation using the Bayes estimation, see "T. Shimokawa, T. Kosaka, O. Yamashita, N. Hiroe, T. Amita, Y. Inoue, and M. Sato, "Hierarchical Bayesian estimation improves depth accuracy and spatial resolution of diffuse optical tomography, "Opt. Express*20*, 20427-20446(2012)".

Figure 13A:
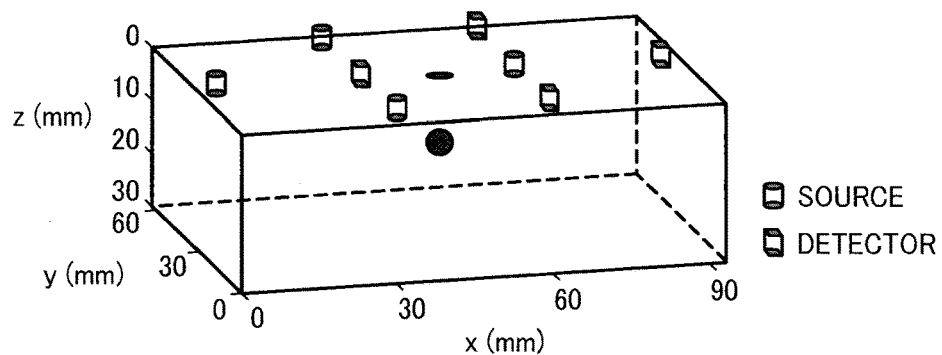
FIG. 13A illustrates the actual position of the light absorber according to the first embodiment.
Figure 13B:
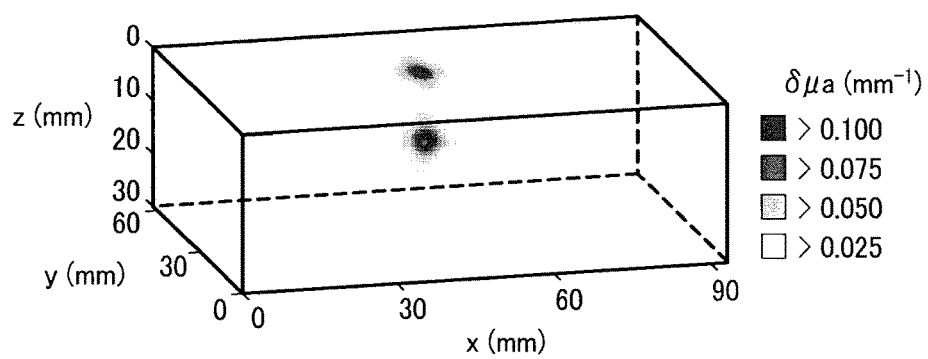
FIG. 13B illustrates the result of estimation of the position of the light absorber according to the first embodiment.
Figure 13C:
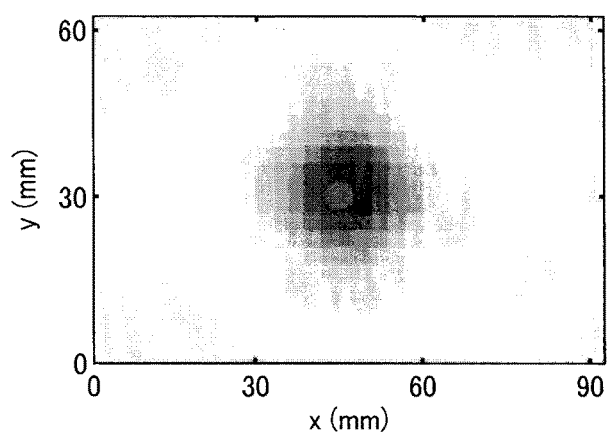
FIG. 13C illustrates the result of the detection of the position of the light absorber according to a control sample.

FIG. 13A illustrates the actual position of the light absorber according to the present embodiment. FIG. 13B illustrates the result of estimation of the position of the light absorber according to the present embodiment. FIG. 13C illustrates the result of the detection of the position of the light absorber according to a control sample. As a result, the result of estimation as illustrated in FIG. 13B can be obtained. The grid in FIG. 13B has 3 mm patterns, and the actual position can be obtained with 3 mm precision.

As a control sample, the result of detection where one of the four orientations is used is illustrated in FIG. 13C. The configuration of this control sample is almost equivalent to that of the conventional near-infrared spectroscopy (NIRS) DOT device. In the control sample, it is not possible to detect the depth direction, and the detection result becomes very much dispersed. By contrast, in the first example of the present embodiment, the Bayes estimation is adopted as described above, and both the position and depth of the light absorber are detectable.

Figure 14A:
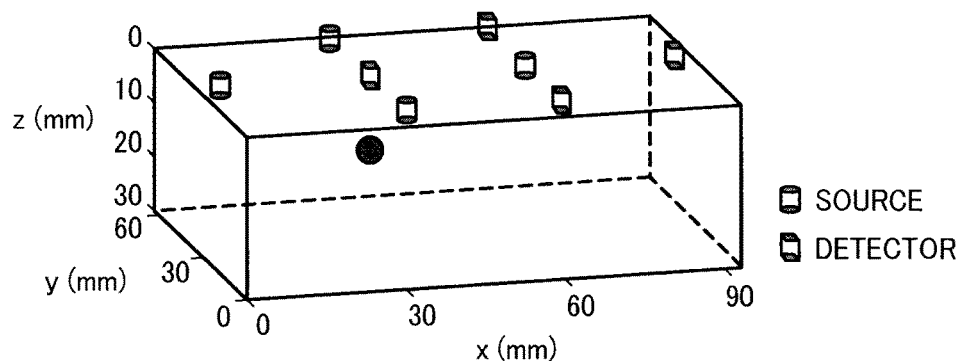
FIG. 14A illustrates the actual position of a light absorber after movement, according to the first embodiment of the present invention.
Figure 14B:
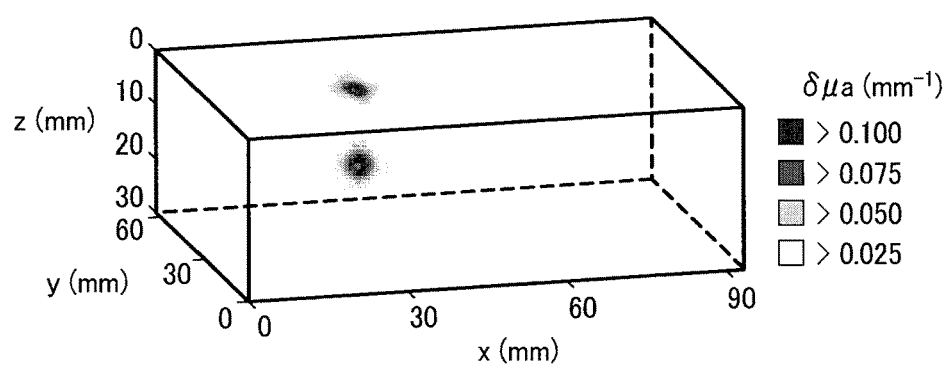
FIG. 14B illustrates the result of estimation of the position of a light absorber after movement, according to the first embodiment of the present invention.
Figure 14C:
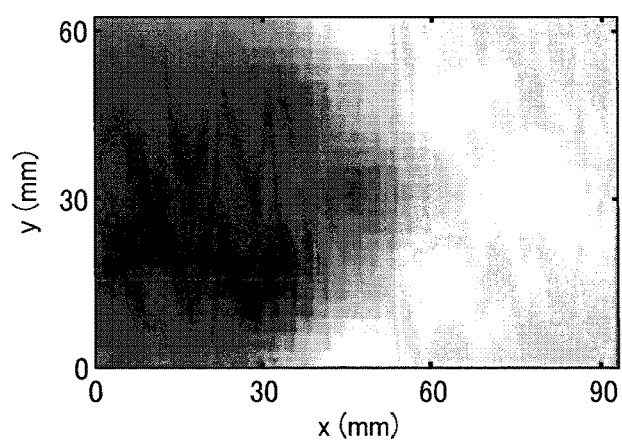
FIG. 14C illustrates the result of the detection of the position of a light absorber, according to a control sample.

FIG. 14A illustrates the actual position of a light absorber after movement, according to the first embodiment of the present invention. FIG. 14B illustrates the result of estimation of the position of a light absorber after movement, according to the first embodiment of the present invention. FIG. 14C illustrates the result of the detection of the position of the light absorber according to a control sample. The position of the light absorber is changed as illustrated in FIG. 14A, and the estimation of the position is performed as illustrated in FIG. 14B. Even after the light absorber is moved, the actual position of the light absorber is precisely estimated. As the method in the first example is adopted, the position of the light absorber is detectable with high resolution. By contrast, in the control sample, the image of the light absorber is very much dispersed as illustrated in FIG. 14C, and it is not possible to detect the position of the light absorber with accuracy.

Next, a second example of the present embodiment is described below. Note that the second example will be described in relation to the first example as necessary.

Second Example

Firstly, black ink is dripped into the intralipid aqueous solution filled in the acrylic transparent watertank to the degree of about 200 ppm, where the intralipid aqueous solution is obtained by diluting 10 percent intralipid ten times thinner. Accordingly, the absorption coefficient and scattering coefficient that are almost equivalent to those of a living body can be achieved. Then, a black light absorber simulating bloodstream is sunk into the whitish intralipid aqueous solution. In the present example, the light absorber is, for example, black polyacetal, and has an approximately 5 mm spherical body in diameter. In order to control the position of such a spherical body, the spherical body is attached to a thin 1 mm metallic rod in diameter, and the rod is connected to an automatic positioning stage. A probe is precisely aligned to a side of the watertank, and is attached thereto. In the present example, the acrylic watertank has a rectangular-parallelepiped shape with the volume of, for example, 140 mm×140 mm×600 mm, where thickness of the wall is 1 mm.

The optical sensor 10 includes an irradiation system including a plurality of (for example, eight) light source modules LM, and a detection system including a plurality of (for example, eight) detection modules DM. Each of the light source modules LM and the detection modules DM is connected to the controller through the electrical wiring.

The controller controls the timing of light emission at the light sources of the light source modules LM or the timing of detection at the detection modules DM, and transfers the obtained detection results to the storage unit. Moreover, the controller reads the data stored in the storage unit and perform calculation using the values of the read data, and controls the display unit to display the calculation result thereon.

Figure 15:
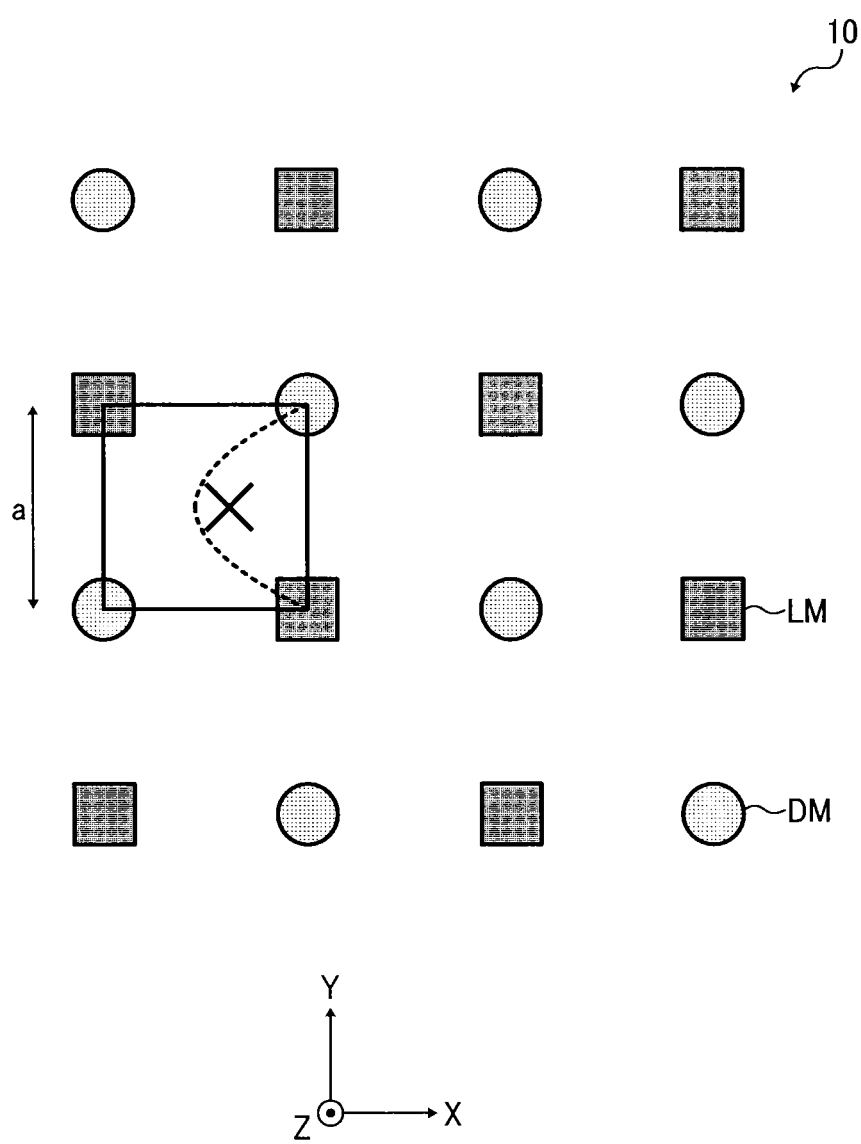
FIG. 15 is a diagram illustrating the arrangement of a plurality of light source modules and a plurality of detection modules in an optical sensor according to the second example.

FIG. 15 is a diagram illustrating the arrangement of the light source modules LM and the detection modules DM in the optical sensor 10 according to the second example. As illustrated in FIG. 15 for example, the eight light source modules LM and the eight detection modules DM are arranged for a pseudo living body in a four-by-four matrix (two-dimensional grid pattern) in the X direction and the Y direction with equal pitches, such that the light source module M and the detection module DM are next to each other in both the X direction and the Y direction that are orthogonal to each other. In FIG. 15, the rectangular signs denote the LM, and the circular signs denote the DM.

Figure 16:
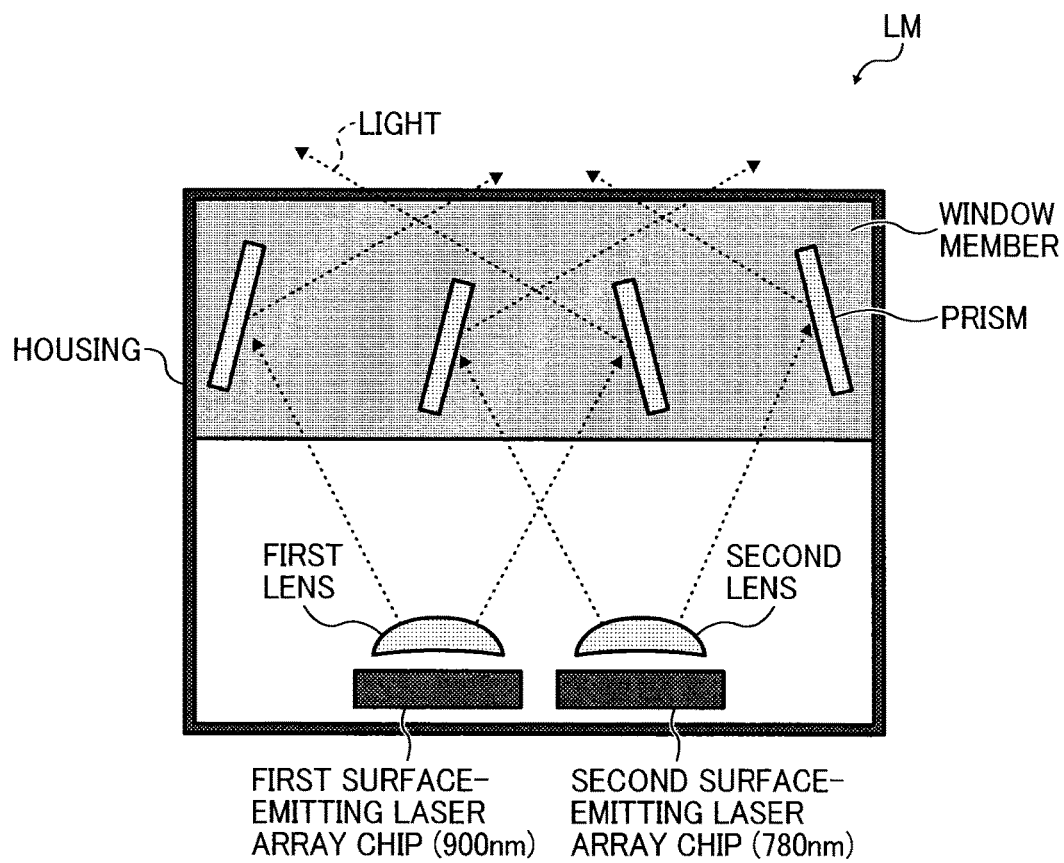
FIG. 16 is a diagram illustrating a light source module LM according to the second example.
Figure 16:
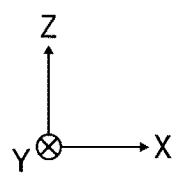

FIG. 16 is a diagram illustrating a light source module LM according to the second example. As illustrated in FIG. 16, the light source module LM includes, for example, an optical element such as a lens and a prism, a ceramic package on which a plurality of surface-emitting laser array chip are mounted, a flexible circuit board on which the ceramic package and an analog electronic circuit are mounted, a wiring connected to the flexible circuit board, a connector, a housing accommodating these elements, a window member consisting of transparent resin that contacts the test object.

The oscillation wavelength of the surface emitting lasers (VCSEL) of the surface-emitting laser array chip is, for example, 780 nanometer (nm) or 900 nm. These wavelengths are selected in view of the fact that the absorption coefficient varies widely according to the oxygen concentration in the blood. As illustrated in FIG. 16, in the light source module LM, a first surface-emitting laser array chip with the oscillation wavelength of 900 nm and a second surface-emitting laser array chip with the oscillation wavelength of 780 nm are arranged in parallel with each other. Moreover, a first lens is disposed in the proximity of the exit end of the first surface-emitting laser array chip, and a second lens is disposed in the proximity of the exit end of the second surface-emitting laser array chip. In the following description, the surface emitting lasers may be referred to as channels (ch).

The rays of light emitted from the surface-emitting laser array chips are refracted by the corresponding lenses, and deflected (reflected) to a desired angle by the prisms that are formed inside the window member and exited to the outside of the housing. In the present example, the prism serves as a reflection member.

Figure 17:
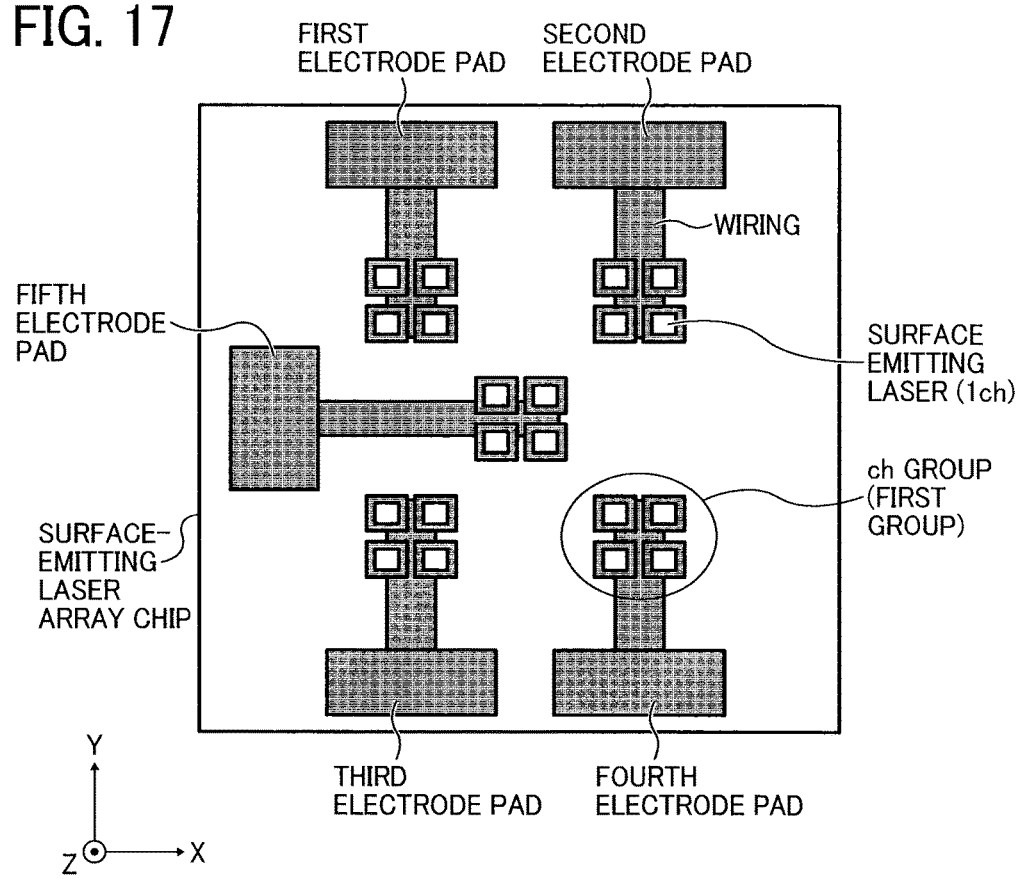
FIG. 17 is a diagram illustrating a surface-emitting laser array chip of the light source module LM according to the second example.

FIG. 17 is a diagram illustrating a surface-emitting laser array chip of the light source module LM according to the second example. As illustrated in FIG. 17, the surface-emitting laser array chip has a square shape with the sides of about 1 mm, and includes a plurality of (for example, twenty) two-dimensionally disposed surface emitting lasers.

More specifically, each of the surface-emitting laser array chips includes five groups (channel (ch) groups) each of which includes four surface emitting lasers. In the present example, the centers of the four groups among the five groups are disposed separately at the four vertices of the square, and the center of the remaining one group is disposed at the center of the square.

As described above, the four channels of each group are mounted on the ceramic package, and are connected to the same electrode pad (i.e., one of the first to forth electrode pads) through the bonding wire (wiring).

The ceramic package is implemented by being soldered onto the wiring pattern of the flexible circuit board. On the flexible circuit board, a semiconductor for switching or a semiconductor for stabilizing the current are attached. The semiconductor for switching controls which channel of the surface-emitting laser array chip is to emit light. The semiconductor for switching controls the selected channel to emit light according to the externally given serial signal. One end of the signal line for the serial signal and one end of the power supply line are connected to the flexible circuit board, and the other end of the signal line and the other end of the power supply line are connected to the controller.

The amount of the light emission of each channel is calibrated constant at regular intervals. Under normal conditions, the five groups are controlled to emit light in sequence with short pulses. As the temperature rise due to heat liberation can be avoided, such pulse light emission is suitable for stabilizing the amount of the light emission. The detection values obtained every time light is emitted with short pulses by the detection module are added up and then averaged. By so doing, the detection becomes resistant to the noise.

Next, the reason why the surface-emitting laser array chip is adopted as the light source of the optical sensor 10 is described. In the surface-emitting laser array chip, the multiple channels can two-dimensionally be arranged in close proximity to each other, and the light emission of the channels can be controlled in an in an independent manner. Further, the path of the exit light can be changed by disposing a small lens in the proximity of the channels.

For optical sensors provided for the DOT, precise control of the incident angle to the test object is required. As commonly-used light-emitting diodes (LED) have a wide angle of departure, a lens needs to have an aspherical surface in order to achieve collimated beam with high accuracy. Moreover, a commonly-used laser diode (LD) (end-surface emitting laser) has an asymmetrical angle of departure. For this reason, in order to achieve collimated beam with high accuracy, two lenses such as lenses with varying curvatures in length and breadth or cylindrical lenses need to be combined. Such a configuration is complicated, and advanced implementation is required.

By contrast, a surface emitting laser has an almost perfectly circular far field pattern, and only one spherical lens needs to be disposed to form a collimated beam. When the coherent light emitted from the LD is used, speckles occur in the test object (scatterer) and the scattered lights interfere with each other. Such a speckle pattern affects the measurement as a noise.

When the bloodstream inside the brain is observed, for example, by the DOT, a very large number of scatterings occur. For this reason, when the bloodstream inside the brain is observed, the measurement is not very much affected by a speckle pattern. However, the measurement is still affected by a return light where the light reflected by the surface of the skin directly returns to the light source. Such a return light may make the oscillation state inside the LD unstable, and in such a case, the stable operation is disabled. When coherent light is to be used in a stable manner, for example, in an optical disk, a wave plate or the like is used such that a specular reflection light does not become a return light. However, it is difficult to remove a return light of the reflection light from the scatterer.

In the case of a surface-emitting laser array chip, a plurality of rays of light can simultaneously be emitted to a minute area, and the interference of the return light can be reduced (see, for example, JP-2012-127937-A).

Figure 18:
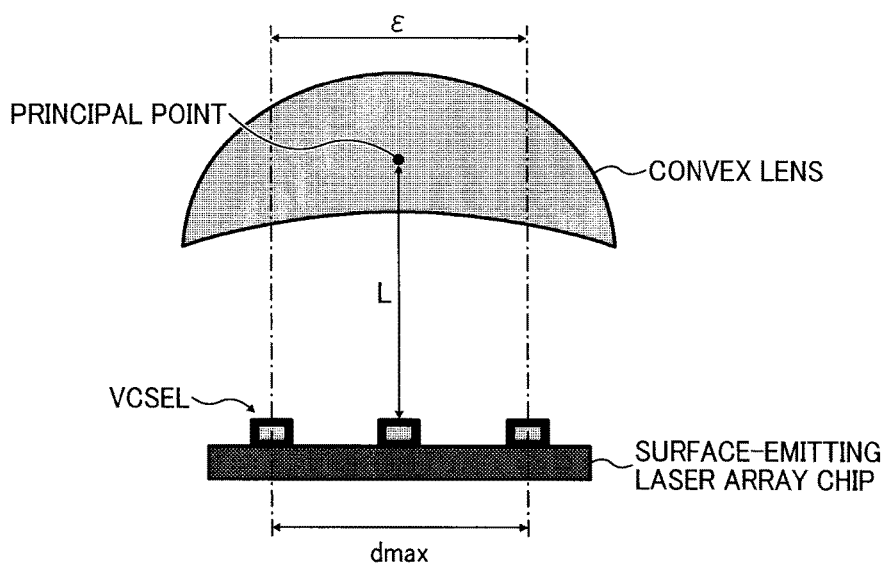
FIG. 18 illustrates a first additional configuration of the light source module according to the first and second examples of the first embodiment of the present invention.

FIG. 18 illustrates a first additional configuration of the light source module according to the first and second examples of the first embodiment of the present invention. In the present embodiment (the first and second examples), a convex lens is arranged on the optical path of the light emitted from the surface-emitting laser array chip (see FIG. 18). This convex lens may be referred to simply as a lens in the following description.

This convex lens has the 1 mm diameter, and has the 600 micrometer (μm) effective diameter c. Moreover, the focal length f of the convex lens is 600 μm. The surface-emitting laser array chip is a chip with 1 mm angles, and The distance dmax between the centers of the two most distant channels in the surface-emitting laser array chip is 600 As described above, by matching the dmax and the effective diameter ε, the diameter of the convex lens can be minimized.

In the present embodiment, the convex lens and the surface-emitting laser array chip are registered such that the distance L between the principal point (optical center) of the convex lens and the light-emitting surface (exit plane) of the surface-emitting laser array chip in the optical-axis direction of the convex lens becomes, for example, 300 μm. That is, f≠L.

In this configuration, a phenomenon (return light phenomenon) can be avoided in which the light emitted from the surface-emitting laser array chip and passed through the convex lens is reflected by a prism or the like by specular reflection and then is concentrated onto the surface-emitting laser array chip. As described above, a return light does not occur. Accordingly, the amount of the light emission of each channel of the surface-emitting laser array chip can be stabilized. When it is not necessary to consider the effect of a return light (i.e., when a higher resolution is not required for the NIRS), it is satisfactory even if f=L.

Figure 19:
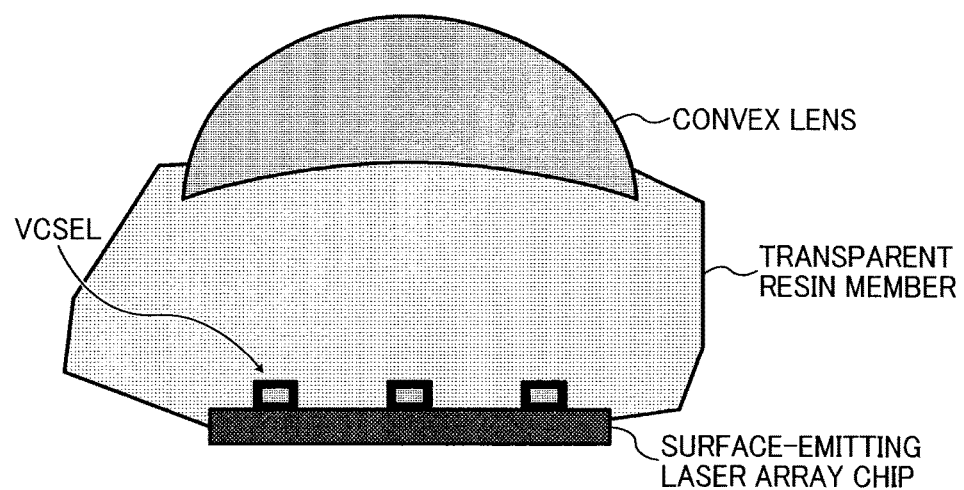
FIG. 19 illustrates a second additional configuration of the light source module according to the first and second examples of the first embodiment of the present invention.

As illustrated in FIG. 19, the space between the convex lens and the surface-emitting laser array chip is filled with a transparent resin so as not to include any airspace. In the present embodiment, the transparent resin is a resin having the refractive index equivalent to that of the convex lens (for example, a thermosetting epoxy resin). Accordingly, the refractive index does not change at the boundary of the interface between the convex lens and the surface-emitting laser array chip. The transparent resin may be formed by a metal mold before the convex lens is attached, or may be implanted after the convex lens is attached.

As the space between the convex lens and the surface-emitting laser array chip is filled with the transparent resin as described above, the reflection of the light emitted from the surface-emitting laser array chip on the surface of convex lens on the surface-emitting laser array chip side, i.e., the occurrence of the return light, can be prevented. As the occurrence of the return light is prevented, the amount of the light emission of the channels can be stabilized. As the amount of the light of the channels is stabilized, the signal-to-noise ratio (S/N) of the measurement system improves, and the high-precision NIRS measurement and high resolution can be achieved.

Figure 20:
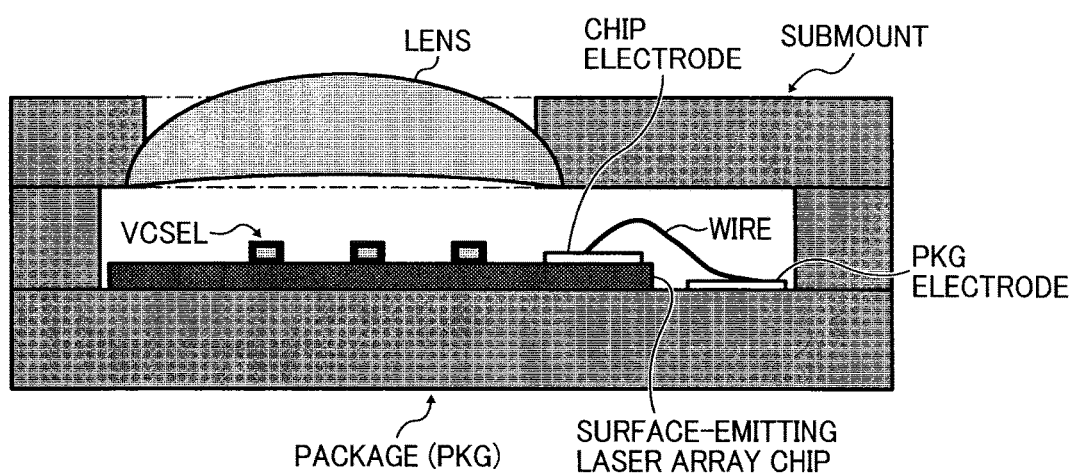
FIG. 20 illustrates a third additional configuration of the light source module according to the first and second examples of the first embodiment of the present invention.

As illustrated in FIG. 20, the surface-emitting laser array chip is mounted on the package, and the convex lens is attached to the package via the submount. In the surface-emitting laser array chip, the electrodes (chip electrodes) on the chip are electrically connected to the package (PKG) electrode on the package through a wire. The wire has the height of about tens of micrometers, and is designed so as not to interfere with the submount. The attached position L of the convex lens (i.e., the distance between the light-emitting surface of the surface-emitting laser array chip and the principal point of the convex lens) is subject to constraints of the height of the wire. More specifically, when a wire is used in the above configuration, the wire may need to avoid the submount in the structure, or the height of the wire may need to be equal to or less than 100 μm. In other words, it is desired that −100 μm<f−L<0. Note that the illustration of the transparent resin illustrated in FIG. 19 is omitted in FIG. 20.

The light emitted from the exit plane of the surface emitting laser is approximately circular, and the divergence angle is about 5 degrees in half value width. As the laser beams of the LD known in the art is elliptic, the installation error in the rotation direction needs to be taken into consideration. However, in the surface emitting laser, such an installation error does not need to be taken into consideration. Moreover, as the light emitted from the exit plane of the surface emitting laser is approximately circular, it is easier to perform approximation or the like utilizing the symmetry of the circular shape when an optical simulation is performed to solve a reverse problem.

The laser beam emitted from the surface emitting laser is refracted by the convex lens disposed nearby. The refraction angle is determined by the relative positions of the surface emitting laser and the center of the lens (i.e., the optical axis of the lens). Accordingly, a desired refraction angle can be obtained by appropriately arranging the position of the lens and the position of the surface-emitting laser array chip of each group.

In the second example, the relative positions of the channel and the optical axis of the convex lens are determined such that the refraction angle becomes about 20 degrees. In the surface-emitting laser array chip, the light emission of the channels can be controlled in an in an independent manner. Accordingly, the direction of the light that is emitted from the light source modules LM can be changed by selecting the channel that is to emit the light.

Figure 21:
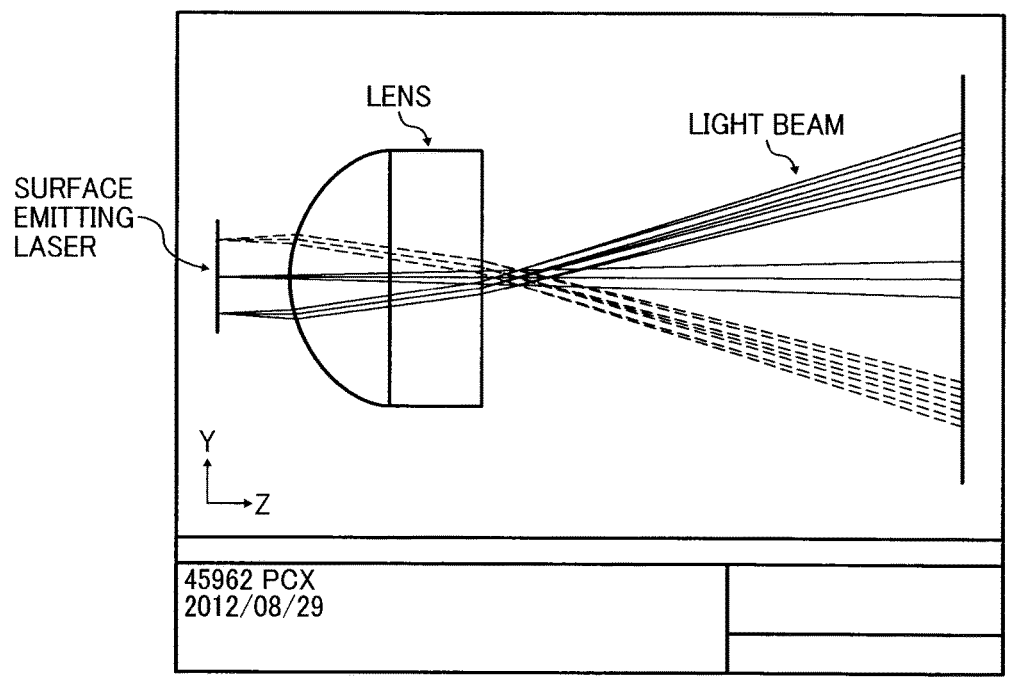
FIG. 21 illustrates an example of the light beams that are optically designed by an optical simulator, according to the first embodiment of the present invention.

FIG. 21 illustrates an example of the light beams that are optically designed by an optical simulator, according to the present embodiment. In FIG. 21, three channels (light sources) that simulate a surface-emitting laser array chip are provided, and a 1 mm lens in diameter with f=600 micrometer (μm) is disposed in the proximity of these three channels. One of the three channels is disposed on the optical axis of the lens, and the other two channels are separately disposed on two sides of the optical axis of the lens. The rays of light emitted from the other two channels that are not on the optical axis are refracted by the lens, and the propagation direction (path) is bent. More specifically, the rays of light emitted from the other two channels that are not on the optical axis are exited with the angle of about degrees with reference to the optical axis of the lens, and the these two rays of light are exited in opposite directions with reference to the optical axis.

In the present embodiment, the light source module LM is designed such that the incident angle at which the light enters the test object becomes about 55 degrees. More specifically, as illustrated in FIG. 16, the light source module LM is designed such that the multiple rays of light exiting from the convex lens in the direction with the oblique angle of about 20 degrees with reference to the optical axis are separately deflected by multiple prisms. Accordingly, the angles of the multiple rays of light with reference to the optical axes of the corresponding lenses are changed from about 20 degrees to about 55 degrees, and the incident angle at which the rays of light enter the surface of the test object becomes about 55 degrees.

Figure 22:
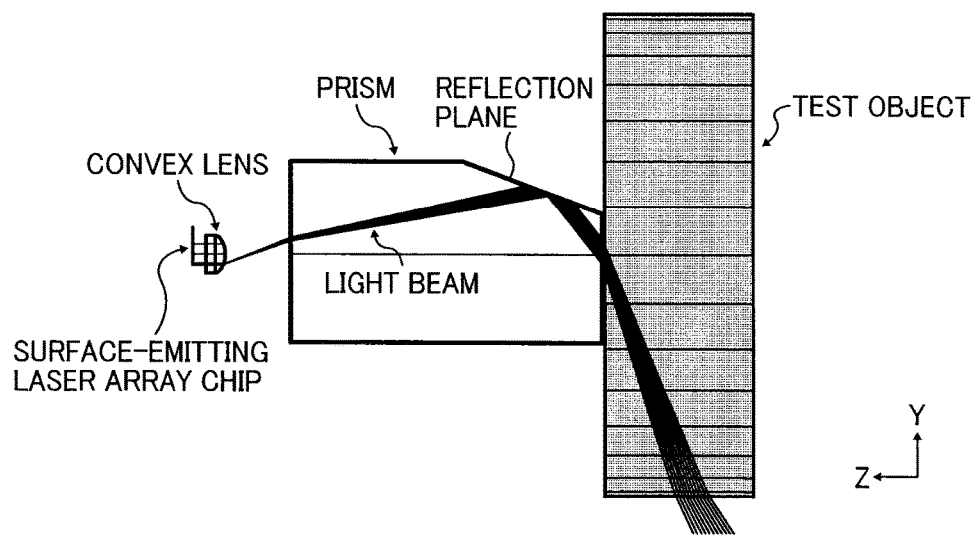
FIG. 22 illustrates an example of the result of the optical simulation according to the first embodiment of the present invention.

Note that the prism may be made of any material as long as it can reflect light. For example, the prism may be made of a glass substrate on which a metal film is formed. Alternatively, for example, a prism in which total internal reflection caused by a difference in refractive index is utilized may be adopted. FIG. 22 illustrates an example of the result of the optical simulation according to the first embodiment. The light beam emitted from the VCSEL is refracted by the convex lens, and then enters the prism.

In the present embodiment, the material of the prism is BK7. However, the prism may be made of any known optical material. The light that has entered the prism is reflected by the side (reflection plane) of the prism by total internal reflection, and enters the test object with the incident angle of about 55 degrees. In other words, the light that has passed through the convex lens is deflected by the prism in such a manner that the incident angle at which the light enters the test object becomes about 55 degrees. In this configuration, a transparent gel intervenes between the prism and the test object so as to prevent the dispersion of the light on the interface between the prism and the test object. The rays of light emitted from the surface-emitting laser array chips becomes a plurality of rays of light that are not parallel to each other after passing through the convex lens, and these rays of light are reflected by the prisms and enter the test object. As a result, a plurality of approximately collimating rays of light that are not parallel to each other enters the same point of the test object (see FIG. 22).

By the Snell laws of reflection, the propagation angle of the light beam in the test object changes from about 55 degrees to about 60 degrees due to the difference in refractive index between the prism and the test object.

In the optical system for which the convex lens and the prism are provided, the positions of the channels of the surface-emitting laser array chip are different from each other. Accordingly, the propagation angles of the rays of light in the test object are adjustable. In the present embodiment, the centers of the channels (VCSEL) are displaced from the optical axis of the convex lens by about 200 μm. Accordingly, the propagation angles of the rays of light emitted from the channels in the test object can be adjusted to about 60 degrees. As a result, the multiple rays of light emitted from the multiple channels exit from a plurality of different positions on the exit plane of the convex lens as a plurality of approximately collimating rays of light that are not parallel to each other.

Figure 23:
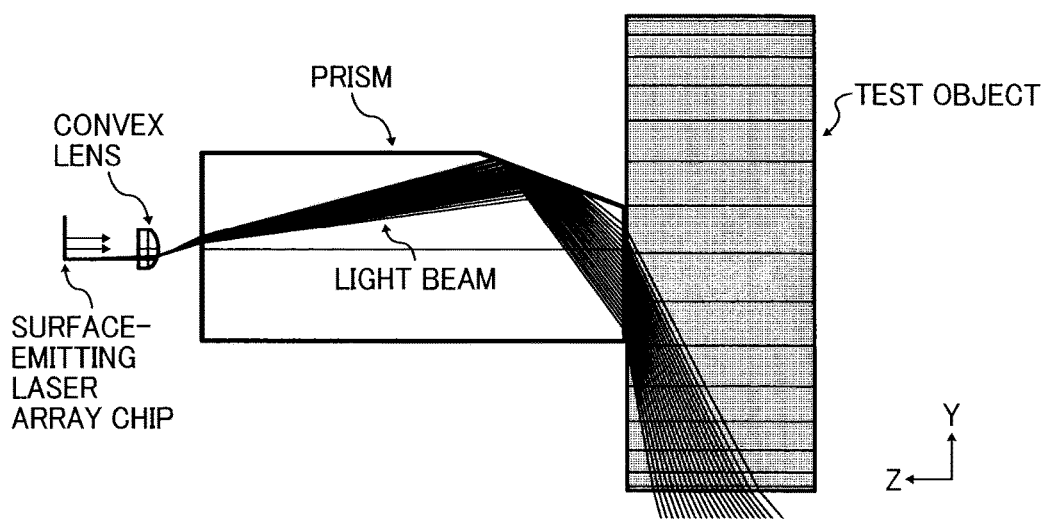
FIG. 23 illustrates an example of the result of the optical simulation according to a control sample.

FIG. 23 illustrates, as a control sample, an example of the result of the optical simulation where the lens is configured such that the focal length f=600 μm and the attached position L=1.6 mm. When the difference between L and f becomes equal to or greater than 1 mm, as illustrated in FIG. 23, the laser beam diverges too widely. In such cases where the laser beam diverges in an excessive manner as described above, the incident plane of the test object needs to be broadened. However, the practical size of the incident plane of the test object in the NIRS is actually about φ2 mm at the maximum. This restriction is present because the space among the roots of the hairs of a human is about 2 mm and the hairs optically disturb the NIRS when the dimension is wider than the above. With such disturbance, the NIRS with high resolution cannot be achieved. In short, it is desired that the difference between L and f be shorter than 1 mm.

The first and second lenses illustrated in FIG. 16 are directly attached to a ceramic package on which the surface-emitting laser array chip is mounted, such that these lenses are disposed at designed positions in a precise and stable manner.

In FIG. 21, the convex surface of the lens is directed to the surface emitting laser side. However, the direction of the convex lens may be the other way around. When the lens is arranged such that the convex surface of the lens is directed to the surface emitting laser side and the planar portion of the lens is directed to the test object as illustrated in FIG. 21, the distance between the surface emitting laser chip and the lens can be made longer. In the chip implementation processes, it is desired that the allowed distance be long to a certain extent. When the allowed distance is sufficiently long, the interference of parts or an arm that picks up the parts in the implementation processes can be prevented.

The lens may be any optics as long as it can refract the light. For example, a gradient index (GRIN) lens that utilizes the refractive distribution of an optical fiber may be used for the lens. When such a GRIN lens is adopted, a low-cost lens with a small spherical aberration and a small f number can be selected compared with when a spherical lens is adopted.

In the second example, the light enters the edge of the lens rather than the center of the lens. For this reason, it is desired that the spherical aberration be smaller.

As described above, the light source module LM emits a plurality of rays of light that are not parallel to each other (see FIG. 16 and FIG. 22).

Then, these rays of light that are not parallel to each other emitted from the light source module LM enters the same point of the test object (see FIG. 16 and FIG. 22).

For example, when the light source modules LM are disposed at about 60 mm intervals, the term "same point" indicates a same point with reference to such 60 mm. More specifically, a plurality of positions that are away from each other by about several millimeters are considered to be the same points. In other words, the term "same" in "same point" does not strictly indicate the same, but should include "almost the same" or "approximately the same".

In an algorithm for solving a reverse problem, an optical simulation where the position of the light source module LM is set is performed. In such an optical simulation, if the displacement of the position at which the light enters the test object is precisely set, no error occurs in the estimation of the reverse problem. The same can be said of a surface-emitting laser array chip provided with a plurality of channels with varying oscillation wavelengths. Even when the positions at which multiple rays of light from a plurality of channels with varying oscillation wavelengths enter the test object are displaced from each other by several millimeters, these position are considered to be the same points.

Alternatively, when the distance among the probes is reduced to dispose the probes with high density, the areas on the test object irradiated with light by a plurality of light source modules LM (probes for light irradiation) are close to each other. Accordingly, it is desired that the displacement of the positions at which the multiple rays of light enter the test object be smaller. In other words, it is desired that the sameness of the "same point" as described above be higher.

In view of the above circumstances, the inventors found that the displacement of the positions at which the multiple rays of light from the light source module LM enter the test object can be reduced by making the light exit directions of a plurality of light-emitting units of a surface-emitting laser array chip not parallel to each other. In the following description, such a method is described in detail.

Figure 24:
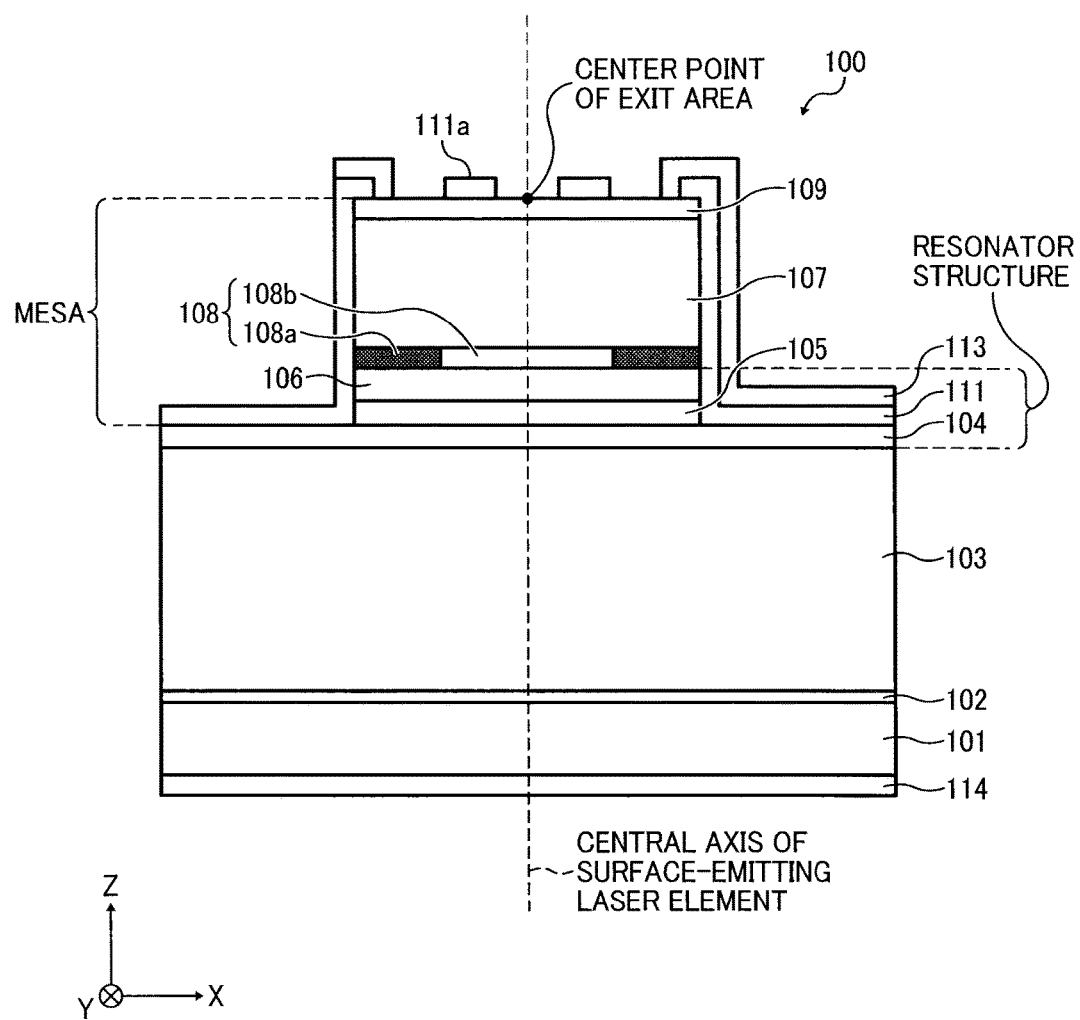
FIG. 24 is a diagram illustrating the configuration of a surface-emitting laser element in the surface-emitting laser array chip according to a first modification of the second example.

FIG. 24 is an XZ-sectional view of a surface-emitting laser element that makes up each of the light-emitting units of a surface-emitting laser array chip of the light source module LM according to a first modification of the second example of the first embodiment. In the following description, it is assumed that the direction of the laser oscillation is the Z-axis direction, and that the two directions orthogonal to each other on a plane perpendicular to the Z-axis direction are the X-axis direction and the Y-axis direction.

The surface-emitting laser element 100 is, for example, a surface-emitting laser element with the oscillation wavelength of 780 nm band, and includes, for example, a substrate 101, a buffer layer 102, a lower substrate DBR 103, a lower spacer layer 104, an active layer 105, an upper spacer layer 106, an upper semiconductor DBR 107, and a contact layer 109.

Figure 25A:
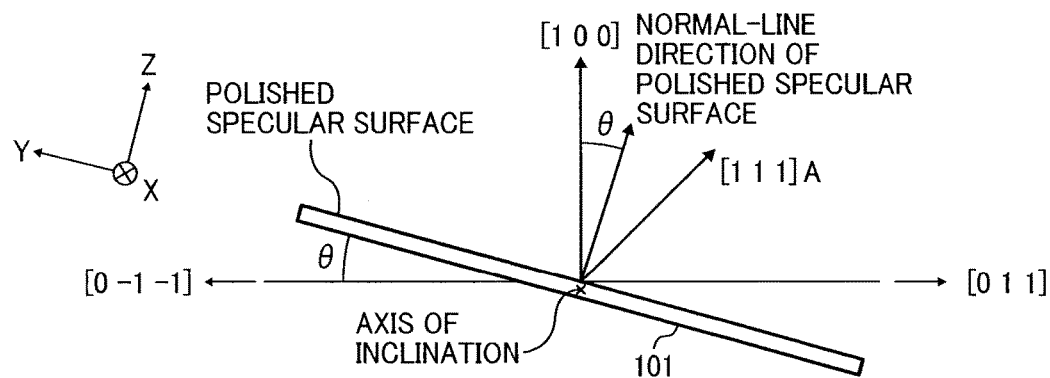
FIG. 25A and FIG. 25B are first and second diagrams illustrating an inclined substrate according to the first embodiment.
Figure 25B:
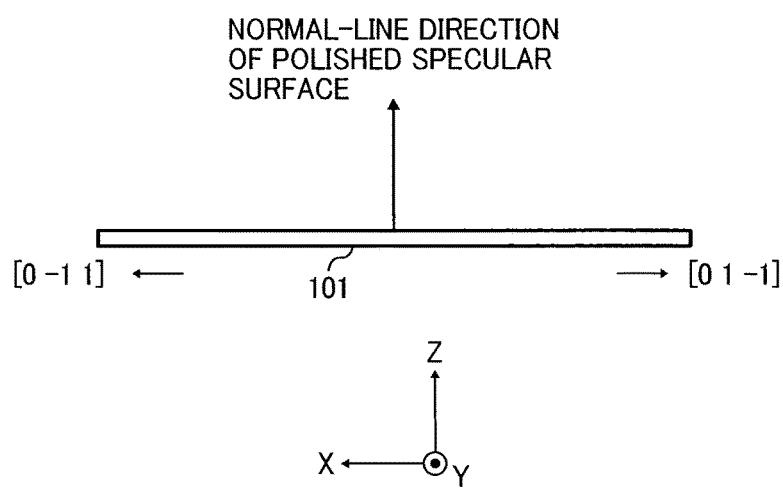

FIG. 25A and FIG. 25B are first and second diagrams illustrating an inclined substrate according to the first embodiment. The substrate 101 has a polished specular surface, and as illustrated in FIG. 25A, is an n-GaAs single-crystal substrate where the normal-line direction of the polished specular surface (principal plane) is inclined towards a crystal orientation [111] A by 15 degrees ($\theta$=15 degrees) with reference to a crystal orientation [100]. In other words, the substrate 101 is so-called inclined substrate. In this first modification, as illustrated in FIG. 25B, the substrate 101 is disposed such that the crystal orientations [0 −1 1] and [0 1 −1] are the +X direction and the −X direction, respectively. In this first modification, due to the use of the inclined substrate for the substrate 101, the polarization is controlled such that the polarization direction is stabilized to the X-axis direction.

The buffer layer 102 is composed of n-GaAs, and is stacked on the surface of the substrate 101 on the +Z side.

The lower substrate DBR 103 includes 42.5 pairs of a low refractive index layer that is composed of n-$Al_{0.93}Ga_{0.07}As$ and is stacked on the surface of the buffer layer 102 on the +Z side and a high refractive index layer composed of n-$Al_{0.3}Ga_{0.7}As$. Between two layers of varying refractive indexes, a gradient-composition layer with the thickness of 20 nm where the composition gradually changes from a side of the composition to the other side of the composition is provided in order to reduce the electrical resistance. Each of the layers of varying refractive indexes is designed to include one-half of the adjacent gradient-composition layer and have the optical thickness of $\lambda/4$ when it is assumed that the oscillation wavelength is $\lambda$. Note that when the optical thickness is $\lambda/4$, the actual thickness of the layer is D=$\lambda/4n$ (where n denotes the refractive index of the medium of that layer).

The lower spacer layer 104 is stacked on the lower substrate DBR 103 on the +Z side, and is composed of non-doped $Al_{0.33}Ga_{0.67}As$.

The active layer 105 is stacked on the lower spacer layer 104 on the +Z side, and has a triple-bond quantum well structure composed of GaInAsP/$Al_{0.33}Ga_{0.67}As$.

The upper spacer layer 106 is stacked on the active layer 105 on the +Z side, and is composed of non-doped $Al_{0.33}Ga_{0.67}As$.

The portion consisting of the lower spacer layer 104, the active layer 105, and the upper spacer layer 106 is referred to as a resonator structure, and is designed to include one-half of the adjacent gradient-composition layer and have the optical thickness of one wavelength. The active layer 105 is disposed in the center of the resonator structure so as to achieve a high stimulated-emission rate. Note that the center of the resonator structure corresponds to a belly of the standing-wave distribution of the electric field.

The upper semiconductor DBR 107 is stacked on the upper spacer layer 106 on the +Z side, and includes 32 pairs of a low refractive index layer that is composed of p-$Al_{0.93}Ga_{0.07}As$ and a high refractive index layer composed of p-$Al_{0.33}Ga_{0.67}As$. Between two layers of varying refractive indexes, a gradient-composition layer is provided. Each of the layers of varying refractive indexes is designed to include one-half of the adjacent gradient-composition layer and have the optical thickness of $\lambda/4$.

One of the low refractive index layers upper semiconductor DBR 107 includes an inserted to-be-selected oxidized layer composed of p-$Al_{0.99}Ga_{0.11}As$ with the thickness of 30 nm. The to-be-selected oxidized layer is inserted into the low refractive index layer in the second pair from the upper spacer layer 106.

The contact layer 109 is stacked on the upper semiconductor DBR 107 on the +Z side, and is composed of p-GaAs.

Note that in the following description, the product of a plurality of semi-conducting layers stacked on the substrate 101 as described above is referred to simply as a layered product.

Next, a method of manufacturing the surface-emitting laser element 100 is described.

(1) The layered product as described above is formed by crystal growth using the metal-organic chemical vapor deposition (MOCVD) or the molecular beam epitaxy (MBE). In the present embodiment, trimethylaluminum (TMA), trimethylgallium (TMG), and trimethylindium (TMI) are used as a group III material, and Phosphine ($PH_3$) and arsine ($AsH_3$) are used as a group V material. Moreover, carbon tetrabromide ($CBr_4$) and dimethyl zinc (DMZn) are used as a p-type dopant material, and hydrogen selenide ($H_2Se$) is used as a n-type dopant material (2) On the surface of the layered product, a square-shaped resist pattern in a desired mesa shape with the sides of 25 µm is formed.

(3) The inductively coupled plasma (ICP) dry etching is adopted, and a quadrangular-prism mesa is formed using the resist pattern as a photomask. In the present modification, the bottom of the etching is placed inside the lower spacer layer 104.

(4) The photomask is removed.

(5) The layered product is heated up in the vapor. In the present modification, aluminum (Al) in a to-be-selected oxidized layer 108 is selectively oxidized from the periphery of the mesa. In this configuration, a non-oxidized area 108b that is surrounded by an oxidized layer 108a of Al is left non-oxidized in the center of the mesa. As a result, an oxidation constriction structure is formed that limits the path of the driving current of the light-emitting units to the center of the mesa. The non-oxidized area 108B is a current-carrying area (current injection area). In the present modification, in view of the results of various types of preliminary experiments, the conditions for heating (such as the holding temperature and holding duration in time) are appropriately selected such that the current-carrying area 108b has a desired size.

(6) On the surface of the layered product, a resist mask for forming a trench for separation (chip cutting) is disposed.

(7) The resist mask is used as an etching mask, and a trench for separation (chip cutting) is formed using the dry etching.

(8) The plasma-enhanced chemical vapor deposition (plasma CVD) is used to form a protective layer 111 made of silicon mononitride (SiN). In the present modification, the optical thickness of the protective layer 111 is $\lambda/4$. More specifically, the refractive index of SiN and the oscillation wavelength are 1.86 and 780 nm, respectively, and thus the actual film thickness (=λ/4n) is designed to be about 105 nm.

(9) At the upper part of the mesa that serves as an exit plane of the laser beam, an etching mask for opening the window of a p-side electrode contact is formed. Note that such an etching mask will be referred to as a mask M in the following description. In the present modification, the mask M is formed around the mesa. More specifically, the mask M is formed such that an area from the protective layer 111 on the top surface of the mesa and at the periphery of the top surface of the mesa to a ring-shaped area 111a on the top surface of the mesa is not etched. In the present modification, the distance between the center of the internal diameter of the ring-shaped area 111a and the center point of the light exit area, with reference to a direction perpendicular to the Z-axis direction when viewed from the Z-axis direction, varies according to an area where the light-emitting unit (ch) as illustrated in FIG. 17 is disposed.

(10) The protective layer 111 is etched with buffered hydrogen fluoride (BHF), and the window of the p-side electrode contact is opened.

(11) The mask M is removed.

(12) At an area on the upper part of the mesa that servers as a light-exiting portion (opening on a metal layer), a square-shaped resist pattern with the sizes of 10 μm is formed, and the vapor deposition of a p-side electrode material is performed. The p-side electrode material may be a multilayer film composed of Cr/AuZn/Au or a multilayer film composed of Ti/Pt/Au.

(13) The electrode material that is evaporated onto the area that serves as a light-exiting portion (light exit area) is lifted off, and a p-side electrode 113 is formed. This area that is surrounded by the p-side electrode 113 is a light exit area. At the light exit area, the ring-shaped dielectric 111a of the protective layer 111 is left (see FIG. 24). Note that the ring-shaped dielectric 111a is referred to as a ring-shaped dielectric in the following description. In the present modification, the material of the ring-shaped dielectric (the material of the protective layer 111) is SiN. However, the material of the ring-shaped dielectric may be a different dielectric such as SiO and $SiO_2$.

The ring-shaped dielectric serves to control the reflectance inside the light exit area. In other words, in the light exit area, the ring-shaped portion having a dielectric serves as a low-reflection area, and the portion having no dielectric serves as a high-reflection area. Due to this configuration, transverse mode, the high-order lateral mode optical output can effectively reduced without degrading the basic lateral mode optical output. Further, the beam quality of the exit light improves.

(14) The rear side of the substrate 101 is polished to a prescribed thickness (for example, about 100 μm), and then n-side electrode 114 is formed. In the present modification, the n-side electrode 114 is a multilayer film composed of AuGe/Ni/Au.

(15) Annealing is conducted to achieve the ohmic conduction between the p-side electrode 113 and the n-side electrode 114. Accordingly, the mesa can serve as a light-emitting unit.

(16) Cutting is performed for each chip, and each of the obtained product is mounted on a ceramic package.

In the present modification, when the center point of the ring-shaped dielectric (the center of the internal diameter of the ring-shaped dielectric) formed at the light exit area matches the center point of the light exit area when viewed from the Z-axis direction, the light exit direction of the light-emitting units of the surface-emitting laser array chip becomes the +Z direction (the direction orthogonal to the substrate 101). On the other hand, when the center point of the ring-shaped dielectric is displaced (offset) from the center point of the light exit area when viewed from the Z-axis direction, the light exit direction of the light-emitting units becomes inclined with reference to the +Z direction (the direction orthogonal to the substrate 101). In the present modification, for the purpose of simplification, the inclination in the light exit direction due to the use of an inclined substrate is not taken into consideration. Note that the term "center point of the light exit area" indicates the point of intersection of the axis orthogonal to the substrate 101 and passing through center point of the current-carrying area (the central axis of the surface-emitting laser element 100) and the exit plane (the top surface of the contact layer 109). Accordingly, the term "center point of the light exit area" in equivalent to the "center point of the exit plane".

In view of the principles as described above, the surface-emitting laser array chip according to the first modification of the second example where the exit directions of the multiple light-emitting units are different from each other is developed.

Figure 26A:
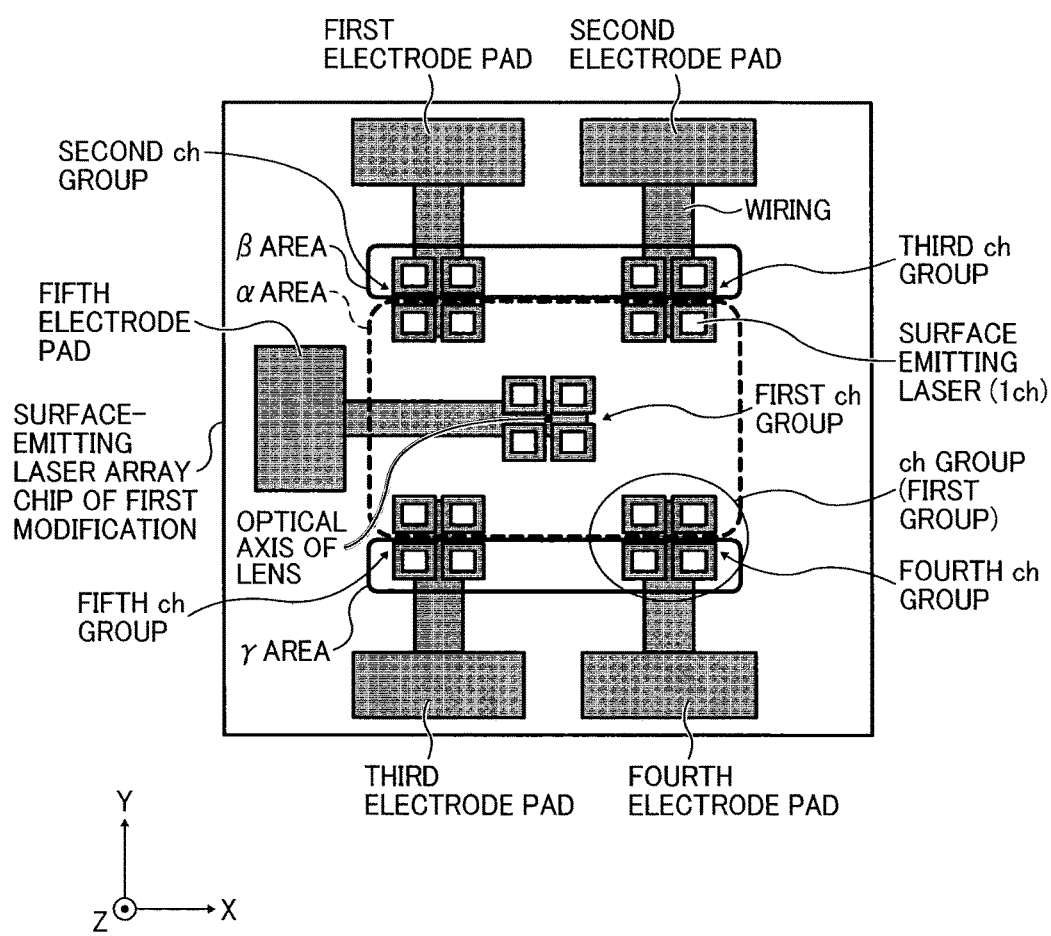
FIG. 26A to FIG. 26D are first to fourth diagrams illustrating a first offset distribution model in the surface-emitting laser array chip according to the first modification of the second example.
Figure 26B:
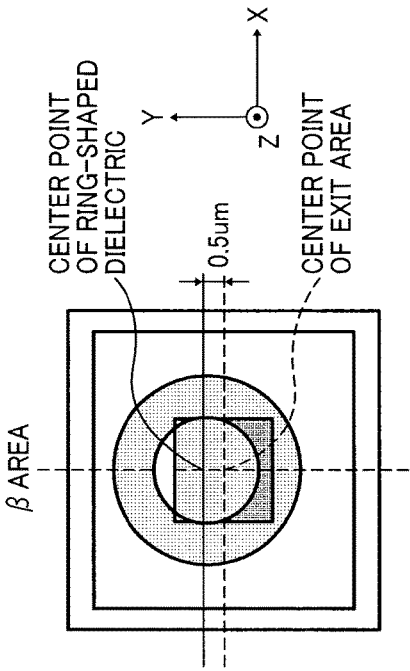
Figure 26C:
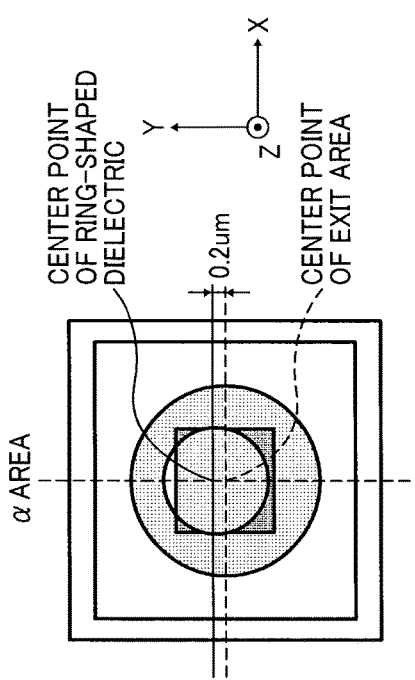
Figure 26D:
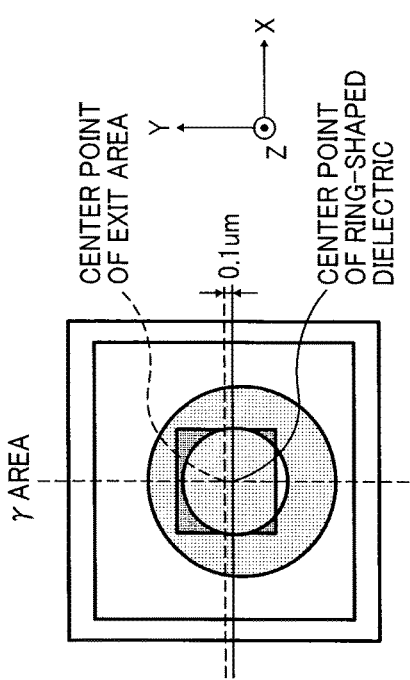
Figure 27:
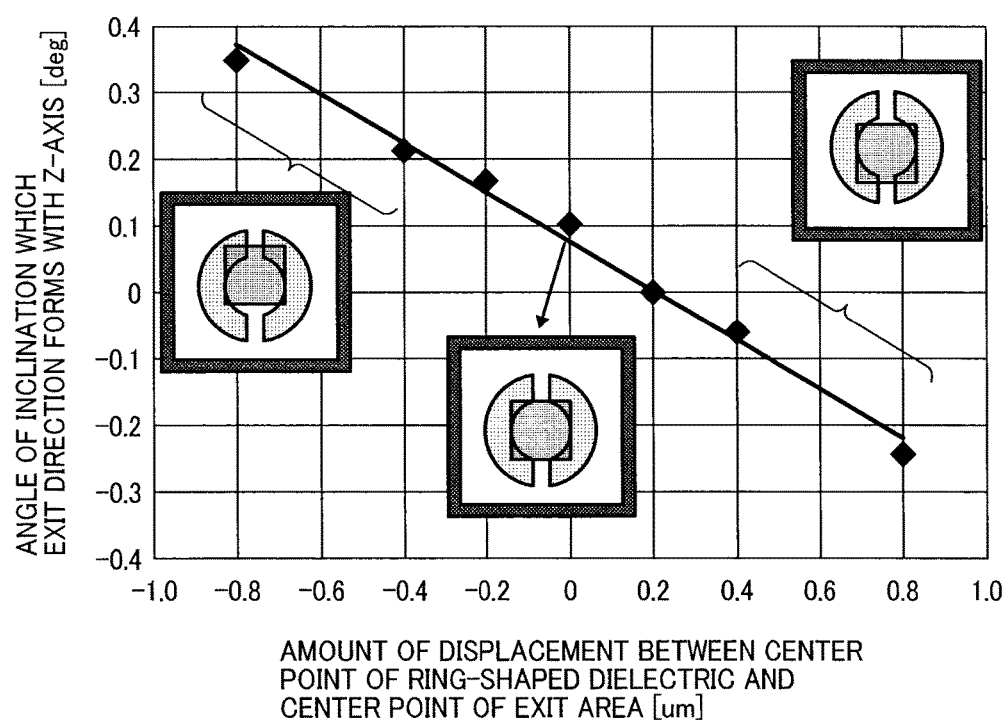
FIG. 27 is a diagram illustrating relation between the amount of the displacement between the center point of the ring-shaped dielectric and the center point of the light exit area and the angle of inclination which the light exit direction forms with the Z-axis in a first modification of the second example.

With reference to FIG. 26A to FIG. 27, a first offset distribution model in the surface-emitting laser array chip according to the first modification is described where relative positions (offset) of the center point of the ring-shaped dielectric and the center point of the light exit area when viewed from the Z-axis direction are varied according to the area in which the light-emitting unit is disposed. The first offset distribution model may be implemented by the design of a mask that is used for etching the protective layer 111.

As illustrated in FIG. 26A, the surface-emitting laser array chip according to the first modification includes a first channel group, and second to fifth groups that are disposed around the first channel group.

More specifically, each of the channel groups includes four channels (light-emitting units) disposed in a tetragonal lattice in the X-axis direction and the Y-axis direction. Further, the first channel group is disposed at the point of intersection of the diagonal lines of the square, and the second to fifth groups of light-emitting units are separately disposed at the four vertices of the square. In the present modification, the surface-emitting laser array chip and the lens are aligned such that the center of the first channel group is on the optical axes of the lens.

In the first offset distribution model, an α area denotes an area including four channels of the first channel group, two channels of each of the second and fifth third groups on the −Y side, and two channels of each of the fourth and fifth channel groups on the +Y side (i.e., an area including eight channels in total), and a β area denotes an area including two channels of each of the second and third channel groups on the +Y side (i.e., an area including four channels in total). Moreover, a γ area denotes an area including two channels of each of the fourth and fifth channel groups on the −Y side (i.e., an area including four channels in total).

In the first offset distribution model, the offsets of the channels in the Y-axis direction are made different from each other among the areas. Here, the offset indicates at least one of the offset amount or offset direction of the center point of the ring-shaped dielectric in the Y-axis direction with reference to the center point of the light exit area when viewed from the Z-axis direction.

FIG. 27 is a diagram illustrating relation between the amount of the displacement between the center point of the ring-shaped dielectric and the center point of the light exit area and the angle of inclination which the light exit direction forms with the Z-axis in the first modification of the second example. The graph in FIG. 27 indicates the relation between the offset of the channels in the Y-axis direction and the angle of inclination which the light exit direction forms with the Z-axis.

FIG. 27 indicates that the light exit direction at each of the channels changes according to the offset in the Y-axis direction. More specifically, the light exit direction at each of the channels is inclined in the direction (−Y direction or +Y direction) opposite the direction of the offset in the Y-axis direction with reference to the Z-axis (+Y direction or −Y direction), and the angle of inclination is almost proportional to the offset amount.

In the first modification, the substrate (inclined substrate) 101 that is inclined around the X-axis is used. For this reason, when the center point of the ring-shaped dielectric matches the center point of the light exit area when viewed from the Z-axis direction, the light exit direction is shifted towards the +Y direction by about 0.1 percent (see FIG. 27).

In order to deal with such situation, in the first modification, as illustrated in FIG. 26B, the center point of the ring-shaped dielectric is offset towards the +Y direction with reference to the center point of the light exit area by 0.2 μm, such that the angle of inclination of the light exit direction at each of the channels becomes 0.0 degree at the α area with reference to the Z-axis.

Moreover, as illustrated in FIG. 26C, the center point of the ring-shaped dielectric is offset towards the +Y direction with reference to the center point of the light exit area by 0.5 μm, such that the light exit direction at each of the channels is inclined towards the −Y direction by a desired angle δ (about 0.15 degree) at the β area with reference to the Z-axis.

Moreover, as illustrated in FIG. 26D, the center point of the ring-shaped dielectric is offset towards the −Y direction with reference to the center point of the light exit area by 0.1 μm, such that the light exit direction at each of the channels is inclined towards the +Y direction by a desired angle δ (about 0.15 degree) at the γ area with reference to the Z-axis.

Next, a second offset distribution model of the second modification is described with reference to FIG. 28A to FIG. 28D. In contrast to the first modification, no inclined substrate is used in the surface-emitting laser element of the second modification. In other words, in the substrate of the surface-emitting laser element according to the second modification, the normal-line direction of the polished specular surface matches the crystal orientation [100] direction.

In the second offset distribution model, an a' area denotes an area including four channels of the first channel group, two channels of each of the second and fifth channel groups on the +X side, and two channels of each of the third and fourth channel groups on the −X side (i.e., an area including eight channels in total), and a β area denotes an area including two channels of each of the second and fifth channel groups on the −X side (i.e., an area including four channels in total). Moreover, a γ' area denotes an area including two channels of each of the third and fourth channel groups on the +X side (i.e., an area including four channels in total).

In the second offset distribution model, the offsets of the channels in the X-axis direction are made different from each other among the areas. Here, the offset indicates at least one of the offset amount or offset direction of the center point of the ring-shaped dielectric in the X-axis direction with reference to the center point of the light exit area when viewed from the Z-axis direction. In a similar manner to the offset in the Y-axis direction (see FIG. 27), in the offset in the X-axis direction, the offset amount and angle of inclination in the light exit direction has a linear relation.

Figure 28A:
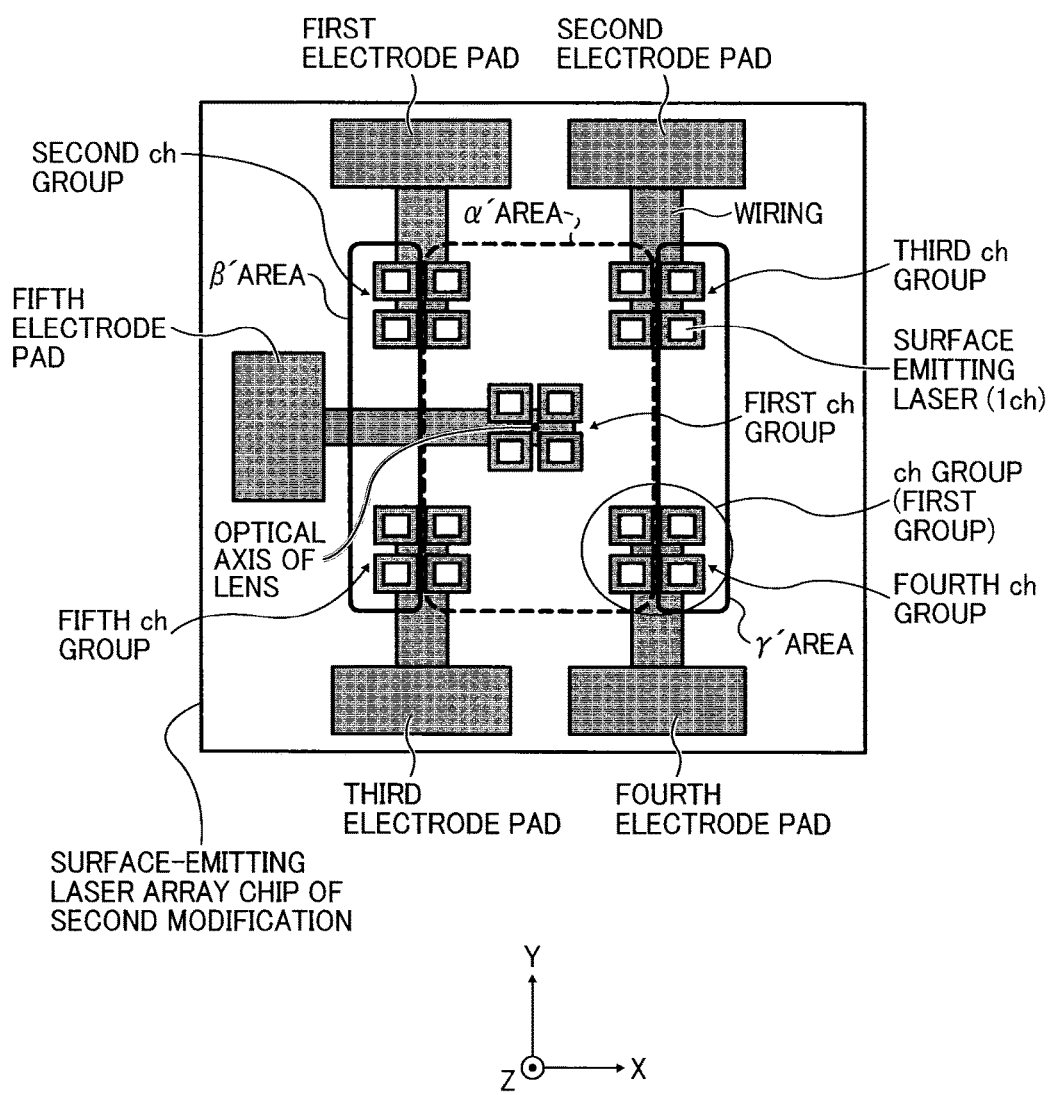
FIG. 28A to FIG. 28D are first to fourth diagrams illustrating a second offset distribution model in the surface-emitting laser array chip according to the second modification of the second example.
Figure 28B:
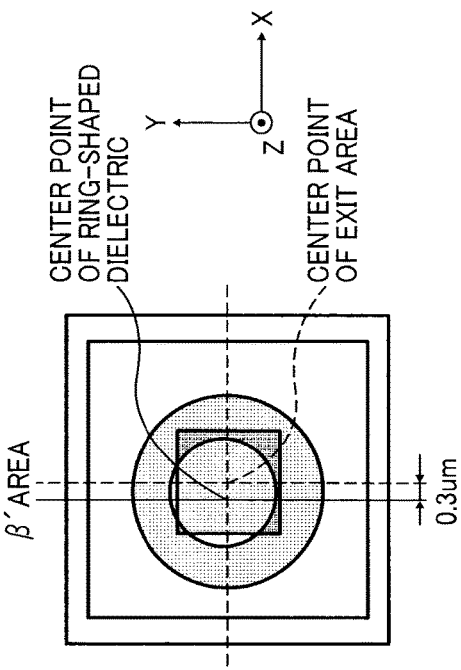
Figure 28C:
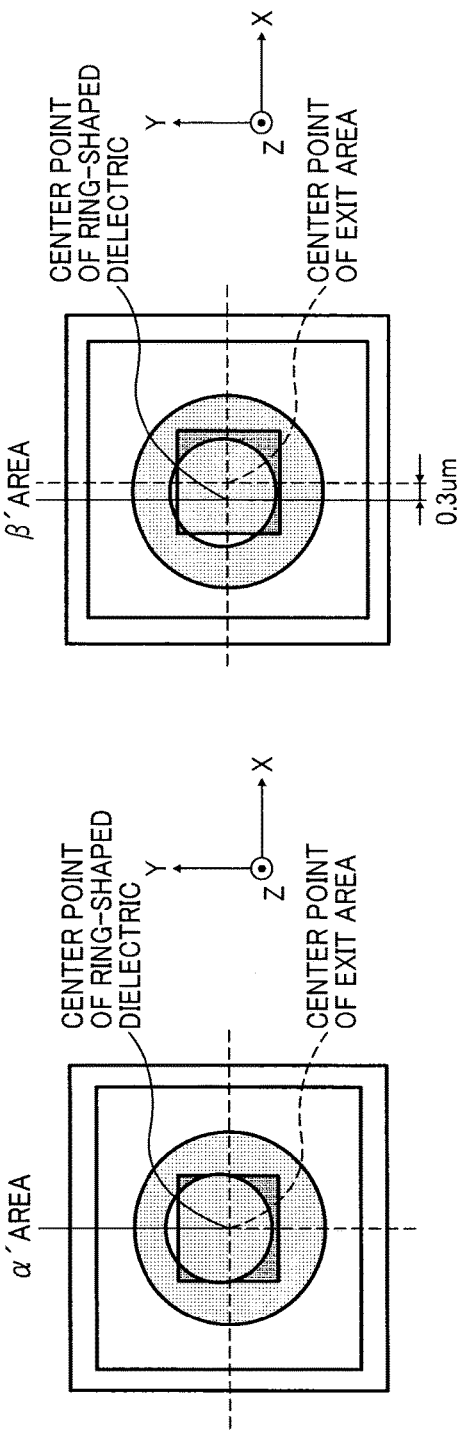

More specifically, in the α' area, the ring-shaped dielectric is not offset with reference to the light exit area (see FIG. 28B). In other words, in the α' area, the center point of the ring-shaped dielectric matches the center point of the light exit area when viewed from the Z-axis direction, and the light exit direction at each of the channels is parallel to the Z-axis. In the β' area, the center point of the ring-shaped dielectric is offset towards the −X direction with reference to the center point of the light exit area by 0.3 μm, such that the light exit direction at each of the channels is inclined towards the +X direction by a desired angle δ (about 0.15 degree) with reference to the Z-axis (see FIG. 28C).

Figure 28D:
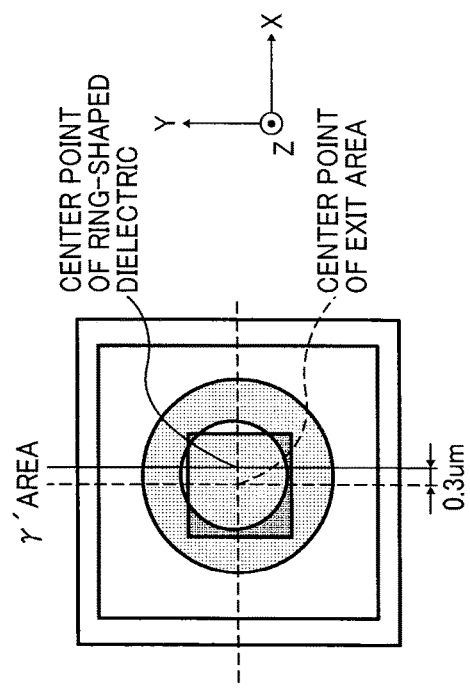

In the γ' area, the center point of the ring-shaped dielectric is offset towards the +X direction with reference to the center point of the light exit area by 0.3 μm, such that the light exit direction at each of the channels is inclined towards the −X direction by a desired angle δ (about 0.15 degree) with reference to the Z-axis (see FIG. 28D).

The first offset distribution model and the second offset distribution model as described above are examples in which the offset is performed in the Y-axis direction and the X-axis direction, respectively. However, the offset may be performed in both the X-axis direction and the Y-axis direction. In such configuration, the light exit direction may be inclined towards the +X direction or −X direction or towards the +Y direction or −Y direction with reference to the Z-axis.

Figure 29:
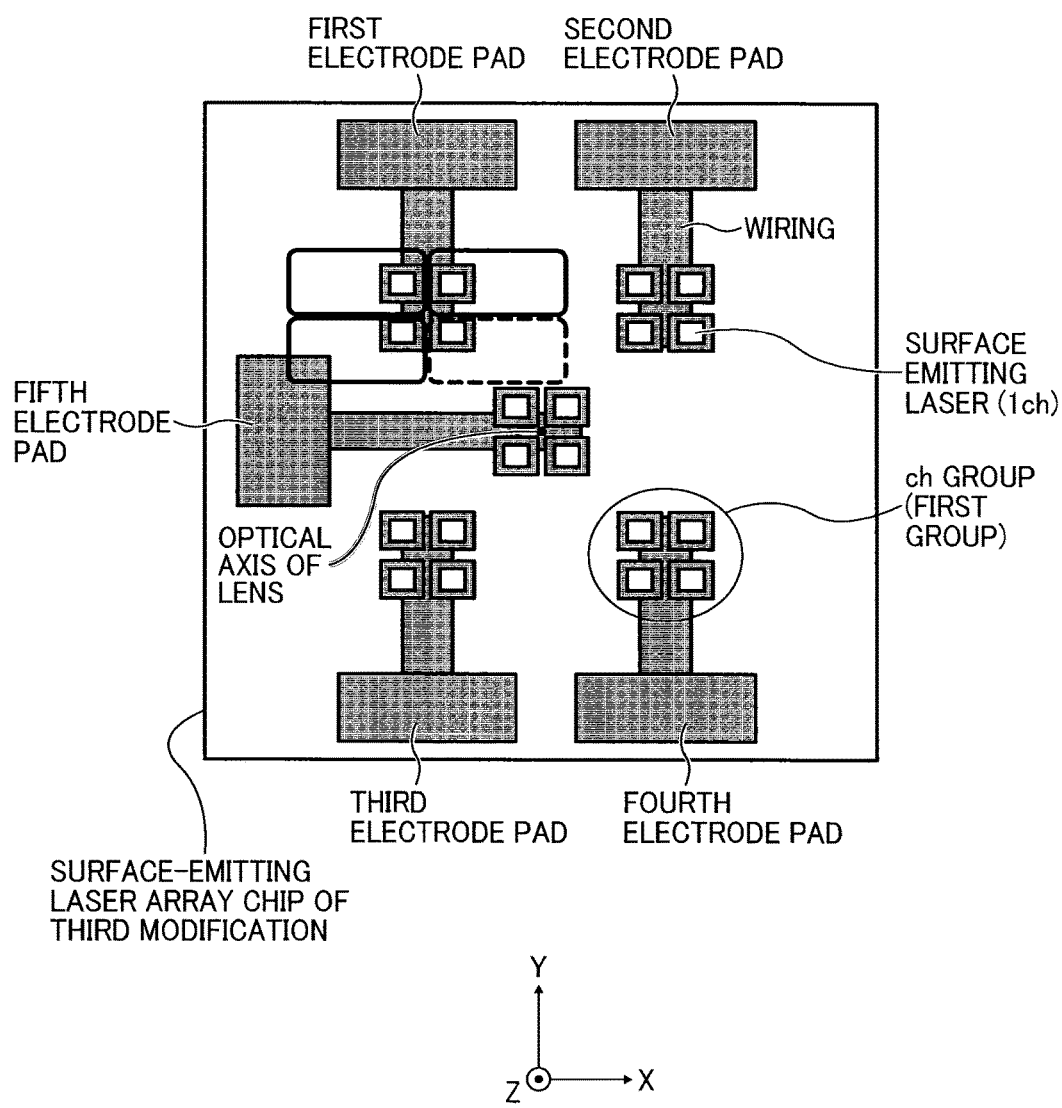
FIG. 29 is a diagram illustrating a third offset distribution model in the surface-emitting laser array chip according to the third modification of the second example.

FIG. 29 is a diagram illustrating a third offset distribution model in the surface-emitting laser array chip according to the third modification of the second example. As illustrated in FIG. 29, the offsets at the four channels of each of the channel groups may be varied from each other.

In other words, the offset distribution model is not limited to the first to third offset distribution models of the first to third modifications as described above, but may be changed as desired.

Figure 30:
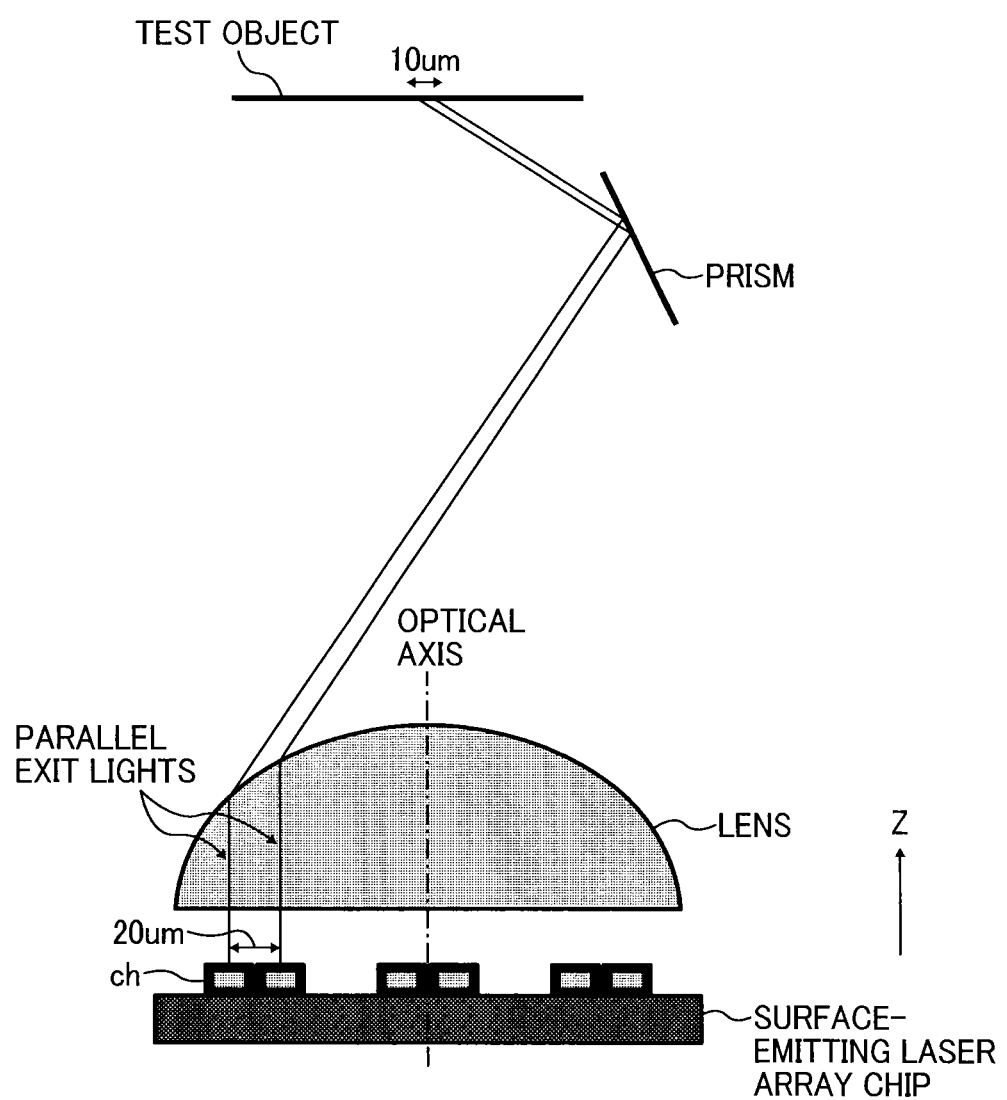
FIG. 30 is a diagram illustrating the operation of a light source module according to a control sample.

FIG. 30 is a diagram illustrating the operation of a light source module according to a control sample. As illustrated in FIG. 30 for example, when the light exit directions of a plurality of channels adjacent to each other in a surface-emitting laser array chip are parallel to each other, the positions at which the multiple rays of light emitted from the multiple channels enter the test object via the lens and prism is displaced, for example, by about 10 μm.

Figure 31:
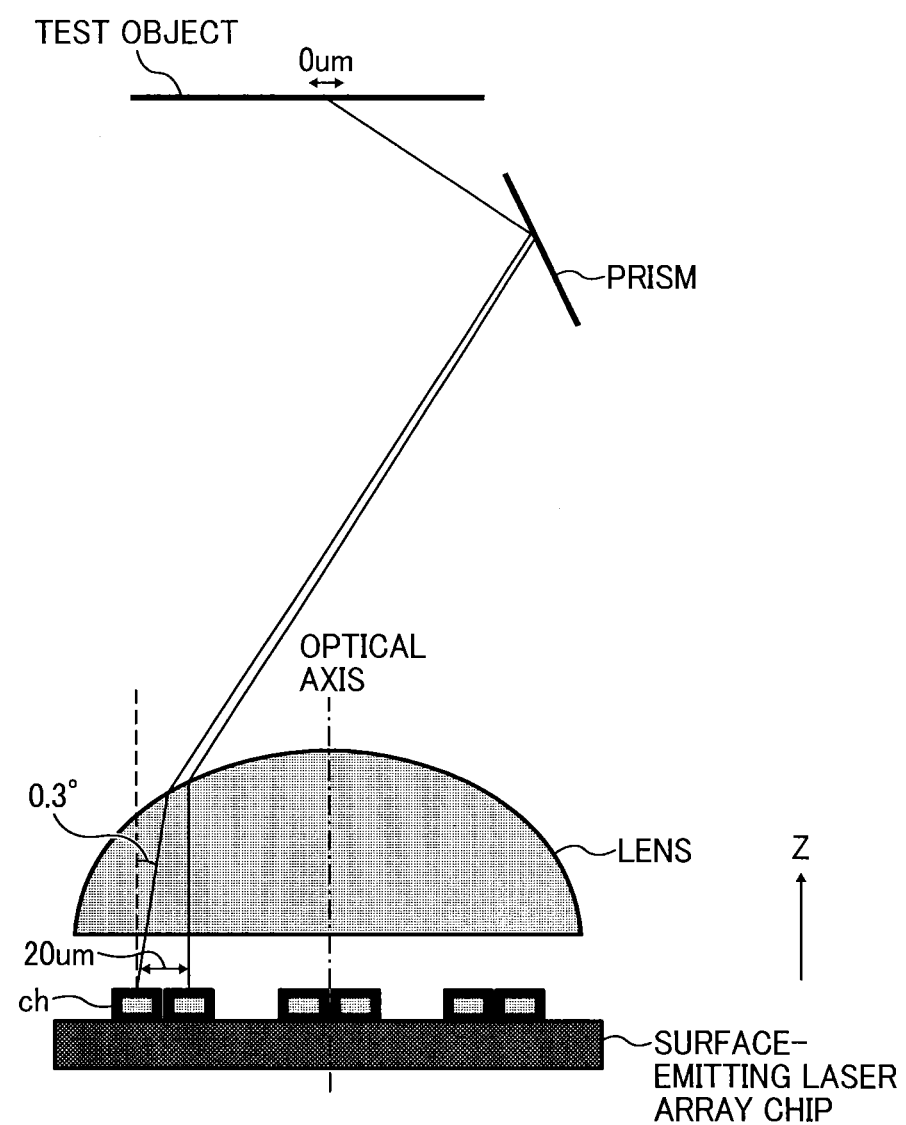
FIG. 31 is a diagram illustrating the operation of a light source module according to the first to third modifications of the second example.

FIG. 31 is a diagram illustrating the operation of a light source module according to the first to third modifications of the second example. As illustrated in FIG. 31 for example, when the light exit direction of the outermost channel in a surface-emitting laser array chip is inclined towards the optical axis of the lens by 0.3 [deg] with reference to the Z-axis (the optical axis of the lens) such that the light exit directions of the outermost channel and a channel (whose light exit direction is parallel to the Z-axis) adjacent to the outermost channel are not parallel to each other, the displacement of the positions at which the multiple rays of light emitted from these channels enter the test object via the lens and prism can be reduced (almost to 0 μm).

In other words, the displacement of the positions at which the two rays of light from the two channels enter the test object can be reduced by making one of the light exit directions of the two channels adjacent to each other in the periphery of the surface-emitting laser array chip become inclined towards the optical axis of the lens so as to get close to the other one of the light exit directions of the two channels.

By contrast, regarding the two channels that are adjacent to each other across the optical axis of the lens in the center area of the surface-emitting laser array chip (see FIG. 31), the two rays of exit light from these two channels are refracted by the lens so as to get close to each other even when the light exit directions of these two channels are parallel to the Z-axis (the optical axis of the lens). Accordingly, the displacement of the positions at which the two rays of light from the two channels enter the test object can be reduced without making one of the light exit directions of the two channels adjacent to each other become inclined towards the optical axis of the lens so as to get close to the other one of the light exit directions of the two channels. However, the displacement of the positions at which the two rays of light from the two channels enter the test object can further be reduced in the above case by making one of the light exit directions of the two channels adjacent to each other in the periphery of the surface-emitting laser array chip become inclined with reference to the Z-axis so as to get close to the other one of the light exit directions of the two channels. It is to be noted that in FIG. 31, the light emitted the center area of the surface-emitting laser array chip may directly enter the test object after passing through the lens (without being deflected by the prism).

As described above, in the first to third modifications, the displacement of the positions at which the multiple rays of light from a plurality of channels enter the test object can be reduced by making the light exit directions of the multiple channels of a surface-emitting laser array chip not parallel to each other. Accordingly, the sameness of the incident positions can be enhanced when the distance among the probes is reduced to dispose the probes with high density, and higher resolution can be achieved.

It is desired that the layout of the surface emitting laser array, the lens, and the prism be configured such that the optical paths of the rays of light emitted from at least two light-emitting units intersect near the exit end of the light source modules LM (near the surface of the test object). Note that these lays of light pass through the lens and then are reflected by the reflection member after being emitted from light-emitting units.

In the first to third modifications as described above, it is not necessary for the light exit directions of all the channels of the surface-emitting laser array chip to be not parallel to each other. Instead, it is satisfactory as long as the light exit directions of at least two channels of the surface-emitting laser array chip are not parallel to each other. Accordingly, it is satisfactory as long as the center point of the ring-shaped dielectric of at least one channel is displaced from the center point of the light exit area.

It is not necessary for the light exit areas of all the light-emitting units of the surface-emitting laser array chip to have a ring-shaped dielectric. Instead, a ring-shaped dielectric may be provided only for the light exit area of a light-emitting unit where the light exit direction is to be inclined with reference to the optical axis of the lens. The presence or absence of a ring-shaped dielectric at each channel may be determined by the design of a mask that is used for etching the protective layer 111.

A dielectric that is disposed at a light exit area is not necessarily properly ring-shaped. For example, at least some point of the ring shape of a dielectric intermittent may be broken, or a dielectric may be composed of a combination of a plurality of arcs with the same diameter (such arcs are concentric when viewed from the Z-axis direction). A dielectric that is disposed at a light exit area is not necessarily approximately ring-shaped, but it is satisfactory as long as the dielectric is approximately shaped like a frame.

Figure 32A:
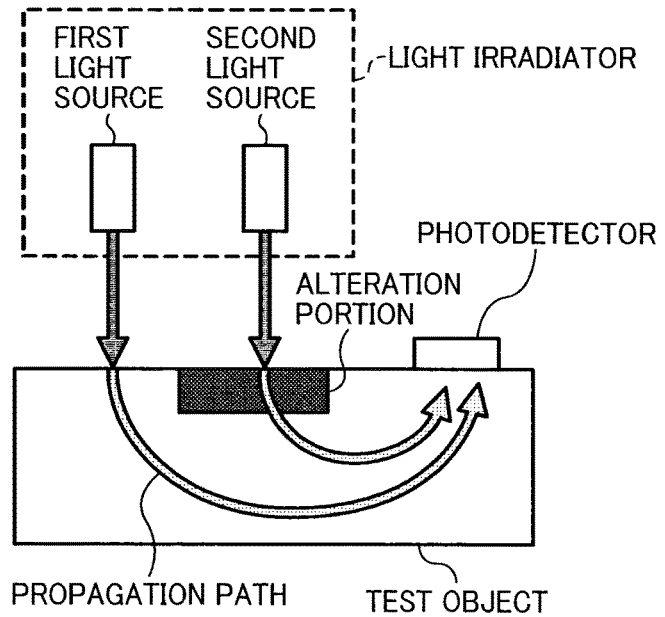
FIG. 32A is a diagram illustrating the operation of an optical sensor according to a control sample.

FIG. 32A is a diagram illustrating the operation of an optical sensor according to a control sample. In the light source module according to a control sample as illustrated in FIG. 32A where a plurality of rays of light that are parallel to each other enter a living body, an error occurs in the detection when an alteration portion is present near the surface of the living body. The term "alteration portion" indicates a portion with a special optical property, and includes, for example, roots of a hair and a colored skin. When such an alteration portion is present in the present control sample, the rays of light emitted from the first light source and the second light source, respectively, enter different positions of the test object. For this reason, there may be some cases in which, for example, only the light emitted from the second light source passes through the alteration portion. When the difference between the first light source and the second light source is calculated, such an alteration portion may cause a noise.

Figure 32B:
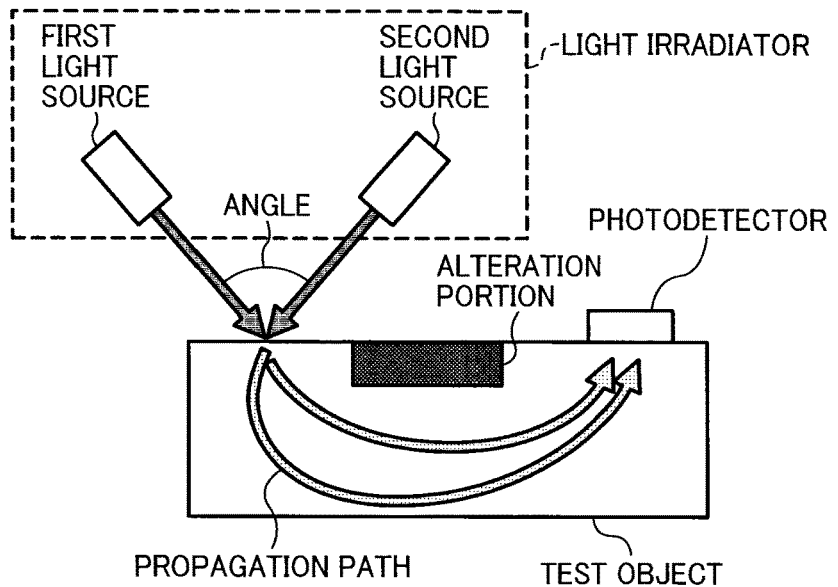
FIG. 32B is a first diagram illustrating the operation of an optical sensor according to the first embodiment of the present invention.

FIG. 32B is a first diagram illustrating the operation of an optical sensor according to the first embodiment. By contrast, in the present embodiment, as illustrated in FIG. 32B, the rays of light emitted from the first light source and the second light source, respectively, pass through the "same point" of the surface of the skin. Accordingly, when one of the rays of light emitted from the first light source and the second light source, respectively, pass through the alteration portion, the other one of the rays of light also passes through the alteration portion. In a similar manner, when one of the rays of light emitted from the first light source and the second light source, respectively, does not pass through the alteration portion, the other one of the rays of light also does not pass through the alteration portion. More specifically, the rays of light emitted from the first light source and the second light source, respectively, pass through the same optical path near the surface of the skin, and pass through different optical paths in a deeper portion. In other words, the configuration is insensitive to a difference near the surface of the skin, but is sensitive to a difference near the brain tissue. The resolution improves by reducing the noise near the surface of the skin.

In the second example, a transparent gel is dripped onto the window member provided for the housing such that the transparent gel intervenes between the window member and the surface of the test object and the air is removed.

In the conventional light source module, the light that is once radiated in the air enters the surface of the skin and propagates inside the body. In such configuration, a difference in refractive index arises between the refractive index 1.0 of the air and the refractive index 1.37 of a living body. As such a difference in refractive index arises, reflection and scattering occur. Moreover, the refractive index inside the living body in which the light propagates is smaller than that of the air outside the living body. For this reason, the propagation angle inside the living body becomes smaller than the incident angle. The refraction of light on the interface can be understood from the Snell laws of reflection. The Snell laws of reflection can be described by refractive indexes only.

Figure 33:
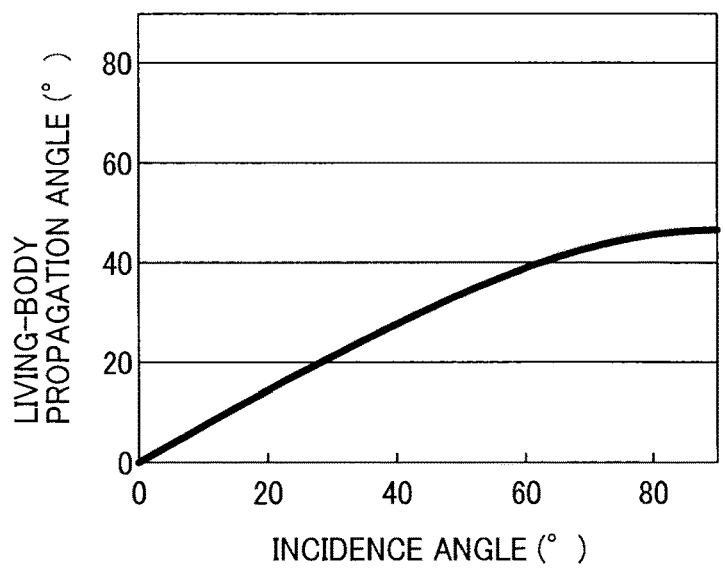
FIG. 33 is a graph illustrating the relation between the propagation angle inside the living body and the incident angle which a light forms with the surface of a living body when the light in the air enters the living body.

FIG. 33 is a graph illustrating the relation between the propagation angle inside the living body and the incident angle which a light forms with the surface of a living body when the light in the air enters the living body. More specifically, the relation (refraction of light) between the propagation angle inside the living body and the incident angle on the interface between the air on the on the light entering side (refractive index 1.0) and the living body on the propagation side (refractive index 1.37) is depicted by the graph in FIG. 33. As understood from FIG. 33, even when the incident angle of the light that enters the living body is 60 degrees, the propagation angle of the light that has entered the living body is reduced to degrees. Accordingly, even if a desired propagation angle of the light that has entered the living body is equal to or greater than 60 degrees, such a propagation angle cannot be achieved by the incident light from the air. In other words, it is difficult to form a propagation angle of large degree inside the living body from the light that has once released into the air.

Figure 34:
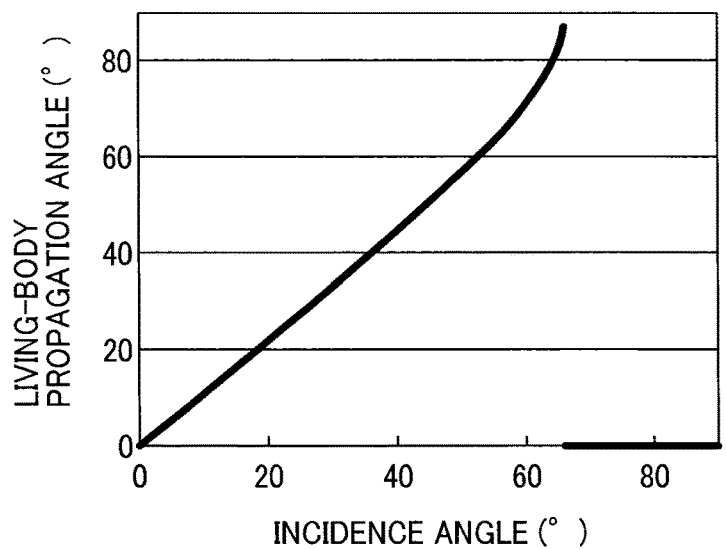
FIG. 34 is a graph illustrating the relation between the propagation angle inside the living body and the incident angle which a light forms with the surface of a living body when the light in the resin enters the living body, according to the second example of the first embodiment of the present invention.

In order to deal with such situation, in the second example, the refractive index of the transparent resin that makes up the window member of the light source module LM is designed to be greater than the refractive index 1.37 of the living body (for example, equal to or greater than 1.5). FIG. 34 is a graph illustrating the relation between the propagation angle inside the living body and the incident angle which a light forms with the surface of a living body when the light in the resin enters the living body, according to the second example of the first embodiment of the present invention. In this configuration, when the light is emitted from the light source module LM with the incident angle of 60 degrees, the propagation angle of the light that directly enters the living body becomes greater than 70 degrees inside the living body. When the angle is smaller in the design, the light source module LM can be downsized.

In the light source module LM according to the second example as described above, as illustrated in FIG. 16, the light that is emitted from the surface emitting laser in the direction parallel to the optical axis of the lens is refracted by the lens, and travels in a direction inclined by about 20 degrees with reference to the optical axis of the lens and enters the window member. The window member is designed to have the refractive index of about 1.5. The light that has passed through the lens is refracted when it enters the window member. However, such refraction is not large as the incident angle is not acute. The light that has entered the window member is deflected by the reflection plane of the prism, and travels in a direction inclined by about 55 degrees with reference to the optical axis of the lens. This angle of 55 degrees is the angle inside the window member of the refractive index 1.5, and as illustrated in FIG. 34, the propagation angle inside the living body (of the refractive index 1.37) is about 60 degrees.

In order for the light emitted from the light source module LM to propagate inside a pseudo living body in a direct manner, it is necessary to remove the airspace that exists in the interface between the pseudo living body and the light source module LM. In the present embodiment, transparent gel is used to remove such airspace. The transparent gel used here is aqueous glycerin solution that goes well with pseudo living body. The volatility of the transparent gel is controlled so as not to evaporate during the inspection while the light source module LM is closed by a lid, and the volatility of the transparent gel is controlled so as to evaporate or soak into the pseudo living body at an appropriate timing after the inspection is done. The optical property of the transparent gel is controlled to become transparent near the wavelength of 780 nm, and the refractive index is adjusted to be close to that of the surface of pseudo living body. In the present example, the refractive index is adjusted to be about 1.37. Due to this adjustment, the difference in refractive index on the bumps and dips of the surface of the pseudo living body can be attenuated, and a state of no reflection can be achieved. Accordingly, the reflection on the surface of the pseudo living body can be almost eliminated. There are physical bumps and dips on interface with the pseudo living body, but there is no optical bumps and dips. Accordingly, no scattering occurs. As a result, the light emitted from the light source module LM can precisely be propagated inside the pseudo living body in an appropriate propagation direction according to the exiting angle. As known in the art, the propagation inside the pseudo living body causes scattering strongly. However, the scattering on the surface of the skin is not small. According to the configuration as described above, the anisotropy of the light can be secured to a large degree. As the anisotropy can be secured to a large degree, the incident angles of the multiple rays of light emitted from the light source module LM on the pseudo living body can be varied widely, and as will be described later, the incident angles at which the multiple rays of light enter the detection module DM can be varied widely.

Figure 35:
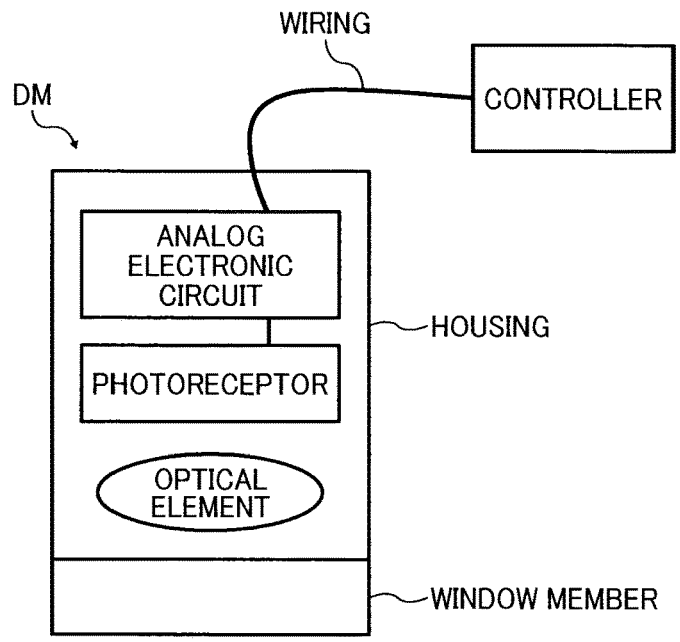
FIG. 35 is a first diagram illustrating an outline of the configuration of a detection module according to the second example of the first embodiment of the present invention.

FIG. 35 is a first diagram illustrating an outline of the configuration of a detection module according to the second example of the first embodiment of the present invention. As illustrated in FIG. 35, the detection module DM includes the housing, an optical element, a photoreceptor, a flexible circuit board on which an analog electronic circuit is mounted, a wiring connected to the flexible circuit board, and a connector.

Figure 36:
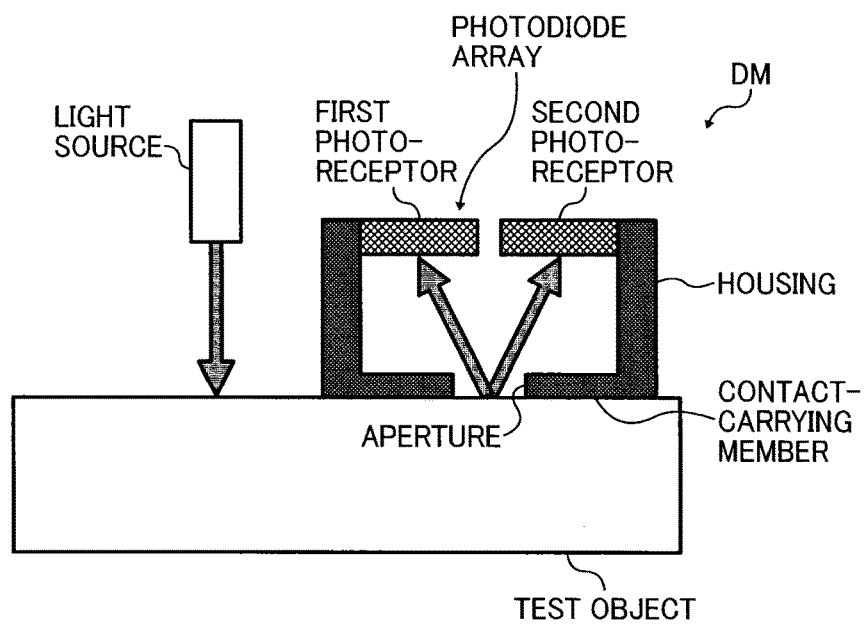
FIG. 36 is a second diagram illustrating an outline of the configuration of a detection module according to the second example of the first embodiment of the present invention.

FIG. 36 is a second diagram illustrating an outline of the configuration of a detection module according to the second example of the first embodiment of the present invention. As illustrated in FIG. 36, in the detection module DM, the light that is emitted from the light source to the pseudo living body propagates inside the pseudo living body, and the light is split into a plurality of rays of light and are guided to a plurality of photoreceptors.

In the related art (see, for example, JP-2011-179903-A), in the DOT making use of fluorescence, a photoreceptor is arranged in accordance with a plurality of rays of light emitted from a test object with varying angles. However, in this arrangement of a photoreceptor, the light of all the exiting angles from the test object enters the photoreceptor.

By contrast, the detection module DM according to the present embodiment separately detects the split rays of light that have entered the test object at the "same point". As described above in regard to the light source module LM, the detection module DM can be designed when an optical simulation is performed. For this reason, a difference in position in the order of millimeter is no object in the precision of the "same point".

Figure 37:
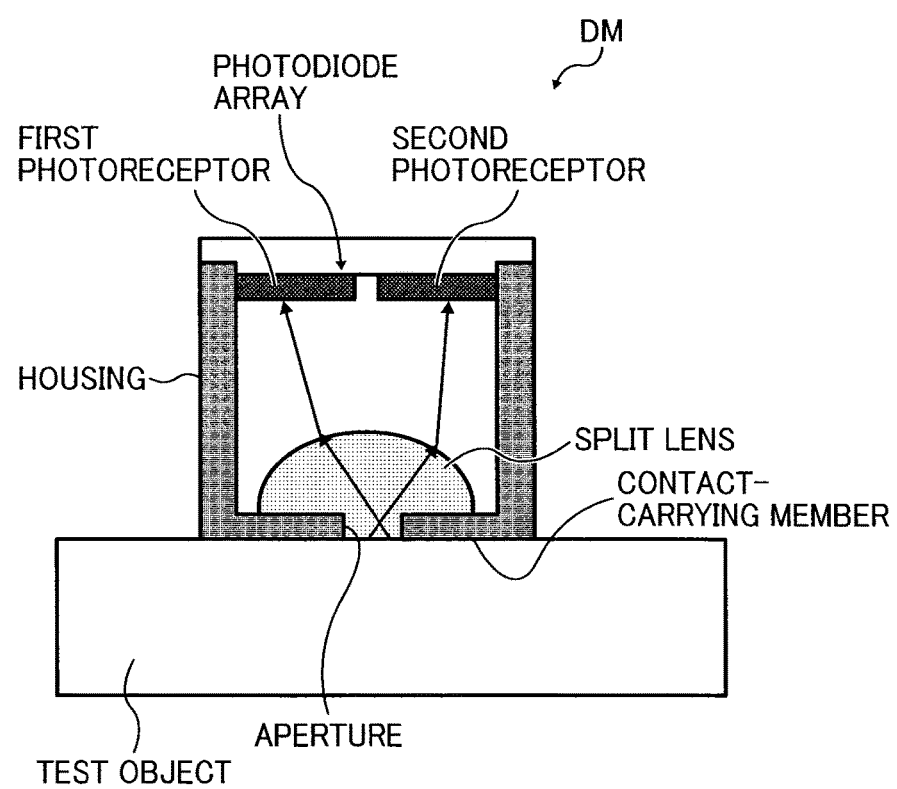
FIG. 37 is a third diagram illustrating an outline of the configuration of a detection module according to the second example of the first embodiment of the present invention.

Next, the detection module DM is described in detail. As illustrated in FIG. 37, the detection module DM includes a black-resin housing, a contact-carrying member consisting of an elastic body attached to a front end of the housing, a transparent split lens accommodated in the housing, and four photoreceptors. The housing has apertures at the front end of the housing and at the other end of the housing in contact with the contact-carrying member.

In the present embodiment, black rubber is used for the contact-carrying member in order to enhance the imperviousness to light. From the aperture of the contact-carrying member, a center portion (about φ1 mm) of the split lens stick out by about several hundreds of micrometers to the outside of the housing. As this portion contacts the surface of the living body, no air optically exists therein. Accordingly, refraction of Fresnel or scattering is prevented.

The stability of the detection module DM also further improves when the above-described transparent gel is used. Accordingly, the transparent gel is used for the detection module DM. The split lens is composed of a transparent resin, and its refractive index is about 1.8. The split lens is attached to the housing.

The aperture is a circular hole with the size of about 1 mm that penetrates the leading end and the contact-carrying member of the housing, and serves to limit the position of the light that propagates inside the test object and exits from the test object. The rays of light that exit from the aperture are oriented to a plurality of different directions. The incident positions are determined by the aperture, and then the incident light is split into a plurality of rays of light by the split lens. Accordingly, these multiple rays of light can separately be detected.

Note that the aperture implements the configuration that the rays of light exiting from the test object enter the photoreceptor from the "same point" as described above.

The rays of light that have passed through the aperture are refracted into different directions by the split lens according to the propagation directions of these rays of light. Accordingly, the positions at which the rays of light enter the photoreceptor are different from each other.

The split lens is a spherical lens, and has an about 3 mm diameter and an about 3 mm focal length f. In the second example, the number of the partitions of the light by the split lens is four, and a photodiode array having four two-dimensionally arranged photoreceptors (photodiodes) is used. Note that in FIG. 37, only two of the four photoreceptors (photodiodes), i.e., the first and second photoreceptors, are illustrated.

In the present example, the photodiode array has a square shape where the sides have about 3 mm length, and each of the photodiodes has a square shape where the sides have 1.4 mm length. As illustrated in FIG. 37, an angle $\theta 2$ is defined, and the distance between the photodiode array and the aperture is about 5 mm.

One side of the lens is planar, and the other side of the lens is spherical. The planar side contacts the pseudo living body. As the position of the aperture is displaced from the focal point of the lens, the lens cannot form parallel light rays. The lens is used to limit the light that enters the photodiode array.

A simplified optical simulation is performed on this optical system, and the following result is obtained. The light with approximately $-10°<\theta 2<50°$ enters the second photoreceptor, and the light with approximately $-50°<\theta 2<10°$ enters the first photoreceptor. In other words, the light that has propagated inside the pseudo living body and exited from the aperture is split into a plurality of rays of light according to the exiting angles, and each of these multiple rays of light enters one of the four photoreceptors.

In the second example, a spherical lens is used for the split lens. However, an aspherical lens may be used for the split lens to widen the angle of detection. The split accuracy and the number of partitions correlates with the estimation accuracy of an inverse problem as will be described later. For this reason, an optical system is determined by a desired level of estimation accuracy. In the present embodiment, a spherical lens is adopted and the number of partitions is four.

The photodiodes are electrically wired, and are connected to an operational amplifier. A semiconductor operational amplifier is used for the operational amplifier, and the operational amplifier supplies source voltage of 5 volts. As the detectable amount of light is very small, the amplification factor of the operational amplifier is high, and two-stage amplification is adopted. The amplification factor of about five digits is applied in the first stage, and the amplification factor of about three digits is applied in the second stage.

Figure 38:
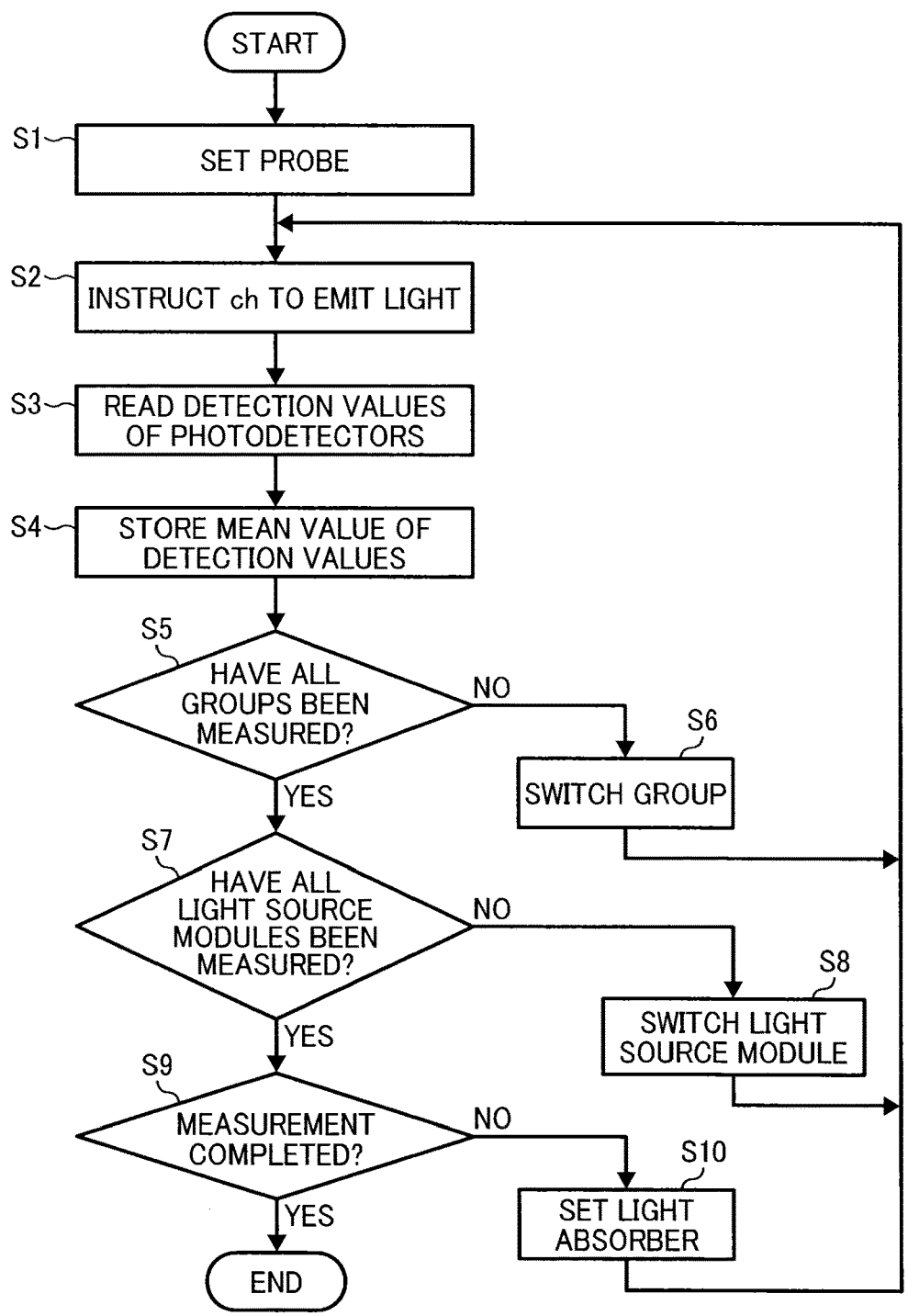
FIG. 38 is a flowchart of a method of detecting an optical property (position measuring method) according to the second example.

FIG. 38 is a flowchart of a method of detecting an optical property (position measuring method) according to the second example. The method of measuring the position of the light absorber in the pseudo living body (method of detecting an optical property of the test object) according to the second example is described with reference to the flowchart depicted in FIG. 38.

Firstly, the probes (i.e., the light source modules LM and the detection modules DM) are set (inserted) into the pseudo living body (step S1). In so doing, a transparent gel is applied to between the acrylic watertank and each of the probes, and each of the probes is carefully set to a position determined by a fixation member so as not to mix a bubble in the transparent gel. The number of the probes is sixteen including eight light source modules LM and eight detection modules DM, and the light source modules LM and the detection modules DM are alternately arranged in a grid pattern with equal pitches (see FIG. 15). The pitch in the grid pattern (space among points of the grid pattern) is 30 mm, and the space between each of the light source modules LM and detection modules DM is 30 mm.

In this state, desired one of the channels of the light source module LM is instructed to emit light (step S2). The light source module LM is instructed to emit light on a group-by-group (4ch) basis, and the light-emission intensity is determined such that the current value becomes about 4 mW. The light emitting period is about 10 msec, and the detection values of all the photodiodes are read during the light emitting period, and the pieces of data (detection values) obtained at 1 msec intervals are averaged (step S3). Then, the averaged detection value is stored in the storage unit (step S4). In a similar manner, the 10 msec light emission, the measurement, and the data storage are repeated for the next group (steps S5, S6, and S2 to S4). Note that in each one of the light source modules LM, in a similar manner, the light emission of the four channels of the surface-emitting laser array chip of the oscillation wavelength of 780 nm and the light emission of the four channels of the surface-emitting laser array chip of the oscillation wavelength of 900 nm are performed in sequence.

However, in the data processing described below, the two wavelengths are treated in almost the same way. Accordingly, in the present embodiment, the measurement performed with two varying wavelengths is equivalent to the repeated measurement at the same position. When the changes in the real bloodstream are detected, the difference between the two wavelengths is used for the detection of oxyhemoglobin and reduced hemoglobin in a separate manner. However, in the present embodiment, measurement is performed one time using two surface-emitting laser array chips with varying oscillation wavelengths. Accordingly, the noise due to the variations in chips can be reduced.

After the light emission and measurement of all the groups of one of the light source modules LM are completed, the light emission of the next light source module LM is performed (steps S7, S8, and S2 to S4). In a similar manner to the above, the light source module LM is instructed to emit light sequentially on a group-by-group (4ch) basis. After the light emitting and measurement of all the light source modules LM are completed, a light absorber is set (steps S9 and S10). In order to set the light absorber at a desired position precisely with high reproducibility, an optical stage is used. After the light absorber is set as described above, the steps from the light emission of the channels to the storage of the detection values of the photodiodes are performed again (steps S2 to S9). The stored data is labeled as r(s, i, n) (i=1, 2, 3, . . . M; n=1, 2, 3, . . . K) with the light absorber and r(0, i, n) (i=1, 2, 3, . . . , M; n=1, 2, 3, . . . , K) without the light absorber. "i" denotes the numbers assigned to the respective detection modules DM. "n" denotes the numbers assigned to the respective groups. Next, the difference Δr (i, n) is calculated.

The method of calculating the position of the light absorber (the optical property of the pseudo living body) according to the result of the measurement obtained by the measurement method as described above is similar to the method of calculating the position of the light absorber (the optical property of the pseudo living body) according to the result of the measurement obtained by the measurement method as described above with reference to the flowchart of FIG. 8, and thus its description is omitted.

Figures 39, 40:
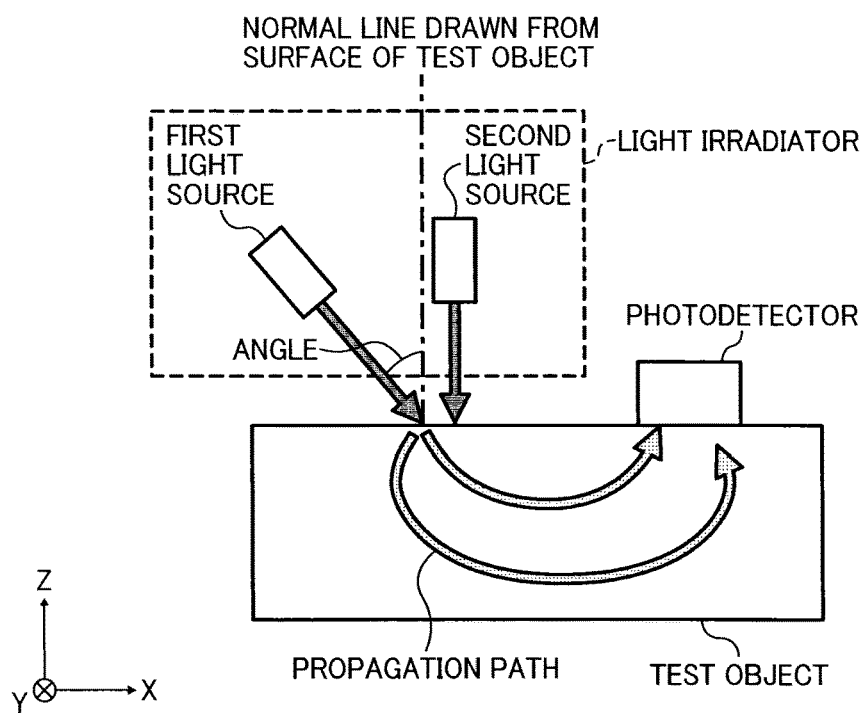
FIG. 39 is a diagram depicting the result of an inverse problem estimation according to the second example of the first embodiment of the present invention.
FIG. 40 is a second diagram illustrating the operation of an optical sensor according to the first embodiment of the present invention.

FIG. 39 is a diagram depicting the result of an inverse problem estimation according to the second example of the first embodiment of the present invention. As a result, the result of estimation as illustrated in FIG. 39 can be derived. FIG. 39 also depicts, as a control sample, the results of the detection in which only the center one of the five groups of the surface-emitting laser array chip (see FIG. 17) is controlled to emit light and the detection value of only one of the four photodiodes of the photodiode array is used. In the other respects, the numeric values are all processed in the same way as the present embodiment. The configuration of this control sample is almost equivalent to that of the conventional NIRS DOT device. By contrast, in the present embodiment, the Bayes estimation is adopted as described above, and both the position and depth of the light absorber are detectable. In the results depicted in FIG. 39, a circular sign is given for a case where the position of the light absorber is successfully detected. In the present embodiment, as the distance in the depth direction of the light absorber (i.e., the Z-axis direction in FIG. 10) becomes longer, the distance to the light source module LM becomes longer, and the amount of the light that can propagate decreases. For this reason, as the depth of the position of the light absorber becomes deeper, it becomes more difficult to perform detection successfully. In the present embodiment, detection was successful up to the depth of about 16 mm. In the control sample, a known NIRS DOT device is used, and the detection in the depth direction was not successfully performed even with the application of the Bayes estimation. In order for the DOT to detect the three-dimensional position including the depth of the light absorber with high accuracy, the layout of probes with high density is required as known in the art. However, in the present embodiment, with the layout of probes with low density, the three-dimensional position of the light absorber was successfully detected with high accuracy.

As described above, the optical sensor 10 according to the present embodiment (the first and second examples) includes an irradiation system including a plurality of light source modules LM (light irradiators) to irradiate a test object (pseudo living body) with light, and a detection system that detects the light that is emitted from the irradiation system and propagated inside the test object. Then, each of the multiple light source modules LM emits multiple rays of light that are not parallel to each other to the same point of the test object. FIG. 40 is a second diagram illustrating the operation of an optical sensor according to the first embodiment. In the above configuration, as illustrated in FIG. 40, the multiple rays of light that are not parallel to each other, which are emitted to the same point of the test object (scatterer), have different incident angles with reference to the test object, and take varying propagation paths.

Accordingly, the amount of information obtained for the inside of the test object increases, and higher resolution can be achieved. Moreover, as the resolution is improved, the density of the probes (i.e., the number of probes for each unit of dimension) can be reduced for the same desired resolution. Accordingly, the attachability improves.

Accordingly, the optical sensor 10 can achieve higher resolution without degrading the attachability to the test object.

Note that the multiple rays of light that are not parallel to each other but enter the same point of the test object indicates that the multiple rays of light form angles with each other. In other words, as there exist angles formed by the multiple rays of light, the propagation paths of the multiple rays of light in the test object can be varied. By contrast, if the multiple rays of light that enter the same point of the test object are parallel to each other (for example, if the multiple rays of light are parallel to the normal line to the surface of the test object), the propagation paths of the multiple rays of light in the test object become the same.

The light source module LM according to the first to third modifications of the second example includes a surface-emitting laser array chip having a plurality of light-emitting units (channels), and a lens disposed in the optical path of a plurality of rays of light emitted from the multiple light-emitting units, where the light exit directions of at least two of the multiple light-emitting units are not parallel to each other.

In such configuration, the displacement of the positions at which the multiple rays of light from a plurality of channels enter the test object can be reduced. Accordingly, the probes (i.e., the light source modules LM and the detection modules DM) can be disposed with high density, and the resolution further improves.

Each of the multiple light-emitting units has a ring-shaped dielectric at the light exit area, and the center point of the ring-shaped dielectric of at least one of the multiple light-emitting units is displaced from the center point of the light exit area. Accordingly, the light exit direction can be controlled with improvement in the beam quality of the exit light.

The light exit direction of at least one of the light-emitting units is oblique with reference to the optical axis of the lens. Accordingly, the refraction direction (direction of travel) from the lens becomes adjustable.

Among at least two of the light-emitting units, relative positions of the center point of the dielectric and the center point of the light exit area are different from each other. Accordingly, the light exit directions of at least two of the light-emitting units can reliably be made not parallel to each other.

The optical paths of the rays of light between at least two of the light-emitting units and the lens gradually get close to each other. Accordingly, the optical paths of the rays of light that are emitted from at least two of the light-emitting units can further be made close to each other by the lens (see FIG. 31).

The light source module LM includes a prism, and the prism is disposed on the optical path of the light that is emitted from at least two of the light-emitting units and passes through a lens. Moreover, the prism has a reflection plane that reflects the light towards the test object. Accordingly, the light can be guided to the same point of the test object.

The light source module LM according to the present embodiment includes a surface emitting laser array having a plurality of surface emitting lasers (light-emitting units), and a convex lens disposed in the optical path of a plurality of rays of light emitted from the surface emitting lasers to form a plurality of rays of light that are not parallel to each other. The distance between the surface emitting laser array and the principal point of the convex lens does not match the focal length of the convex lens.

Accordingly, the return light can be prevented from concentrating on the surface emitting laser, and the fluctuations in the output of the surface emitting laser can be prevented. As a result, the amount of the light emission of the surface emitting laser can be stabilized, and the accuracy of detection of the optical sensor 10 improves. Further, the resolution of the NIRS can be improved.

By contrast, if the surface emitting laser array is at the focal point of the convex lens, the light reflected from an external reflection plane is concentrated onto the surface emitting laser by the convex lens, and the laser oscillation becomes unstable. This phenomenon is called, for example, return light or self-mixing. If this phenomenon occurs when a surface emitting laser array is used as the light source of an optical sensor, the amount of the light emission becomes unstable. See JP-2011-114228-A and JP-2012-132740-A for the detail. The space between the convex lens and the surface emitting laser array is filled with a transparent resin whose refractive index is equivalent to that of the convex lens.

As a result, the refractive index does not change at the boundary of the interface between the convex lens and the surface emitting laser array, and the return light can be prevented. As a result, the amount of the light emission of the surface emitting laser array can be stabilized, and further, the resolution of the NIRS can be improved.

The detection system includes a plurality of detection modules DM each of which includes a plurality of photoreceptors (photodiodes) configured to receive the multiple rays of light separately that are emitted from the light source module LM to the test object and have propagated inside the test object.

In this configuration, the two items of data of two different propagation paths inside the test object can separately be obtained.

The detection module DM is disposed between the test object and a plurality of photoreceptors (photodiodes), and has the housing and the contact-carrying member on which an aperture is formed. Moreover, some of each of the multiple rays of light that have propagated inside the test object passes through the aperture.

In this configuration, the light can be taken into the housing from the same point of the test object. More specifically, only rays of light with limited incident angles enter the housing. Accordingly, each of a plurality of photoreceptors can receive light.

Moreover, the detection module DM includes the split lens (light-receptive lens) that separately guides some of the multiple rays of light passed through the aperture to the multiple photoreceptors.

In this configuration, some of each of the multiple rays of light passed through the aperture can separately enter the multiple photoreceptors with a stable amount of light.

The light source module LM includes a window member that contacts the test object and is composed of a material (transparent resin) whose refractive index is greater than that of the test object. Accordingly, the propagation angle (refraction angle) of the light inside the test object can be increased with reference to the incident angle on the test object. As a result, compared with cases in which, for example, the light in the air enters the test object, the propagation angle can be increased even with the same degree of incident angle. Accordingly, the difference in propagation angle between the two rays of light inside the test object becomes larger than the difference in incident angle between the two rays of light that enter the same point of the test object with varying incident angles, and the propagation paths of the multiple rays of light in the test object can be varied significantly. As a result, an even higher resolution can be achieved.

The light source module LM includes a plurality of two-dimensionally disposed surface emitting lasers and an irradiation lens (lens) disposed in the optical path of a plurality of rays of light emitted from the multiple surface emitting lasers.

In this configuration, the directions of travel of the rays of light emitted from the multiple surface emitting lasers can be changed to desired directions (i.e., the directions towards the positions at which the corresponding prisms are disposed).

Moreover, the light source module LM includes a prism (reflection member) disposed on the optical path of the light that has passed through the irradiation lens, and the prism reflect the light towards a prescribed direction.

In this configuration, the direction of travel of the light emitted through the irradiation lens can further be changed to a desired direction. In other words, the incident angle on the test object can be designed to a desired angle.

As described above, the optical sensor 10 is an optical sensor with a relatively simple configuration that effectively utilizes the anisotropy of the propagation of light to achieve high resolution. It is expected that the optical sensor 10 to be applied to various kinds of fields such as the field of the DOT.

The optical inspection device 1000 includes the optical sensor 10, and a controller (optical property calculator) that calculates the optical property of the test object based on the detection results of the optical sensor 10.

In this configuration, the accuracy of the detection at the optical sensor 10 is high, and thus the optical property of the test object can be calculated with high accuracy.

Second Embodiment

Next, a second embodiment of the present invention is described. In the present embodiment, a method of adapting the probes described above in the first embodiment to an actual human body is described. In the present embodiment, the test object is changed from the phantom (the watertank filled with whitish water) to the head of a human body, and the light absorber is changed to the bloodstream in the brain.

In the present embodiment, the distribution of the bloodstream inside the brain is to be estimated with high accuracy. In the present embodiment, a test subject (test object) is measured and the shape is modeled based on the obtained data, and then the Monte Carlo simulation is performed. Further, the magnetic resonance imaging (MRI) is used to measure the shape of the head of the test subject. More specifically, the shapes of the four sites of the head including the scalp, the skull, the cerebrospinal fluid, and the cerebral cortex are measured from the images.

Such three-dimensional data is required for high-precision detection. However, such three-dimensional data may be substituted, for example, by the data of a model brain of standard shape. For each of the sites, a normal scattering coefficient, anisotropy, and absorption coefficient are known, and thus these known values are used. The probes are precisely attached to the head by fixtures, and the attached positions are also precisely measured. The configuration of elements such as the probes is equivalent to that of the first embodiment as described above, and thus the overlapping description is omitted here. An optical simulation is performed using the accurate shapes and the layout of the elements and the values of the sites.

Figure 41:
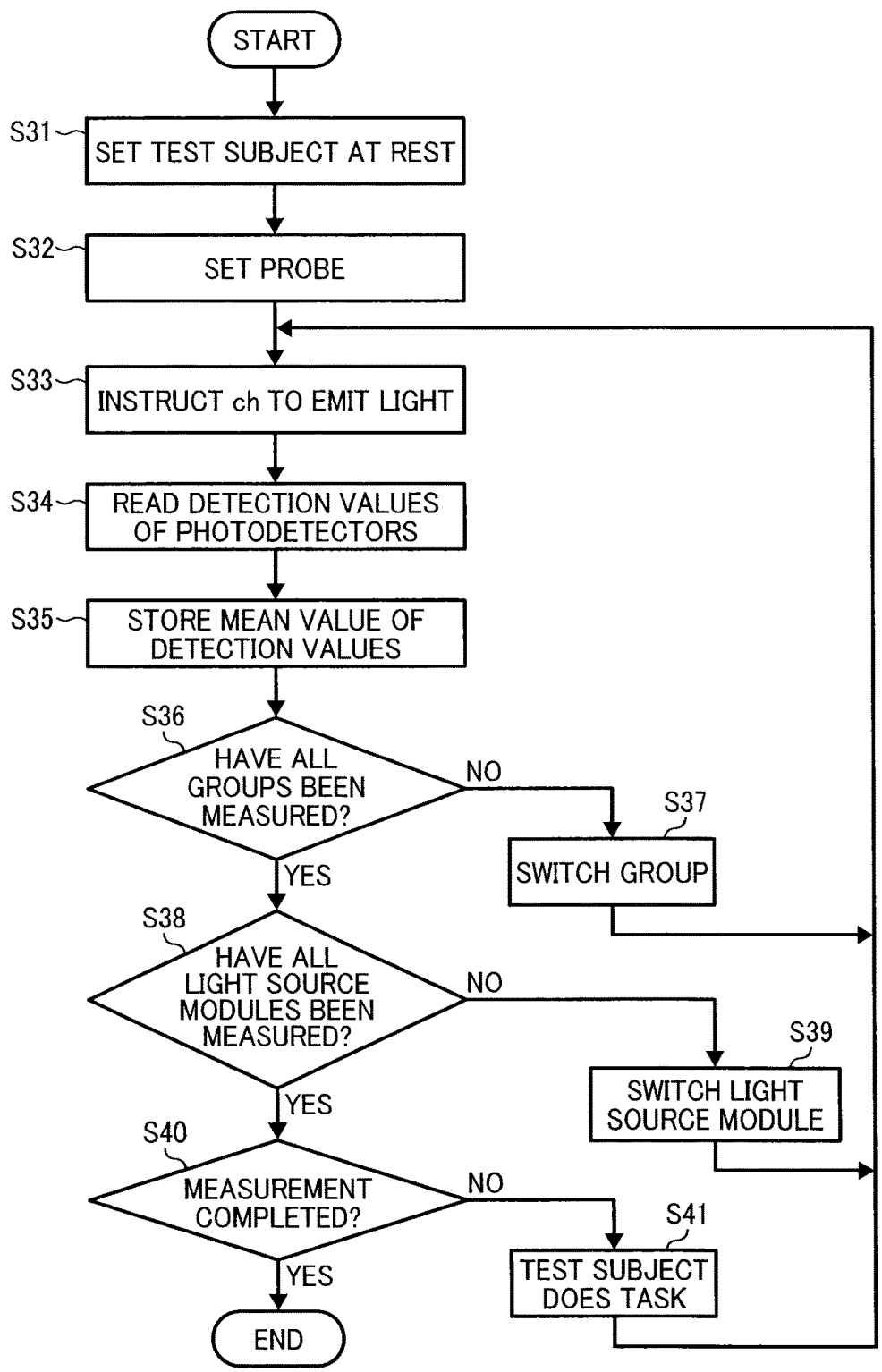
FIG. 41 is a flowchart of a method of detecting an optical property (position measuring method) according to a second embodiment of the present invention.

FIG. 41 is a flowchart of a method of detecting an optical property (position measuring method) according to the second embodiment. In the following description, a method of measuring the bloodstream inside the brain is described below with reference to the flowchart of FIG. 41. Firstly, the test subject is set at rest (step S31), and the probes (the detection module DM and the light source module LM) are set to the head. In so doing, each of the probes is carefully set (disposed) to a prescribed position using a fixation member so as not to clamp a hair or the like between the probe and the scalp. In this state, the channels of the light source module LM are instructed to emit light (step S33). The light source module LM is instructed to emit light (emit pulses of light) on a group-by-group basis, and the light-emission intensity is determined such that the current value becomes about 4 mW. The light emitting period is about several milliseconds, and the detection values of all the photodiodes are read and averaged during the light emitting period (step S34). Then, the averaged detection value is stored in the recording medium (step S35).

In a similar manner, the light emission of several milliseconds, the measurement, and the data storage are repeated for the next group (steps S36, S37, and S33 to S35). After the light emitting and measurement of all the light source modules LM are completed, the test subject is asked to do a task (steps S38 to S41). In the present embodiment, a commonly-used language fluency task is used. For such a language fluency task in detail, see JP-2012-080975-A.

While such a task is being done, the brain is activated, and a cerebral blood flow occurs only at the activated site. The bloodstream includes oxyhemoglobin and reduced hemoglobin, and light absorption occurs due to the bloodstream. An inverse problem estimation using the Bayes estimation or the like has already been described with reference to the first embodiment, and thus its description is omitted. The accuracy of the location of the bloodstream obtained in the present measurement can be checked by the measurement using the functional Magnetic Resonance Imaging (fMRI). The fMRI is one method of visualizing the dynamic response of the bloodstream related to the activities of the brain or spinal cord of human beings or animals, using the MRI. Due to the check of the measurement using the fMRI, the measurement using the optical sensor according to the present embodiment is found to have high resolution.

Third Embodiment

Next, a third embodiment of the present invention is described. In the third embodiment, the light source modules LM and detection modules DM that are equivalent to those of the first embodiment as described above are used for probes, and the layout of the probes is different from the other embodiments. Other than the layout of the probes, the configuration of the third embodiment is equivalent to that of the first embodiment as described above, and thus the overlapping description is omitted here.

Figure 42:
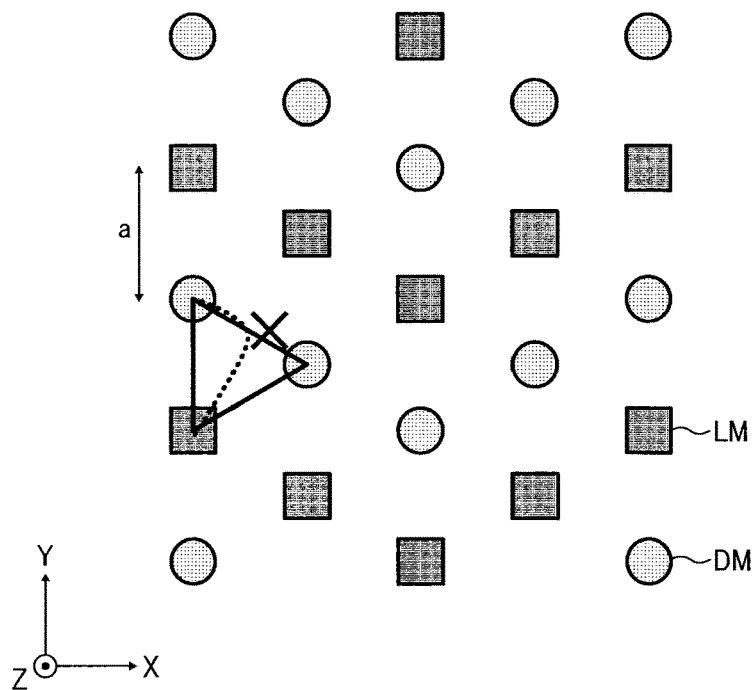
FIG. 42 is a diagram illustrating the arrangement of a plurality of light source modules and a plurality of detection modules in an optical sensor according to a third embodiment of the present invention.

In the second example of the first embodiment as described above, as illustrated in FIG. 15, two detection modules DM and two light source modules LM are disposed such that each of them is at the vertices of a roughly-drawn square. However, in the above layout, the optical path between each of the light source modules LM and detection modules DM becomes long at a point indicated by "X" in FIG. 15. For this reason, there is some concern that the amount of light received by the detection module DM is insufficient and the accuracy of detection may deteriorate due to the increased noise at that point. In order to deal with such situation, the layout of probes has been diligently studied, and it is found that the layout as illustrated in FIG. 42 is optimal. In FIG. 42, the multiple light source modules LM and detection modules DM are disposed for a test object such that two of either one of the light source modules LM and the detection modules DM are at two vertices of a regular triangle separately and one of the other one of the light source modules LM and the detection modules DM is at the remaining vertex of the regular triangle.

Here, for the purpose of simplification, the longest distances between the light source module LM and the detection module DM are compared with each other. Note that it is assumed that the space (pitch) between each of the light source modules LM and detection modules DM is "a". At the position of "X" in FIG. 15, the distance indicated by the broken lines is $\sqrt{2}a$ (about 1.414a). By contrast, the position of "X" in FIG. 42, the distance indicated by the broken lines is $(1+\sqrt{3})/2$ (about 1.366a). In short, when the longest distances between the light source module LM and the detection module DM are compared with each other between the two layouts of the probes in FIG. 15 and FIG. 42, the layout of the probes illustrated in FIG. 42 is shorter and thus is more desirable.

An inverse problem estimation was performed in the layout of the probes of FIG. 42 in a similar manner to the first embodiment, and as a result, it was found that the detectable area is widened in the layout of the probes according to the present embodiment.

Fourth Embodiment

Next, a fourth embodiment of the present invention is described. In the fourth embodiment, the layout of the multiple light source modules LM and multiple detection modules DM equivalent to that of the first embodiment as described above is adopted, and the layout of the channels of the light source module LM and the layout of the photodiodes of the detection module DM are different from those of the other embodiments. Other than the layout of the channels and photodiodes, the configuration of the third embodiment is equivalent to that of the first embodiment as described above, and thus the overlapping description is omitted here.

As illustrated in FIG. 15, in the second example of the first embodiment as described above, the multiple light source modules LM and detection modules DM are disposed for a test object such that the light source module LM and the detection module DM are arranged so as to be next to each other in both the X direction and the Y direction that are orthogonal to each other.

However, as described above, in the above layout, the optical path between each of the light source modules LM and detection modules DM becomes long at the point indicated by "X". For this reason, there is some concern that the amount of light received by the detection module DM is insufficient and the accuracy of detection may deteriorate due to the increased noise at that point.

Figure 43:
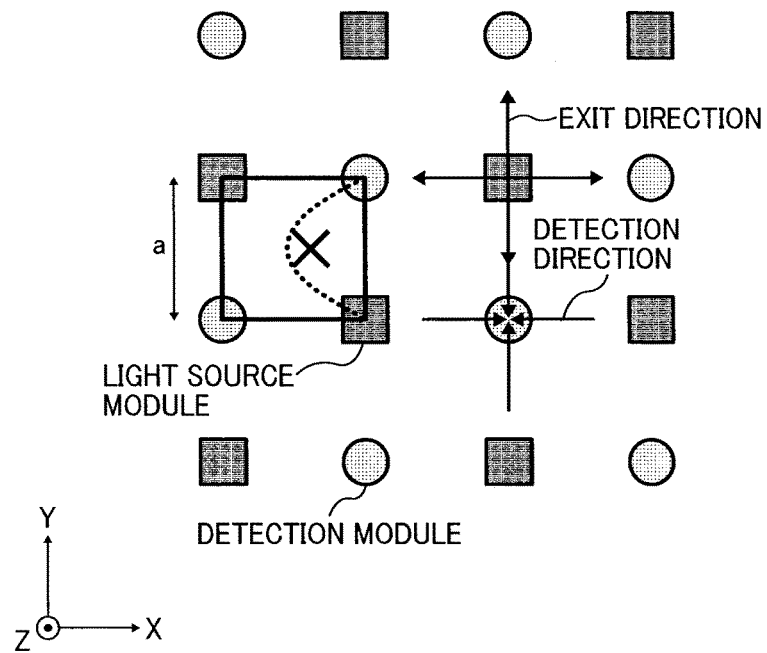
FIG. 43 is a diagram illustrating the light exit directions of a plurality of light source modules and the detection directions of a plurality of detection modules in an optical sensor according to a control sample.

FIG. 43 is a diagram illustrating the light exit directions of a plurality of light source modules and the detection directions of a plurality of detection modules in an optical sensor according to a control sample. In the control sample illustrated in FIG. 43, the multiple light source module and the multiple detection module are arranged for the test object so as to be next to each other in both the X direction and the Y direction that are orthogonal to each other, and both the light exit directions and the detection directions (i.e., the direction at which the light enters the photoreceptor) are parallel to the X direction and the Y direction. The lens that is disposed near the surface emitting laser has an optical property of point symmetry. Accordingly, the light exit directions depend on the position of the surface emitting laser and the position of the group. As the lens that has an optical property of point symmetry, the detection directions depend on the division layout of the photodiode array.

Figure 44B:
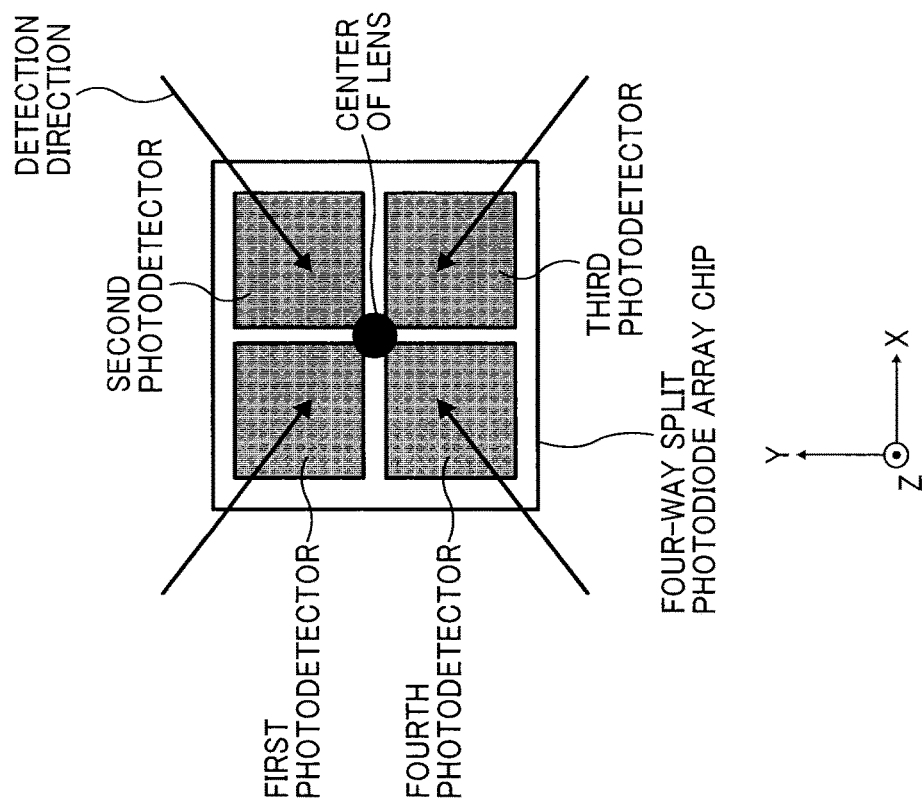
FIG. 44B is a diagram illustrating the detection directions of the four photodiodes of a photodiode array according to the fourth embodiment of the present invention.
Figure 44A:
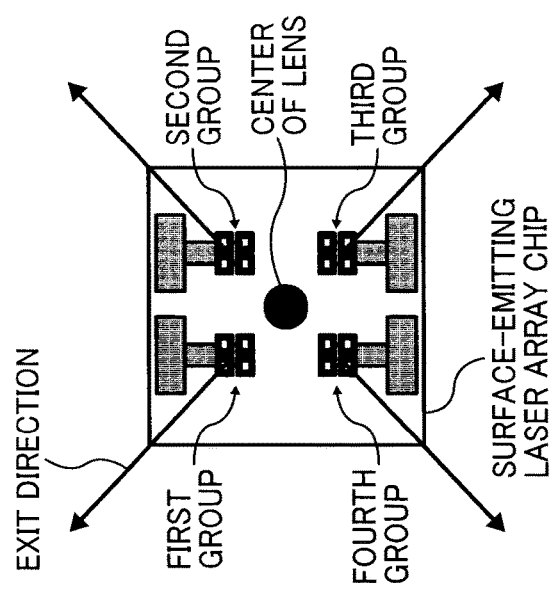
FIG. 44A is a diagram illustrating the light exit directions of the four groups of a surface-emitting laser array chip according to a fourth embodiment of the present invention.
Figure 45:
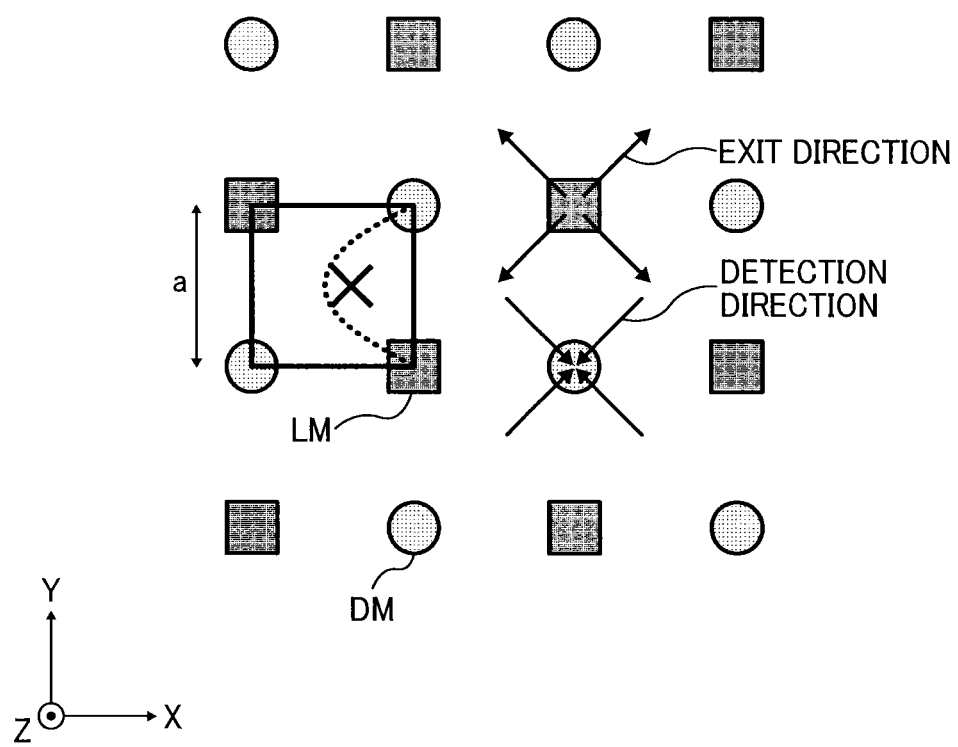
FIG. 45 is a diagram illustrating the light exit directions of a plurality of light source modules and the detection directions of a plurality of detection modules in an optical sensor according to the fourth embodiments of the present invention.

FIG. 44A is a diagram illustrating the light exit directions of the four groups of the surface-emitting laser array chip according to the fourth embodiment. In view of the above circumstances, the surface-emitting laser array chip is designed as illustrated in FIG. 44A, such that the light exit directions are inclined with reference to the X direction and the Y direction in a planar view (when viewed from the +X direction). This happens because the center points of the groups are inclined with reference to the center of the lens. FIG. 44B is a diagram illustrating the detection directions of the four photodiodes of the photodiode array according to the fourth embodiment. In a similar manner to the above, the center of the lens may be disposed at the center of the four-way split photodiode array chip (photodiode array chip) of the detection module DM, such that the detection directions (the incident directions at which the light enters the photoreceptors) become as illustrated in FIG. 44B. FIG. 45 is a diagram illustrating the light exit directions of a plurality of light source modules and the detection directions of a plurality of detection modules in an optical sensor according to the fourth embodiments The detection directions and the light exit directions of the above configuration are illustrated in FIG. 45 with the layout of the probes. The light exit directions and the detection directions are inclined with reference to the X direction and the Y direction in a planar view (when viewed from the +X direction).

As in the sensitivity distribution described above, the light is anisotropic. Accordingly, in the above configuration according to the fourth embodiment, a higher sensitivity is expected at the point X in FIG. 45.

An inverse problem estimation is performed with the design and layout as illustrated in FIG. 44A and FIG. 44B in a similar manner to the first embodiment. As a result, it was found that the detectable area expands.

Note that in the embodiments described above, the number of the light source modules LM of the irradiation system and the number of the detection modules DM of the detection system may be varied as desired. It is satisfactory as long as the irradiation system includes at least one light source module LM. In a similar manner, it is satisfactory as long as the detection system includes at least one detection module DM.

In the embodiments described above, the configuration of the light source module LM (light irradiator) may be changed as desired. For example, the layout or the number of the surface-emitting laser array chips in the light irradiator may be changed as desired. Moreover, for example, the types, shapes, sizes, and the number of the lenses may be changed as desired.

In the embodiments described above, a surface emitting laser is used for the light source of a light irradiator. However, for example, an end-surface emitting laser (laser diode (LD)), a light-emitting diode (LED), organic electroluminescence (EL) element, and a laser other than semiconductor lasers may be used.

In the embodiments described above, a prism is used for the reflection member of a light irradiator. However, other elements such as a mirror may be used instead of the prism.

The number of groups or layout in the surface-emitting laser array chip according to the second example, or the number of the channels or the layout in each of the groups may be changed as desired.

The configuration of the detection module DM (photodetector) may be changed as desired. For example, the aperture may be omitted. Moreover, for example, the split lens may be omitted.

As a matter of course, the shape, size, material, number, dimension, or numerical value of the elements or parts described above are given by way of example, and may be changed as desired.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. An optical sensor comprising:
an irradiation system including at least one light irradiator, the at least one irradiator including
a surface emitting laser array having a plurality of light-emitting units, and
a lens disposed in an optical path of the plurality of rays of light emitted from the plurality of light-emitting units to cause light exit directions of at least two of the plurality of light-emitting units to be not parallel to each other, such that the at least one irradiator irradiates a same point of a test object with a plurality of rays of light that are not parallel to each other; and
a detection system configured to detect the plurality of rays of light that are emitted from the irradiation system and propagated inside the test object, wherein
the plurality of light-emitting units of the surface emitting laser array include a first light-emitting unit furthest from an optical axis of the lens and a second light-emitting unit second furthest from the optical axis of the lens,
the first light-emitting unit and the second light-emitting unit are not parallel with each other,
a light exit direction of the first light-emitting unit has a larger tilt angle with respect to an optical axis of the lens than a light exit direction of the second light-emitting unit,
each one of the plurality of light-emitting units includes an approximately ring-shaped dielectric at a light exit area, and
a center point of the dielectric of at least one of the at least two of the plurality of light-emitting units is displaced from the center point of the light exit area.

2. The optical sensor according to claim 1, wherein the light exit direction of the at least one of the at least two of the plurality of light-emitting units is oblique with reference to an optical axis of the lens.

3. The optical sensor according to claim 1, wherein among at least two of the light-emitting units, relative positions of a center point of the dielectric and a center point of the light exit area are different from each other.

4. The optical sensor according to claim 1, wherein the light irradiator further includes a member, the member being disposed on an optical path of a plurality of rays of light emitted from the at least two of the light-emitting units and passes through the lens, the member having a reflection plane that reflects the plurality of rays of light.

5. The optical sensor according to claim 1, wherein the lens and the surface emitting laser array have a space therebetween filled with a transparent resin whose refractive index is equivalent to that of the lens.

6. The optical sensor according to claim 1, wherein the detection system includes at least one photodetector including a plurality of photoreceptors configured to detect the plurality of rays of light that are emitted from the light irradiator and propagated inside the test object.

7. The optical sensor according to claim 6, wherein the photodetector is disposed between the test object and the plurality of photoreceptors, and has a member provided with a transmissive portion configured to transmit a part of each of the plurality of rays of light propagated inside the test object.

8. The optical sensor according to claim 7, wherein the photodetector includes a light-receptive lens configured to guide the part of each of the plurality of rays of light to the plurality of photoreceptors.

9. The optical sensor according to claim 6, wherein
the light irradiator of the irradiation system includes a plurality of light irradiators,
the photodetector of the detection system includes a plurality of photodetectors,
the plurality of light irradiators and the plurality of photodetectors are disposed for the test object such that the light irradiator and the photodetector are arranged so as to be next to each other in any of two directions that are orthogonal to each other,
light exit directions of the plurality of rays of light emitted from the plurality of light irradiators are inclined with reference to the two directions, and
incident directions of the plurality of rays of light propagated inside the test object and entering the photodetector are inclined with reference to the two directions.

10. The optical sensor according to claim 6, wherein
the light irradiator of the irradiation system includes a plurality of light irradiators,
the photodetector of the detection system includes a plurality of photodetectors,
the plurality of light irradiators and the plurality of photodetectors are disposed for the test object such that two of either one of the light irradiator and the photodetector are at two vertices of a regular triangle separately, and
one of the other one of the light irradiator and the photodetector is at a remaining vertex of the regular triangle.

11. The optical sensor according to claim 1, wherein the light irradiator includes a member that contacts the test object and is composed of a material whose refractive index is greater than that of the test object.

12. The optical sensor according to claim 1, wherein the lens has a convex shape towards the surface emitting laser array.

13. An optical inspection device comprising:
the optical sensor according to claim 1; and
an optical property calculator configured to calculate an optical property of the test object based on a detection result of the optical sensor.

14. A method of detecting an optical property with an optical sensor, the optical sensor including an irradiation system including at least one light irradiator, the at least one irradiator including a surface emitting laser array having a plurality of light-emitting units, and a lens disposed in an optical path of the plurality of rays of light emitted from the plurality of light-emitting units to cause light exit directions of at least two of the plurality of light-emitting units to be not parallel to each other, such that the at least one irradiator irradiates a same point of a test object with a plurality of rays of light that are not parallel to each other, and a detection system configured to detect the plurality of rays of light that are emitted from the irradiation system and propagated inside the test object, the method comprising:
detecting an optical property of the test object using the optical sensor;
calculating a sensitivity distribution of light on the test object; and
calculating an optical property of the test object through solving an inverse problem based on the sensitivity distribution,
the plurality of light-emitting units of the surface emitting laser array including a first light-emitting unit furthest from an optical axis of the lens and a second light-emitting unit second furthest from the optical axis of the lens,
the first light-emitting unit and the second light-emitting unit not being parallel with each other,
a light exit direction of the first light-emitting unit having a larger tilt angle with respect to an optical axis of the lens than a light exit direction of the second light-emitting unit,
each one of the plurality of light-emitting units including an approximately ring-shaped dielectric at a light exit area, and
a center point of the dielectric of at least one of the at least two of the plurality of light-emitting units being displaced from the center point of the light exit area.

* * * * *